US005847096A

United States Patent [19]
Schubert et al.

[11] Patent Number: 5,847,096
[45] Date of Patent: Dec. 8, 1998

[54] DNA CONSTRUCTS ENCODING CD4 FUSION PROTEINS

[75] Inventors: Manfred Schubert, Rockville; George G. Harmison, II, Silver Spring, both of Md.; Chang-Jie Chen, Herndon, Va.; Akhil Banjerjea, Rockville, Md.

[73] Assignee: The United States of America as represented by the Secretary of the Department of Health and Human Services, Washington, D.C.

[21] Appl. No.: 418,848

[22] Filed: Apr. 7, 1995

Related U.S. Application Data

[63] Continuation of Ser. No. 936,849, Aug. 28, 1992, abandoned, which is a continuation-in-part of Ser. No. 751,830, Aug. 30, 1991, abandoned.

[51] Int. Cl.⁶ .............................. C12N 15/12; C12N 1/00; C07H 21/04; C07H 14/73
[52] U.S. Cl. ...................... 536/23.4; 536/23.5; 536/24.5; 435/69.7
[58] Field of Search ................................ 435/320.1, 69.1, 435/69.7, 172.3; 536/23.4, 23.5, 24.5

[56] References Cited

U.S. PATENT DOCUMENTS 5,306,631  4/1994  Harrison et al. ...................... 435/172.3

FOREIGN PATENT DOCUMENTS

WO 90/12087  10/1990  WIPO .

OTHER PUBLICATIONS

Buonocore et al., Proc. Natl. Acad. Sci. USA 90:2695–2699 (1993).
Chaudhary et al., Nature 335:369–372 (1988).
Young et al., Science 250:1421–1423 (1990).
M. Poznansky et al. (1991) J. Virology 65(1): 532–536.
A. J. Zaug et al (1980) Cell 19:331–338.
B. N. Fields, M.D. et al., EDS. *Fundamental Virology*–2nd Ed. New York: Raven Press, 1991, pp. 647,660–662.
M. C. Poznansky et al (1991) Int. Conf. Aids 7(2): 25 Abstract No. W.A. 13.
B. Crise et al (1990) J. Virol. 64(11) : 5585–5593.
L. Buonocore et al (1990) Nature 343: 625–628.
D. N. Levy et al (1991) Int. Conf. Aids 7(1): 98, Abstract No. M. A. 1026.
M. Vasseur et al (1990) J. Cell. Biochem. *Supp. 14D*:162, Abstract No. L453.
N. Sarver et al (1990) Science 247: 1222 –1225.

*Primary Examiner*—George C. Elliott
*Assistant Examiner*—Johnny F. Railey, II
*Attorney, Agent, or Firm*—Morgan & Finnegan, L.L.P.

[57] ABSTRACT

The subject invention relates to defective, interfering HIV particles and uses thereof. In particular, these particles encode a membrane bound receptor protein, as well as multitarget ribozymes, which together interfere with the production of infectious HIV by a host cell by downregulating the amount of HIV envelope protein on the surface of the cell as well as the amount of HIV genomic RNA.

22 Claims, 51 Drawing Sheets

F I G. I

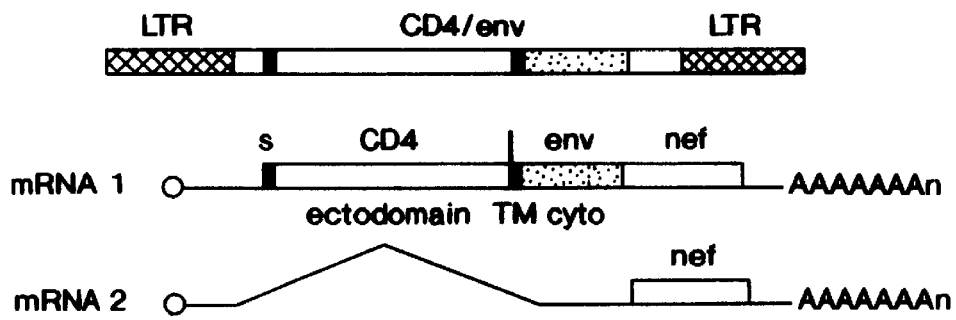
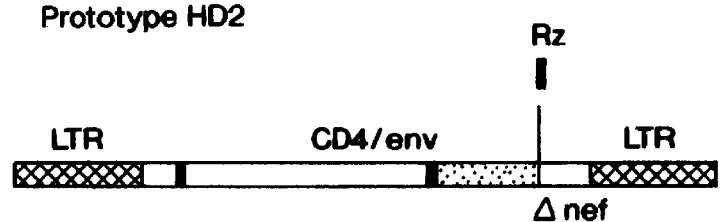
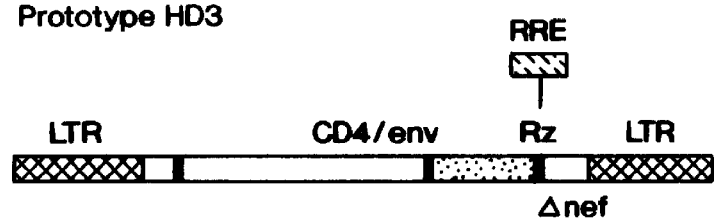
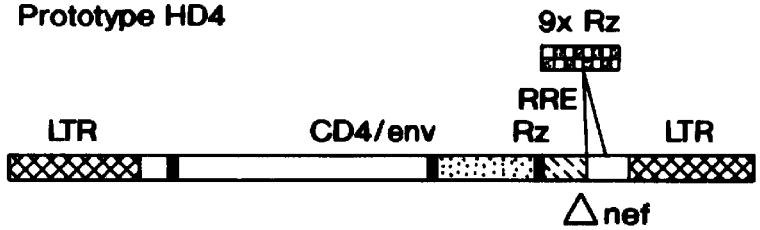
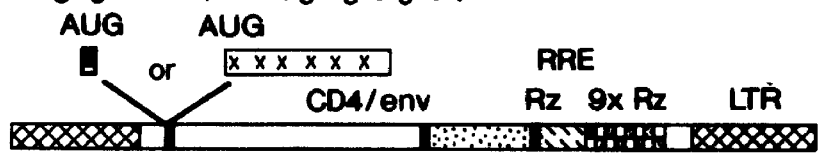
FIG. 2 env 0 ug
CD4/env 0 ug env 0.05 ug
CD4/env 0 ug env 0 ug
CD4/env 0.20 ug env 0.05 ug
CD4/env 0.01 ug env 0.05 ug
CD4/env 0.04 ug env 0.05 ug
CD4/env 0.20 ug pNL 4-3: 1 ug
pGem 4Z: 1 ug pNL 4-3: 1 ug
pHD3: 1 ug Prototype HD1
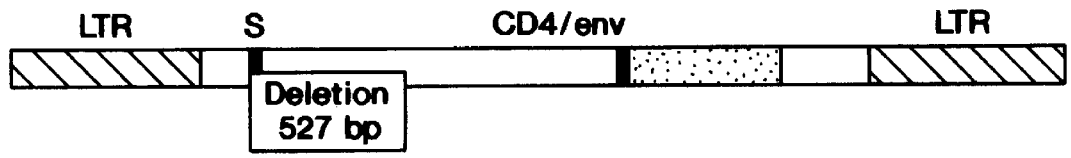
Prototype HD3
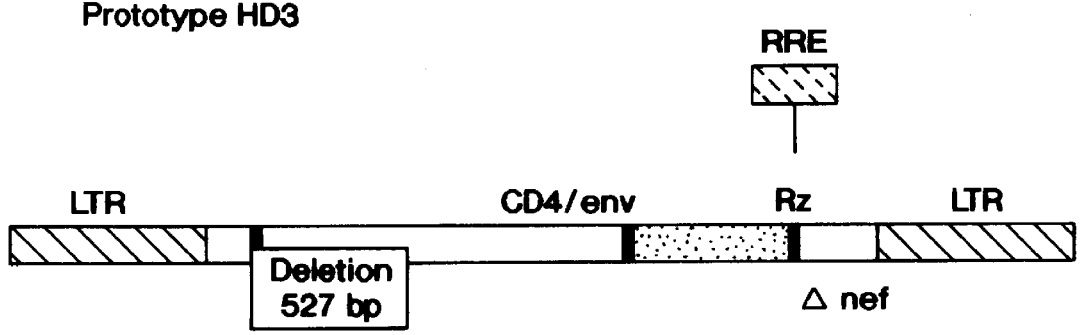
Cotransfection with pNL4-3
into Hela T4 cells
|  | p24 | Syncytia |
|---|---|---|
| HD1 | low | no |
| HD1 Deletion | high | yes |
| HD3 | low | no |
| HD3 Deletion | high | yes |
FIG. 11

FIG. 18

```
AAGCTTCATA  TGCCATAATA  CTGATGAGTC  CGTGAGGACG           40
AAACTGTGAC  GCGGCCGCCT  CGAGGCGCGC  GCATGCCTGC           80
AGGTCGACTC  TAGAGCTTCA  TATGGTACAT  TGCTGATGAG          120
TCCGTGAGGA  CGAAACTGTG  CTGCGGCCGC                      150
```

FIG. 19A

```
TGGAAGGGCT AATTTGGTCC CAAAAAAGAC AAGAGATCCT      40
TGATCTGTGG ATCTACCACA CACAAGGCTA CTTCCCTGAT      80
TGGCAGAACT ACACACCAGG GCCAGGGATC AGATATCCAC     120
TGACCTTTGG ATGGTGCTTC AAGTTAGTAC CAGTTGAACC     160
AGAGCAAGTA GAAGAGGCCA ATGAAGGAGA GAACAACAGC     200
TTGTTACACC CTATGAGCCA GCATGGGATG GAGGACCCGG     240
AGGGAGAAGT ATTAGTGTGG AAGTTTGACA GCCTCCTAGC     280
ATTTCGTCAC ATGGCCCGAG AGCTGCATCC GGAGTACTAC     320
AAAGACTGCT GACATCGAGC TTTCTACAAG GGACTTTCCG     360
CTGGGGACTT TCCAGGGAGG TGTGGCCTGG GCGGGACTGG     400
GGAGTGGCGA GCCCTCAGAT GCTACATATA AGCAGCTGCT     440
TTTTGCCTGT ACTGGGTCTC TCTGGTTAGA CCAGATCTGA     480
GCCTGGGAGC TCTCTGGCTA ACTAGGGAAC CCACTGCTTA     520
AGCCTCAATA AAGCTTGCCT TGAGTGCTCA AAGTAGTGTG     560
TGCCCGTCTG TTGTGTGACT CTGGTAACTA GAGATCCCTC     600
AGACCCTTTT AGTCAGTGTG GAAAATCTCT AGCAGTGGCG     640
CCCGAACAGG GACTTGAAAG CGAAAGTAAA GCCAGAGGAG     680
ATCTCTCGAC GCAGGACTCG GCTTGCTGAA GCGCGCACGG     720
CAAGAGGCGA GGGGCGGCGA CTGGTGAGTA CGCCAAAAAT     760
TTTGACTAGC GGAGGCTAGA AGGAGAGAGA TGAACCGGGG     800
AGTCCCTTTT AGTCACTTGC TTCTGGTGCT GCAACTGGCG     840
CTCCTCCCAG CAGCCACTCA GGGAAAGAAA GTGGTGCTGG     880
GCAAAAAGG GGATACAGTG GAACTGACCT GTACAGCTTC      920
CCAGAAGAAG AGCATACAAT TCCACTGGAA AAACTCCAAC     960
CAGATAAAGA TTCTGGGAAA TCAGGGCTCC TTCTTAACTA    1000
AAGGTCCATC CAAGCTGAAT GATCGCGCTG ACTCAAGAAG    1040
AAGCCTTTGG GACCAAGGAA ACTTCCCCCT GATCATTAAG    1080
AATCTTAAGA TAGAAGACTC AGATACTTAC ATCTGTGAAG    1120
TGGAGGACCA GAAGGAGGAG GTGCAATTGC TAGTGTTCGG    1160
ATTGACTGCC AACTCTGACA CCCACCTGCT TCAGGGGCAG    1200
AGCCTGACCC TGACCTTGGA GAGCCCCCT GGTAGTAGCC     1240
CCTCAGTGCA ATGTAGGAGT CCAAGGGGTA AAAACATACA    1280
GGGGGGGAAG ACCCTCTCCG TGTCTCAGCT GGAGCTCCAG    1320
GATAGTGGCA CCTGGACATG CACTGTCTTG CAGAACCAGA    1360
AGAAGGTGGA GTTCAAAATA GACATCGTGG TGCTAGCTTT    1400
CCAGAAGGCC TCCAGCATAG TCTATAAGAA AGAGGGGGAA    1440
CAGGTGGAGT TCTCCTTCCC ACTCGCCTTT ACAGTTGAAA    1480
AGCTGACGGG CAGTGGCGAG CTGTGGTGGC AGGCGGAGAG    1520
GGCTTCCTCC TCCAAGTCTT GGATCATCTT TGACCTGAAG    1560
AACAAGGAAG TGTCTGTAAA ACGGGTTACC CAGGACCCTA    1600
AGCTCCAGAT GGGCAAGAAG CTCCGCTCC ACCTCACCCT     1640
GCCCCAGGCC TTGCCTCAGT ATGCTGGCTC TGGAAACCTC    1680
ACCCTGGCCC TTGAAGCGAA AACAGGAAAG TTGCATCAGG    1720
AAGTGAACCT GGTGGTGATG AGAGCCACTC AGCTCCAGAA    1760
AAATTTGACC TGTGAGGTGT GGGGACCCAC CTCCCCTAAG    1800
CTGATGCTGA GCTTGAAACT GGAGAACAAG GAGGCAAAGG    1840
TCTCGAAGCG GGAGAAGGCG GTGTGGGTGC TGAACCCTGA    1880
GGCGGGGATG TGGCAGTGTC TGCTGAGTGA CTCGGGACAG    1920
GTCCTGCTGG AATCCAACAT CAAGGTTCTG CCCATATGGT    1960
CCACCCCAGT GCAGCCAATG TTATTCATAA TGATAGTAGG    2000
AGGCTTGGTA GGTTTAAGAA TAGTTTTTGC TGTACTTTCT    2040
```

FIG. 19B

```
ATAGTGAATA GAGTTAGGCA GGGATATTCA CCATTATCGT      2080
TTCAGACCCA CCTCCCAATC CCGAGGGGAC CCGACAGGCC      2120
CGAAGGAATA GAAGAAGAAG GTGGAGAGAG AGACAGAGAC      2160
AGATCCATTC GATTAGTGAA CGGATCCTTA GCACTTATCT      2200
GGGACGATCT GCGGAGCCTG TGCCTCTTCA GCTACCACCG      2240
CTTGAGAGAC TTACTCTTGA TTGTAACGAG GATTGTGGAA      2280
CTTCTGGGAC GCAGGGGGTG GGAAGCCCTC AAATATTGGT      2320
GGAATCTCCT ACAGTATTGG AGTCAGGAAC TAAAGAATAG      2360
TGCTGTTAAC TTGCTCAATG CCACAGCCAT AGCAGTAGCT      2400
GAGGGGACAG ATAGGGTTAT AGAAGTATTA CAAGCAGCTT      2440
ATAGAGCTAT TCGCCACATA CCTAGAAGAA TAAGACAGGG      2480
CTTGGAAAGG ATTTTGCTAT AAGATGGGTG GCAAGTGGTC      2520
AAAAAGTAGT GTGATTGGAT GGCCTGCTGT AAGGGAAAGA      2560
ATGAGACGAG CTGAGCCAGC AGCAGATGGG GTGGGAGCAG      2600
TATCTCGAGA CCTAGAAAAA CATGGAGCAA TCACAAGTAG      2640
CAATACAGCA GCTAACAATG CTGCTTGTGC CTGGCTAGAA      2680
GCACAAGAGG AGGAAGAGGT GGGTTTTCCA GTCACACCTC      2720
AGGTACCTTT AAGACCAATG ACTTACAAGG CAGCTGTAGA      2760
TCTTAGCCAC TTTTTAAAAG AAAAGGGGGG ACTGGAAGGG      2800
CTAATTCACT CCCAAAGAAG ACAAGATATC CTTGATCTGT      2840
GGATCTACCA CACACAAGGC TACTTCCCTG ATTGGCAGAA      2880
CTACACACCA GGGCCAGGGG TCAGATATCC ACTGACCTTT      2920
GGATGGTGCT ACAAGCTAGT ACCAGTTGAG CCAGATAAGG      2960
TAGAAGAGGC CAATAAAGGA GAGAACACCA GCTTGTTACA      3000
CCCTGTGAGC CTGCATGGAA TGGATGACCC TGAGAGAGAA      3040
GTGTTAGAGT GGAGGTTTGA CAGCCGCCTA GCATTTCATC      3080
ACGTGGCCCG AGAGCTGCAT CCGGAGTACT TCAAGAACTG      3120
CTGACATCGA GCTTGCTACA AGGGACTTTC CGCTGGGGAC      3160
TTTCCAGGGA GGCGTGGCCT GGGCGGGACT GGGGAGTGGC      3200
GAGCCCTCAG ATGCTGCATA TAAGCAGCTG CTTTTTGCCT      3240
GTACTGGGTC TCTCTGGTTA GACCAGATCT GAGCCTGGGA      3280
GCTCTCTGGC TAACTAGGGA ACCCACTGCT TAAGCCTCAA      3320
TAAAGCTTGC CTTGAGTGCT TCAAGTAGTG TGTGCCCGTC      3360
TGTTGTGTGA CTCTGGTAAC TAGAGATCCC TCAGACCCTT      3400
TTAGTCAGTG TGGAAAATCT CTAGCA                    3426
```

FIG. 20A

```
GAATTCTGTA ATACGACTCA CTATAGGTCT CTCTGGTTAG      40
ACCAGATCTG AGCCTGGGAG CTCTCTGGCT AACTAGGGAA      80
CCCACTGCTT AAGCCTCAAT AAAGCTTGCC TTGAGTGCTC     120
AAAGTAGTGT GTGCCCGTCT GTTGTGTGAC TCTGGTAACT     160
AGAGATCCCT CAGACCCTTT TAGTCAGTGT GGAAAATCTC     200
TAGCAGTGGC GCCCGAACAG GGACTTGAAA GCGAAAGTAA     240
AGCCAGAGGA GATCTCTCGA CGCAGGACTC GGCTTGCTGA     280
AGCGCGCACG GCAAGAGGCG AGGGGCGGCG ACTGGTGAGT     320
ACGCCAAAAA TTTTGACTAG CGGAGGCTAG AAGGAGAGAG     360
ATGAACCGGG GAGTCCCTTT TAGTCACTTG CTTCTGGTGC     400
TGCAACTGGC GCTCCTCCCA GCAGCCACTC AGGGAAAGAA     440
AGTGGTGCTG GGCAAAAAAG GGGATACAGT GGAACTGACC     480
TGTACAGCTT CCCAGAAGAA GAGCATACAA TTCCACTGGA     520
AAAACTCCAA CCAGATAAAG ATTCTGGGAA ATCAGGGCTC     560
CTTCTTAACT AAAGGTCCAT CCAAGCTGAA TGATCGCGCT     600
GACTCAAGAA GAAGCCTTTG GGACCAAGGA AACTTCCCCC     640
TGATCATTAA GAATCTTAAG ATAGAAGACT CAGATACTTA     680
CATCTGTGAA GTGGAGGACC AGAAGGAGGA GGTGCAATTG     720
CTAGTGTTCG GATTGACTGC CAACTCTGAC ACCCACCTGC     760
TTCAGGGGCA GAGCCTGACC CTGACCTTGG AGAGCCCCCC     800
TGGTAGTAGC CCCTCAGTGC AATGTAGGAG TCCAAGGGGT     840
AAAAACATAC AGGGGGGGAA GACCCTCTCC GTGTCTCAGC     880
TGGAGCTCCA GGATAGTGGC ACCTGGACAT GCACTGTCTT     920
GCAGAACCAG AAGAAGGTGG AGTTCAAAAT AGACATCGTG     960
GTGCTAGCTT TCCAGAAGGC CTCCAGCATA GTCTATAAGA    1000
AAGAGGGGA ACAGGTGGAG TTCTCCTTCC CACTCGCCTT    1040
TACAGTTGAA AAGCTGACGG GCAGTGGCGA GCTGTGGTGG    1080
CAGGCGGAGA GGGCTTCCTC CTCCAAGTCT TGGATCATCT    1120
TTGACCTGAA GAACAAGGAA GTGTCTGTAA AACGGGTTAC    1160
CCAGGACCCT AAGCTCCAGA TGGGCAAGAA GCTCCCGCTC    1200
CACCTCACCC TGCCCCAGGC CTTGCCTCAG TATGCTGGCT    1240
CTGGAAACCT CACCCTGGCC CTTGAAGCGA AAACAGGAAA    1280
GTTGCATCAG GAAGTGAACC TGGTGGTGAT GAGAGCCACT    1320
CAGCTCCAGA AAAATTTGAC CTGTGAGGTG TGGGGACCCA    1360
CCTCCCCTAA GCTGATGCTG AGCTTGAAAC TGGAGAACAA    1400
GGAGGCAAAG GTCTCGAAGC GGGAGAAGGC GGTGTGGGTG    1440
CTGAACCCTG AGGCGGGGAT GTGGCAGTGT CTGCTGAGTG    1480
ACTCGGGACA GGTCCTGCTG GAATCCAACA TCAAGGTTCT    1520
GCCCATATGG TCCACCCCAG TGCAGCCAAT GTTATTCATA    1560
ATGATAGTAG GAGGCTTGGT AGGTTTAAGA ATAGTTTTTG    1600
CTGTACTTTC TATAGTGAAT AGAGTTAGGC AGGGATATTC    1640
ACCATTATCG TTTCAGACCC ACCTCCCAAT CCCGAGGGGA    1680
CCCGACAGGC CCGAAGGAAT AGAAGAAGAA GGTGGAGAGA    1720
GAGACAGAGA CAGATCCATT CGATTAGTGA ACGGATCCTT    1760
AGCACTTATC TGGGACGATC TGCGGAGCCT GTGCCTCTTC    1800
AGCTACCACC GCTTGAGAGA CTTACTCTTG ATTGTAACGA    1840
GGATTGTGGA ACTTCTGGGA CGCAGGGGGT GGGAAGCCCT    1880
CAAATATTGG TGGAATCTCC TACAGTATTG GAGTCAGGAA    1920
CTAAAGAATA GTGCTGTTAA CTTGCTCAAT GCCACAGCCA    1960
TAGCAGTAGC TGAGGGGACA GATAGGGTTA TAGAAGTATT    2000
ACAAGCAGCT TATAGAGCTA TTCGCCACAT ACCTAGAAGA    2040
```

FIG. 20B

```
ATAAGACAGG GCTTGGAAAG GATTTTGCTA TAAGATGGGT              2080
GGCAAGTGGT CAAAAAGTAG TGTGATTGGA TGGCCTGCTG              2120
TAAGGGAAAG AATGAGACGA GCTGAGCCAG CAGCAGATGG              2160
GGTGGGAGCA GTATCTCGAG ACCTAGAAAA ACATGGAGCA              2200
ATCACAAGTA GCAATACAGC AGCTAACAAT GCTGCTTGTG              2240
CCTGGCTAGA AGCACAAGAG GAGGAAGAGG TGGGTTTTCC              2280
AGTCACACCT CAGGTACCTT TAAGACCAAT GACTTACAAG              2320
GCAGCTGTAG ATCTTAGCCA CTTTTTAAAA GAAAAGGGGG              2360
GACTGGAAGG GCTAATTCAC TCCCAAAGAA GACAAGATAT              2400
CCTTGATCTG TGGATCTACC ACACACAAGG CTACTTCCCT              2440
GATTGGCAGA ACTACACACC AGGGCCAGGG GTCAGATATC              2480
CACTGACCTT TGGATGGTGC TACAAGCTAG TACCAGTTGA              2520
GCCAGATAAG GTAGAAGAGG CCAATAAAGG AGAGAACACC              2560
AGCTTGTTAC ACCCTGTGAG CCTGCATGGA ATGGATGACC              2600
CTGAGAGAGA AGTGTTAGAG TGGAGGTTTG ACAGCCGCCT              2640
AGCATTTCAT CACGTGGCCC GAGAGCTGCA TCCGGAGTAC              2680
TTCAAGAACT GCTGACATCG AGCTTGCTAC AAGGGACTTT              2720
CCGCTGGGGA CTTTCCAGGG AGGCGTGGCC TGGGCGGGAC              2760
TGGGGAGTGG CGAGCCCTCA GATGCTGCAT ATAAGCAGCT              2800
GCTTTTTGCC TGTACTGGGT CTCTCTGGTT AGACCAGATC              2840
TGAGCCTGGG AGCTCTCTGG CTAACTAGGG AACCCACTGC              2880
TTAAGCCTCA ATAAAGCTTG CCTTGAGTGC TTCAAAAAAA              2920
AAAAAAAAAT GCATCTGCAG                                    2940
```

FIG. 21A

```
TGGAAGGGCT AATTTGGTCC CAAAAAAGAC AAGAGATCCT         40
TGATCTGTGG ATCTACCACA CACAAGGCTA CTTCCCTGAT         80
TGGCAGAACT ACACACCAGG GCCAGGGATC AGATATCCAC        120
TGACCTTTGG ATGGTGCTTC AAGTTAGTAC CAGTTGAACC        160
AGAGCAAGTA GAAGAGGCCA ATGAAGGAGA GAACAACAGC        200
TTGTTACACC CTATGAGCCA GCATGGGATG GAGGACCCGG        240
AGGGAGAAGT ATTAGTGTGG AAGTTTGACA GCCTCCTAGC        280
ATTTCGTCAC ATGGCCCGAG AGCTGCATCC GGAGTACTAC        320
AAAGACTGCT GACATCGAGC TTTCTACAAG GGACTTTCCG        360
CTGGGGACTT TCCAGGGAGG TGTGGCCTGG GCGGGACTGG        400
GGAGTGGCGA GCCCTCAGAT GCTACATATA AGCAGCTGCT        440
TTTTGCCTGT ACTGGGTCTC TCTGGTTAGA CCAGATCTGA        480
GCCTGGGAGC TCTCTGGCTA ACTAGGGAAC CCACTGCTTA        520
AGCCTCAATA AAGCTTGCCT TGAGTGCTCA AAGTAGTGTG        560
TGCCCGTCTG TTGTGTGACT CTGGTAACTA GAGATCCCTC        600
AGACCCTTTT AGTCAGTGTG GAAAATCTCT AGCAGTGGCG        640
CCCGAACAGG GACTTGAAAG CGAAAGTAAA GCCAGAGGAG        680
ATCTCTCGAC GCAGGACTCG GCTTGCTGAA GCGCGCACGG        720
CAAGAGGCGA GGGGCGGCGA CTGGTGAGTA CGCCAAAAAT        760
TTTGACTAGC GGAGGCTAGA AGGAGAGAGA TGAACCGGGG        800
AGTCCCTTTT AGTCACTTGC TTCTGGTGCT GCAACTGGCG        840
CTCCTCCCAG CAGCCACTCA GGGAAGAAA GTGGTGCTGG         880
GCAAAAAGG GGATACAGTG GAACTGACCT GTACAGCTTC         920
CCAGAAGAAG AGCATACAAT TCCACTGGAA AAACTCCAAC        960
CAGATAAAGA TTCTGGGAAA TCAGGGCTCC TTCTTAACTA       1000
AAGGTCCATC CAAGCTGAAT GATCGCGCTG ACTCAAGAAG       1040
AAGCCTTTGG GACCAAGGAA ACTTCCCCCT GATCATTAAG       1080
AATCTTAAGA TAGAAGACTC AGATACTTAC ATCTGTGAAG       1120
TGGAGGACCA GAAGGAGGAG GTGCAATTGC TAGTGTTCGG       1160
ATTGACTGCC AACTCTGACA CCCACCTGCT TCAGGGGCAG       1200
AGCCTGACCC TGACCTTGGA GAGCCCCCCT GGTAGTAGCC       1240
CCTCAGTGCA ATGTAGGAGT CCAAGGGGTA AAAACATACA       1280
GGGGGGGAAG ACCCTCTCCG TGTCTCAGCT GGAGCTCCAG       1320
GATAGTGGCA CCTGGACATG CACTGTCTTG CAGAACCAGA       1360
AGAAGGTGGA GTTCAAAATA GACATCGTGG TGCTAGCTTT       1400
CCAGAAGGCC TCCAGCATAG TCTATAAGAA AGAGGGGGAA       1440
CAGGTGGAGT TCTCCTTCCC ACTCGCCTTT ACAGTTGAAA       1480
AGCTGACGGG CAGTGGCGAG CTGTGGTGGC AGGCGGAGAG       1520
GGCTTCCTCC TCCAAGTCTT GGATCATCTT TGACCTGAAG       1560
AACAAGGAAG TGTCTGTAAA ACGGGTTACC CAGGACCCTA       1600
AGCTCCAGAT GGGCAAGAAG CTCCCGCTCC ACCTCACCCT       1640
GCCCCAGGCC TTGCCTCAGT ATGCTGGCTC TGGAAACCTC       1680
ACCCTGGCCC TTGAAGCGAA AACAGGAAAG TTGCATCAGG       1720
AAGTGAACCT GGTGGTGATG AGAGCCACTC AGCTCCAGAA       1760
AAATTTGACC TGTGAGGTGT GGGGACCCAC CTCCCCTAAG       1800
CTGATGCTGA GCTTGAAACT GGAGAACAAG GAGGCAAAGG       1840
TCTCGAAGCG GGAGAAGGCG GTGTGGGTGC TGAACCCTGA       1880
GGCGGGGATG TGGCAGTGTC TGCTGAGTGA CTCGGGACAG       1920
GTCCTGCTGG AATCCAACAT CAAGGTTCTG CCCATATGGT       1960
CCACCCCAGT GCAGCCAATG TTATTCATAA TGATAGTAGG       2000
AGGCTTGGTA GGTTTAAGAA TAGTTTTTGC TGTACTTTCT       2040
```

FIG. 21B

```
ATAGTGAATA GAGTTAGGCA GGGATATTCA CCATTATCGT        2080
TTCAGACCCA CCTCCCAATC CCGAGGGGAC CCGACAGGCC        2120
CGAAGGAATA GAAGAAGAAG GTGGAGAGAG AGACAGAGAC        2160
AGATCCATTC GATTAGTGAA CGGATCCTTA GCACTTATCT        2200
GGGACGATCT GCGGAGCCTG TGCCTCTTCA GCTACCACCG        2240
CTTGAGAGAC TTACTCTTGA TTGTAACGAG GATTGTGGAA        2280
CTTCTGGGAC GCAGGGGGTG GGAAGCCCTC AAATATTGGT        2320
GGAATCTCCT ACAGTATTGG AGTCAGGAAC TAAAGAATAG        2360
TGCTGTTAAC TTGCTCAATG CCACAGCCAT AGCAGTAGCT        2400
GAGGGGACAG ATAGGGTTAT AGAAGTATTA CAAGCAGCTT        2440
ATAGAGCTAT TCGCCACATA CCTAGAAGAA TAAGACAGGG        2480
CTTGGAAAGG ATTTTGCTAT AAGCATATGG TACATTGCTG        2520
ATGAGTCCGT GAGGACGAAA CTGTGCTGCG GCCGCTATAA        2560
GGTGGCAAGT GGTCAAAAAG TAGTGTGATT GGATGGCCTG        2600
CTGTAAGGGA AAGAATGAGA CGAGCTGAGC CAGCAGCAGA        2640
TGGGGTGGGA GCAGTATCTC GAGACCTAGA AAAACATGGA        2680
GCAATCACAA GTAGCAATAC AGCAGCTAAC AATGCTGCTT        2720
GTGCCTGGCT AGAAGCACAA GAGGAGGAAG AGGTGGGTTT        2760
TCCAGTCACA CCTCAGGTAC CTTTAAGACC AATGACTTAC        2800
AAGGCAGCTG TAGATCTTAG CCACTTTTTA AAAGAAAAGG        2840
GGGGACTGGA AGGGCTAATT CACTCCCAAA GAAGACAAGA        2880
TATCCTTGAT CTGTGGATCT ACCACACACA AGGCTACTTC        2920
CCTGATTGGC AGAACTACAC ACCAGGGCCA GGGGTCAGAT        2960
ATCCACTGAC CTTTGGATGG TGCTACAAGC TAGTACCAGT        3000
TGAGCCAGAT AAGGTAGAAG AGGCCAATAA AGGAGAGAAC        3040
ACCAGCTTGT TACACCCTGT GAGCCTGCAT GGAATGGATG        3080
ACCCTGAGAG AGAAGTGTTA GAGTGGAGGT TTGACAGCCG        3120
CCTAGCATTT CATCACGTGG CCCGAGAGCT GCATCCGGAG        3160
TACTTCAAGA ACTGCTGACA TCGAGCTTGC TACAAGGGAC        3200
TTTCCGCTGG GGACTTTCCA GGGAGGCGTG GCCTGGGCGG        3240
GACTGGGGAG TGGCGAGCCC TCAGATGCTG CATATAAGCA        3280
GCTGCTTTTT GCCTGTACTG GGTCTCTCTG GTTAGACCAG        3320
ATCTGAGCCT GGGAGCTCTC TGGCTAACTA GGGAACCCAC        3360
TGCTTAAGCC TCAATAAAGC TTGCCTTGAG TGCTTCAAGT        3400
AGTGTGTGCC CGTCTGTTGT GTGACTCTGG TAACTAGAGA        3440
TCCCTCAGAC CCTTTTAGTC AGTGTGGAAA ATCTCTAGCA        3480
```

FIG. 22A

```
TGGAAGGGCT AATTTGGTCC CAAAAAAGAC AAGAGATCCT      40
TGATCTGTGG ATCTACCACA CACAAGGCTA CTTCCCTGAT      80
TGGCAGAACT ACACACCAGG GCCAGGGATC AGATATCCAC     120
TGACCTTTGG ATGGTGCTTC AAGTTAGTAC CAGTTGAACC     160
AGAGCAAGTA GAAGAGGCCA ATGAAGGAGA GAACAACAGC     200
TTGTTACACC CTATGAGCCA GCATGGATG GAGGACCCGG      240
AGGGAGAAGT ATTAGTGTGG AAGTTTGACA GCCTCCTAGC     280
ATTTCGTCAC ATGGCCCGAG AGCTGCATCC GGAGTACTAC     320
AAAGACTGCT GACATCGAGC TTTCTACAAG GGACTTTCCG     360
CTGGGGACTT TCCAGGGAGG TGTGGCCTGG GCGGGACTGG     400
GGAGTGGCGA GCCCTCAGAT GCTACATATA AGCAGCTGCT     440
TTTTGCCTGT ACTGGGTCTC TCTGGTTAGA CCAGATCTGA     480
GCCTGGGAGC TCTCTGGCTA ACTAGGGAAC CCACTGCTTA     520
AGCCTCAATA AAGCTTGCCT TGAGTGCTCA AAGTAGTGTG     560
TGCCCGTCTG TTGTGTGACT CTGGTAACTA GAGATCCCTC     600
AGACCCTTTT AGTCAGTGTG GAAAATCTCT AGCAGTGGCG     640
CCCGAACAGG GACTTGAAAG CGAAAGTAAA GCCAGAGGAG     680
ATCTCTCGAC GCAGGACTCG GCTTGCTGAA GCGCGCACGG     720
CAAGAGGCGA GGGGCGGCGA CTGGTGAGTA CGCCAAAAAT     760
TTTGACTAGC GGAGGCTAGA AGGAGAGAGA TGAACCGGGG     800
AGTCCTTTT AGTCACTTGC TTCTGGTGCT GCAACTGGCG      840
CTCCTCCCAG CAGCCACTCA GGGAAGAAA GTGGTGCTGG      880
GCAAAAAGG GGATACAGTG GAACTGACCT GTACAGCTTC      920
CCAGAAGAAG AGCATACAAT TCCACTGGAA AAACTCCAAC     960
CAGATAAAGA TTCTGGGAAA TCAGGGCTCC TTCTTAACTA    1000
AAGGTCCATC CAAGCTGAAT GATCGCGCTG ACTCAAGAAG    1040
AAGCCTTTGG GACCAAGGAA ACTTCCCCCT GATCATTAAG    1080
AATCTTAAGA TAGAAGACTC AGATACTTAC ATCTGTGAAG    1120
TGGAGGACCA GAAGGAGGAG GTGCAATTGC TAGTGTTCGG    1160
ATTGACTGCC AACTCTGACA CCCACCTGCT TCAGGGGCAG    1200
AGCCTGACCC TGACCTTGGA GAGCCCCCT GGTAGTAGCC     1240
CCTCAGTGCA ATGTAGGAGT CCAAGGGGTA AAAACATACA    1280
GGGGGGGAAG ACCCTCTCCG TGTCTCAGCT GGAGCTCCAG    1320
GATAGTGGCA CCTGGACATG CACTGTCTTG CAGAACCAGA    1360
AGAAGGTGGA GTTCAAAATA GACATCGTGG TGCTAGCTTT    1400
CCAGAAGGCC TCCAGCATAG TCTATAAGAA AGAGGGGGAA    1440
CAGGTGGAGT TCTCCTTCCC ACTCGCCTTT ACAGTTGAAA    1480
AGCTGACGGG CAGTGGCGAG CTGTGGTGGC AGGCGGAGAG    1520
GGCTTCCTCC TCCAAGTCTT GGATCATCTT TGACCTGAAG    1560
AACAAGGAAG TGTCTGTAAA ACGGGTTACC CAGGACCCTA    1600
AGCTCCAGAT GGGCAAGAAG CTCCCGCTCC ACCTCACCCT    1640
GCCCCAGGCC TTGCCTCAGT ATGCTGGCTC TGGAAACCTC    1680
ACCCTGGCCC TTGAAGCGAA AACAGGAAAG TTGCATCAGG    1720
AAGTGAACCT GGTGGTGATG AGAGCCACTC AGCTCCAGAA    1760
AAATTTGACC TGTGAGGTGT GGGGACCCAC CTCCCCTAAG    1800
CTGATGCTGA GCTTGAAACT GGAGAACAAG GAGGCAAAGG    1840
TCTCGAAGCG GGAGAAGGCG GTGTGGGTGC TGAACCCTGA    1880
GGCGGGGATG TGGCAGTGTC TGCTGAGTGA CTCGGGACAG    1920
GTCCTGCTGG AATCCAACAT CAAGGTTCTG CCCATATGGT    1960
CCACCCCAGT GCAGCCAATG TTATTCATAA TGATAGTAGG    2000
AGGCTTGGTA GGTTTAAGAA TAGTTTTTGC TGTACTTTCT    2040
```

FIG. 22B

```
ATAGTGAATA GAGTTAGGCA GGGATATTCA CCATTATCGT        2080
TTCAGACCCA CCTCCCAATC CCGAGGGGAC CCGACAGGCC        2120
CGAAGGAATA GAAGAAGAAG GTGGAGAGAG AGACAGAGAC        2160
AGATCCATTC GATTAGTGAA CGGATCCTTA GCACTTATCT        2200
GGGACGATCT GCGGAGCCTG TGCCTCTTCA GCTACCACCG        2240
CTTGAGAGAC TTACTCTTGA TTGTAACGAG GATTGTGGAA        2280
CTTCTGGGAC GCAGGGGGTG GGAAGCCCTC AAATATTGGT        2320
GGAATCTCCT ACAGTATTGG AGTCAGGAAC TAAAGAATAG        2360
TGCTGTTAAC TTGCTCAATG CCACAGCCAT AGCAGTAGCT        2400
GAGGGGACAG ATAGGGTTAT AGAAGTATTA CAAGCAGCTT        2440
ATAGAGCTAT TCGCCACATA CCTAGAAGAA TAAGACAGGG        2480
CTTGGAAAGG ATTTTGCTAT AAGCATATGG TACATTGCTG        2520
ATGAGTCCGT GAGGACGAAA CTGTGCTGCG GCCGCAGGAG        2560
CTTTGTTCCT TGGGTTCTTG GGAGCAGCAG GAAGCACTAT        2600
GGGCTGCACG TCAATGACGC TGACGGTACA GGCCAGACAA        2640
TTATTGTCTG ATATAGTGCA GCAGCAGAAC AATTTGCTGA        2680
GGGCTATTGA GGCGCAACAG CATCTGTTGC AACTCACAGT        2720
CTGGGGCATC AAACAGCTCC AGGCAAGAAT CCTGGCTGTG        2760
GAAAGATACC TAAAGGACAA CAGCTCCTGC GGCCGCTATA        2800
AGGTGGCAAG TGGTCAAAAA GTAGTGTGAT TGGATGGCCT        2840
GCTGTAAGGG AAAGAATGAG ACGAGCTGAG CCAGCAGCAG        2880
ATGGGGTGGG AGCAGTATCT CGAGACCTAG AAAAACATGG        2920
AGCAATCACA AGTAGCAATA CAGCAGCTAA CAATGCTGCT        2960
TGTGCCTGGC TAGAAGCACA AGAGGAGGAA GAGGTGGGTT        3000
TTCCAGTCAC ACCTCAGGTA CCTTTAAGAC CAATGACTTA        3040
CAAGGCAGCT GTAGATCTTA GCCACTTTTT AAAAGAAAAG        3080
GGGGGACTGG AAGGGCTAAT TCACTCCCAA AGAAGACAAG        3120
ATATCCTTGA TCTGTGGATC TACCACACAC AAGGCTACTT        3160
CCCTGATTGG CAGAACTACA CACCAGGGCC AGGGGTCAGA        3200
TATCCACTGA CCTTTGGATG GTGCTACAAG CTAGTACCAG        3240
TTGAGCCAGA TAAGGTAGAA GAGGCCAATA AAGGAGAGAA        3280
CACCAGCTTG TTACACCCTG TGAGCCTGCA TGGAATGGAT        3320
GACCCTGAGA GAGAAGTGTT AGAGTGGAGG TTTGACAGCC        3360
GCCTAGCATT TCATCACGTG GCCCGAGAGC TGCATCCGGA        3400
GTACTTCAAG AACTGCTGAC ATCGAGCTTG CTACAAGGGA        3440
CTTTCCGCTG GGGACTTTCC AGGGAGGCGT GGCCTGGGCG        3480
GGACTGGGGA GTGGCGAGCC CTCAGATGCT GCATATAAGC        3520
AGCTGCTTTT TGCCTGTACT GGGTCTCTCT GGTTAGACCA        3560
GATCTGAGCC TGGGAGCTCT CTGGCTAACT AGGGAACCCA        3600
CTGCTTAAGC CTCAATAAAG CTTGCCTTGA GTGCTTCAAG        3640
TAGTGTGTGC CCGTCTGTTG TGTGACTCTG GTAACTAGAG        3680
ATCCCTCAGA CCCTTTTAGT CAGTGTGGAA AATCTCTAGC        3720
A                                                  3721
```

FIG. 23A

```
TGGAAGGGCT AATTTGGTCC CAAAAAAGAC AAGAGATCCT      40
TGATCTGTGG ATCTACCACA CACAAGGCTA CTTCCCTGAT      80
TGGCAGAACT ACACACCAGG GCCAGGGATC AGATATCCAC     120
TGACCTTTGG ATGGTGCTTC AAGTTAGTAC CAGTTGAACC     160
AGAGCAAGTA GAAGAGGCCA ATGAAGGAGA GAACAACAGC     200
TTGTTACACC CTATGAGCCA GCATGGGATG GAGGACCCGG     240
AGGGAGAAGT ATTAGTGTGG AAGTTTGACA GCCTCCTAGC     280
ATTTCGTCAC ATGGCCCGAG AGCTGCATCC GGAGTACTAC     320
AAAGACTGCT GACATCGAGC TTTCTACAAG GGACTTTCCG     360
CTGGGGACTT TCCAGGGAGG TGTGGCCTGG GCGGGACTGG     400
GGAGTGGCGA GCCCTCAGAT GCTACATATA AGCAGCTGCT     440
TTTTGCCTGT ACTGGGTCTC TCTGGTTAGA CCAGATCTGA     480
GCCTGGGAGC TCTCTGGCTA ACTAGGGAAC CCACTGCTTA     520
AGCCTCAATA AAGCTTGCCT TGAGTGCTCA AGTAGTGTG      560
TGCCCGTCTG TTGTGTGACT CTGGTAACTA GAGATCCCTC     600
AGACCCTTTT AGTCAGTGTG GAAAATCTCT AGCAGTGGCG     640
CCCGAACAGG GACTTGAAAG CGAAAGTAAA GCCAGAGGAG     680
ATCTCTCGAC GCAGGACTCG GCTTGCTGAA GCGCGCACGG     720
CAAGAGGCGA GGGGCGGCGA CTGGTGAGTA CGCCAAAAAT     760
TTTGACTAGC GGAGGCTAGA AGGAGAGAGA TGAACCGGGG     800
AGTCCCTTTT AGTCACTTGC TTCTGGTGCT GCAACTGGCG     840
CTCCTCCCAG CAGCCACTCA GGGAAAGAAA GTGGTGCTGG     880
GCAAAAAGG GGATACAGTG GAACTGACCT GTACAGCTTC      920
CCAGAAGAAG AGCATACAAT TCCACTGGAA AAACTCCAAC     960
CAGATAAAGA TTCTGGGAAA TCAGGGCTCC TTCTTAACTA    1000
AAGGTCCATC CAAGCTGAAT GATCGCGCTG ACTCAAGAAG    1040
AAGCCTTTGG GACCAAGGAA ACTTCCCCCT GATCATTAAG    1080
AATCTTAAGA TAGAAGACTC AGATACTTAC ATCTGTGAAG    1120
TGGAGGACCA GAAGGAGGAG GTGCAATTGC TAGTGTTCGG    1160
ATTGACTGCC AACTCTGACA CCCACCTGCT TCAGGGGCAG    1200
AGCCTGACCC TGACCTTGGA GAGCCCCCCT GGTAGTAGCC    1240
CCTCAGTGCA ATGTAGGAGT CCAAGGGGTA AAAACATACA    1280
GGGGGGGAAG ACCCTCTCCG TGTCTCAGCT GGAGCTCCAG    1320
GATAGTGGCA CCTGGACATG CACTGTCTTG CAGAACCAGA    1360
AGAAGGTGGA GTTCAAAATA GACATCGTGG TGCTAGCTTT    1400
CCAGAAGGCC TCCAGCATAG TCTATAAGAA AGAGGGGGAA    1440
CAGGTGGAGT TCTCCTTCCC ACTCGCCTTT ACAGTTGAAA    1480
AGCTGACGGG CAGTGGCGAG CTGTGGTGGC AGGCGGAGAG    1520
GGCTTCCTCC TCCAAGTCTT GGATCATCTT TGACCTGAAG    1560
AACAAGGAAG TGTCTGTAAA ACGGGTTACC CAGGACCCTA    1600
AGCTCCAGAT GGGCAAGAAG CTCCCGCTCC ACCTCACCCT    1640
GCCCCAGGCC TTGCCTCAGT ATGCTGGCTC TGGAAACCTC    1680
ACCCTGGCCC TTGAAGCGAA AACAGGAAAG TTGCATCAGG    1720
AAGTGAACCT GGTGGTGATG AGAGCCACTC AGCTCCAGAA    1760
AAATTTGACC TGTGAGGTGT GGGGACCCAC CTCCCCTAAG    1800
CTGATGCTGA GCTTGAAACT GGAGAACAAG GAGGCAAAGG    1840
TCTCGAAGCG GGAGAAGGCG GTGTGGGTGC TGAACCCTGA    1880
GGCGGGGATG TGGCAGTGTC TGCTGAGTGA CTCGGGACAG    1920
GTCCTGCTGG AATCCAACAT CAAGGTTCTG CCCATATGGT    1960
CCACCCCAGT GCAGCCAATG TTATTCATAA TGATAGTAGG    2000
AGGCTTGGTA GGTTTAAGAA TAGTTTTTGC TGTACTTTCT    2040
```

FIG. 23B

```
ATAGTGAATA GAGTTAGGCA GGGATATTCA CCATTATCGT          2080
TTCAGACCCA CCTCCCAATC CCGAGGGGAC CCGACAGGCC          2120
CGAAGGAATA GAAGAAGAAG GTGGAGAGAG AGACAGAGAC          2160
AGATCCATTC GATTAGTGAA CGGATCCTTA GCACTTATCT          2200
GGGACGATCT GCGGAGCCTG TGCCTCTTCA GCTACCACCG          2240
CTTGAGAGAC TTACTCTTGA TTGTAACGAG GATTGTGGAA          2280
CTTCTGGGAC GCAGGGGTG GGAAGCCCTC AAATATTGGT           2320
GGAATCTCCT ACAGTATTGG AGTCAGGAAC TAAAGAATAG          2360
TGCTGTTAAC TTGCTCAATG CCACAGCCAT AGCAGTAGCT          2400
GAGGGGACAG ATAGGGTTAT AGAAGTATTA CAAGCAGCTT          2440
ATAGAGCTAT TCGCCACATA CCTAGAAGAA TAAGACAGGG          2480
CTTGGAAAGG ATTTTGCTAT AAGCATATGG TACATTGCTG          2520
ATGAGTCCGT GAGGACGAAA CTGTGCTGCG GCCGCAGGAG          2560
CTTTGTTCCT TGGGTTCTTG GGAGCAGCAG GAAGCACTAT          2600
GGGCTGCACG TCAATGACGC TGACGGTACA GGCCAGACAA          2640
TTATTGTCTG ATATAGTGCA GCAGCAGAAC AATTTGCTGA          2680
GGGCTATTGA GGCGCAACAG CATCTGTTGC AACTCACAGT          2720
CTGGGGCATC AAACAGCTCC AGGCAAGAAT CCTGGCTGTG          2760
GAAAGATACC TAAAGGACAA CAGCTCCTGC GGCCGCTATA          2800
AGGTGGCAAG TGGTCAAAAA GTAGTGTGAT TGGATGGCCT          2840
GCTGTAAGGG AAAGAATGAG ACGAGCTGAG CCAGCAGCAG          2880
ATGGGGTGGG AGCAGTATCT CGAGCCATAA TACTGATGAG          2920
TCCGTGAGGA CGAAACTGTG ACGCGGCCGC CTCGAGGCGC          2960
GCGCATGCCT GCAGGTCGAC GTTAATTTCT GATGAGTCCG          3000
TGAGGACGAA ACACATGGTG CCATTTCTGA TGAGTCCGTG          3040
AGGACGAAAC AGCAGTGGGT CTTGCTGATG AGTCCGTGAG          3080
GACGAAACAA TTAATTTTGC TCCTGATGAG TCCGTGAGGA          3120
CGAAACTAAT GTGGATCCCA TACTGATGAG TCCGTGAGGA          3160
CGAAACTGAT TAAATCGCAA CTGATGAGTC CGTGAGGACG          3200
AAACCAGCCG TCCATGTGCT GATGAGTCCG TGAGGACGAA          3240
ACATTGTAGA GGGGCACTGA TGAGTCCGTG AGGACGAAAC          3280
ATTGCTACGG TACCTTTAAG ACCAATGACT TACAAGGCAG          3320
CTGTAGATCT TAGCCACTTT TTAAAAGAAA AGGGGGGACT          3360
GGAAGGGCTA ATTCACTCCC AAAGAAGACA AGATATCCTT          3400
GATCTGTGGA TCTACCACAC ACAAGGCTAC TTCCCTGATT          3440
GGCAGAACTA CACACCAGGG CCAGGGTCA GATATCCACT           3480
GACCTTTGGA TGGTGCTACA AGCTAGTACC AGTTGAGCCA          3520
GATAAGGTAG AAGAGGCCAA TAAAGGAGAG AACACCAGCT          3560
TGTTACACCC TGTGAGCCTG CATGGAATGG ATGACCCTGA          3600
GAGAGAAGTG TTAGAGTGGA GGTTTGACAG CCGCCTAGCA          3640
TTTCATCACG TGGCCCGAGA GCTGCATCCG GAGTACTTCA          3680
AGAACTGCTG ACATCGAGCT TGCTACAAGG GACTTTCCGC          3720
TGGGGACTTT CCAGGGAGGC GTGGCCTGGG CGGGACTGGG          3760
GAGTGGCGAG CCCTCAGATG CTGCATATAA GCAGCTGCTT          3800
TTTGCCTGTA CTGGGTCTCT CTGGTTAGAC CAGATCTGAG          3840
CCTGGGAGCT CTCTGGCTAA CTAGGGAACC CACTGCTTAA          3880
GCCTCAATAA AGCTTGCCTT GAGTGCTTCA AGTAGTGTGT          3920
GCCCGTCTGT TGTGTGACTC TGGTAACTAG AGATCCCTCA          3960
GACCCTTTTA GTCAGTGTGG AAAATCTCTA GCA                 3993
```

FIG. 24A

| | | | | |
|---|---|---|---|---|
| TGGAAGGGCT | AATTTGGTCC | CAAAAAAGAC | AAGAGATCCT | 40 |
| TGATCTGTGG | ATCTACCACA | CACAAGGCTA | CTTCCCTGAT | 80 |
| TGGCAGAACT | ACACACCAGG | GCCAGGGATC | AGATATCCAC | 120 |
| TGACCTTTGG | ATGGTGCTTC | AAGTTAGTAC | CAGTTGAACC | 160 |
| AGAGCAAGTA | GAAGAGGCCA | ATGAAGGAGA | GAACAACAGC | 200 |
| TTGTTACACC | CTATGAGCCA | GCATGGGATG | GAGGACCCGG | 240 |
| AGGGAGAAGT | ATTAGTGTGG | AAGTTTGACA | GCCTCCTAGC | 280 |
| ATTTCGTCAC | ATGGCCCGAG | AGCTGCATCC | GGAGTACTAC | 320 |
| AAAGACTGCT | GACATCGAGC | TTTCTACAAG | GGACTTTCCG | 360 |
| CTGGGGACTT | TCCAGGGAGG | TGTGGCCTGG | GCGGGACTGG | 400 |
| GGAGTGGCGA | GCCCTCAGAT | GCTACATATA | AGCAGCTGCT | 440 |
| TTTTGCCTGT | ACTGGGTCTC | TCTGGTTAGA | CCAGATCTGA | 480 |
| GCCTGGGAGC | TCTCTGGCTA | ACTAGGGAAC | CCACTGCTTA | 520 |
| AGCCTCAATA | AAGCTTGCCT | TGAGTGCTCA | AAGTAGTGTG | 560 |
| TGCCCGTCTG | TTGTGTGACT | CTGGTAACTA | GAGATCCCTC | 600 |
| AGACCCTTTT | AGTCAGTGTG | GAAAATCTCT | AGCAGTGGCG | 640 |
| CCCGAACAGG | GACTTGAAAG | CGAAAGTAAA | GCCAGAGGAG | 680 |
| ATCTCTCGAC | GCAGGACTCG | GCTTGCTGAA | GCGCGCACGG | 720 |
| CAAGAGGCGA | GGGGCGGCGA | CTGGTGAGTA | CGCCAAAAAT | 760 |
| TTTGACTAGC | GGAGGCTAGA | AGGAGATTGG | GTGCGAGAGC | 800 |
| GTCGGTATTA | AGCGGGGGAG | AATTAGATAA | ATGGGAAAAA | 840 |
| ATTCGGTAAT | AGGAGATGAA | CCGGGGAGTC | CCTTTTAGTC | 880 |
| ACTTGCTTCT | GGTGCTGCAA | CTGGCGCTCC | TCCCAGCAGC | 920 |
| CACTCAGGGA | AAGAAAGTGG | TGCTGGGCAA | AAAAGGGGAT | 960 |
| ACAGTGGAAC | TGACCTGTAC | AGCTTCCCAG | AAGAAGAGCA | 1000 |
| TACAATTCCA | CTGGAAAAAC | TCCAACCAGA | TAAAGATTCT | 1040 |
| GGGAAATCAG | GGCTCCTTCT | TAACTAAAGG | TCCATCCAAG | 1080 |
| CTGAATGATC | GCGCTGACTC | AAGAAGAAGC | CTTTGGGACC | 1120 |
| AAGGAAACTT | CCCCCTGATC | ATTAAGAATC | TTAAGATAGA | 1160 |
| AGACTCAGAT | ACTTACATCT | GTGAAGTGGA | GGACCAGAAG | 1200 |
| GAGGAGGTGC | AATTGCTAGT | GTTCGGATTG | ACTGCCAACT | 1240 |
| CTGACACCCA | CCTGCTTCAG | GGGCAGAGCC | TGACCCTGAC | 1280 |
| CTTGGAGAGC | CCCCCTGGTA | GTAGCCCCTC | AGTGCAATGT | 1320 |
| AGGAGTCCAA | GGGGTAAAAA | CATACAGGGG | GGGAAGACCC | 1360 |
| TCTCCGTGTC | TCAGCTGGAG | CTCCAGGATA | GTGGCACCTG | 1400 |
| GACATGCACT | GTCTTGCAGA | ACCAGAAGAA | GGTGGAGTTC | 1440 |
| AAAATAGACA | TCGTGGTGCT | AGCTTTCCAG | AAGGCCTCCA | 1480 |
| GCATAGTCTA | TAAGAAAGAG | GGGGAACAGG | TGGAGTTCTC | 1520 |
| CTTCCCACTC | GCCTTTACAG | TTGAAAAGCT | GACGGGCAGT | 1560 |
| GGCGAGCTGT | GGTGGCAGGC | GGAGAGGGCT | TCCTCCTCCA | 1600 |
| AGTCTTGGAT | CATCTTTGAC | CTGAAGAACA | AGGAAGTGTC | 1640 |
| TGTAAAACGG | GTTACCCAGG | ACCCTAAGCT | CCAGATGGGC | 1680 |
| AAGAAGCTCC | CGCTCCACCT | CACCCTGCCC | CAGGCCTTGC | 1720 |
| CTCAGTATGC | TGGCTCTGGA | AACCTCACCC | TGGCCCTTGA | 1760 |
| AGCGAAAACA | GGAAAGTTGC | ATCAGGAAGT | GAACCTGGTG | 1800 |
| GTGATGAGAG | CCACTCAGCT | CCAGAAAAAT | TTGACCTGTG | 1840 |
| AGGTGTGGGG | ACCCACCTCC | CCTAAGCTGA | TGCTGAGCTT | 1880 |
| GAAACTGGAG | AACAAGGAGG | CAAAGGTCTC | GAAGCGGGAG | 1920 |
| AAGGCGGTGT | GGGTGCTGAA | CCCTGAGGCG | GGGATGTGGC | 1960 |
| AGTGTCTGCT | GAGTGACTCG | GGACAGGTCC | TGCTGGAATC | 2000 |
| CAACATCAAG | GTTCTGCCCA | TATGGTCCAC | CCCAGTGCAG | 2040 |

FIG. 24B

```
CCAATGTTAT TCATAATGAT AGTAGGAGGC TTGGTAGGTT        2080
TAAGAATAGT TTTTGCTGTA CTTTCTATAG TGAATAGAGT        2120
TAGGCAGGGA TATTCACCAT TATCGTTTCA GACCCACCTC        2160
CCAATCCCGA GGGGACCCGA CAGGCCCGAA GGAATAGAAG        2200
AAGAAGGTGG AGAGAGAGAC AGAGACAGAT CCATTCGATT        2240
AGTGAACGGA TCCTTAGCAC TTATCTGGGA CGATCTGCGG        2280
AGCCTGTGCC TCTTCAGCTA CCACCGCTTG AGAGACTTAC        2320
TCTTGATTGT AACGAGGATT GTGGAACTTC TGGGACGCAG        2360
GGGGTGGGAA GCCCTCAAAT ATTGGTGGAA TCTCCTACAG        2400
TATTGGAGTC AGGAACTAAA GAATAGTGCT GTTAACTTGC        2440
TCAATGCCAC AGCCATAGCA GTAGCTGAGG GGACAGATAG        2480
GGTTATAGAA GTATTACAAG CAGCTTATAG AGCTATTCGC        2520
CACATACCTA GAAGAATAAG ACAGGGCTTG GAAAGGATTT        2560
TGCTATAAGC ATATGGTACA TTGCTGATGA GTCCGTGAGG        2600
ACGAAACTGT GCTGCGGCCG CAGGAGCTTT GTTCCTTGGG        2640
TTCTTGGGAG CAGCAGGAAG CACTATGGGC TGCACGTCAA        2680
TGACGCTGAC GGTACAGGCC AGACAATTAT TGTCTGATAT        2720
AGTGCAGCAG CAGAACAATT TGCTGAGGGC TATTGAGGCG        2760
CAACAGCATC TGTTGCAACT CACAGTCTGG GGCATCAAAC        2800
AGCTCCAGGC AAGAATCCTG GCTGTGGAAA GATACCTAAA        2840
GGACAACAGC TCCTGCGGCC GCTATAAGGT GGCAAGTGGT        2880
CAAAAAGTAG TGTGATTGGA TGGCCTGCTG TAAGGGAAAG        2920
AATGAGACGA GCTGAGCCAG CAGCAGATGG GGTGGGAGCA        2960
GTATCTCGAG CCATAATACT GATGAGTCCG TGAGGACGAA        3000
ACTGTGACGC GGCCGCCTCG AGGCGCGCGC ATGCCTGCAG        3040
GTCGACGTTA ATTTCTGATG AGTCCGTGAG GACGAAACAC        3080
ATGGTGCCAT TTCTGATGAG TCCGTGAGGA CGAAACAGCA        3120
GTGGGTCTTG CTGATGAGTC CGTGAGGACG AAACAATTAA        3160
TTTTGCTCCT GATGAGTCCG TGAGGACGAA ACTAATGTGG        3200
ATCCCATACT GATGAGTCCG TGAGGACGAA ACTGATTAAA        3240
TCGCAACTGA TGAGTCCGTG AGGACGAAAC CAGCCGTCCA        3280
TGTGCTGATG AGTCCGTGAG GACGAAACAT TGTAGAGGGG        3320
CACTGATGAG TCCGTGAGGA CGAAACATTG CTACGGTACC        3360
TTTAAGACCA ATGACTTACA AGGCAGCTGT AGATCTTAGC        3400
CACTTTTTAA AAGAAAAGGG GGGACTGGAA GGGCTAATTC        3440
ACTCCCAAAG AAGACAAGAT ATCCTTGATC TGTGGATCTA        3480
CCACACACAA GGCTACTTCC CTGATTGGCA GAACTACACA        3520
CCAGGGCCAG GGTCAGATA TCCACTGACC TTTGGATGGT         3560
GCTACAAGCT AGTACCAGTT GAGCCAGATA AGGTAGAAGA        3600
GGCCAATAAA GGAGAGAACA CCAGCTTGTT ACACCCTGTG        3640
AGCCTGCATG GAATGGATGA CCCTGAGAGA GAAGTGTTAG        3680
AGTGGAGGTT TGACAGCCGC CTAGCATTTC ATCACGTGGC        3720
CCGAGAGCTG CATCCGGAGT ACTTCAAGAA CTGCTGACAT        3760
CGAGCTTGCT ACAAGGGACT TTCCGCTGGG GACTTTCCAG        3800
GGAGGCGTGG CCTGGGCGGG ACTGGGGAGT GGCGAGCCCT        3840
CAGATGCTGC ATATAAGCAG CTGCTTTTTG CCTGTACTGG        3880
GTCTCTCTGG TTAGACCAGA TCTGAGCCTG GGAGCTCTCT        3920
GGCTAACTAG GGAACCCACT GCTTAAGCCT CAATAAAGCT        3960
TGCCTTGAGT GCTTCAAGTA GTGTGTGCCC GTCTGTTGTG        4000
TGACTCTGGT AACTAGAGAT CCCTCAGACC CTTTTAGTCA        4040
```

FIG. 24C

GTGTGGAAAA TCTCTAGCA                                            4059

FIG. 25A

| | | | | |
|---|---|---|---|---|
| TGGAAGGGCT | AATTTGGTCC | CAAAAAAGAC | AAGAGATCCT | 40 |
| TGATCTGTGG | ATCTACCACA | CACAAGGCTA | CTTCCCTGAT | 80 |
| TGGCAGAACT | ACACACCAGG | GCCAGGGATC | AGATATCCAC | 120 |
| TGACCTTTGG | ATGGTGCTTC | AAGTTAGTAC | CAGTTGAACC | 160 |
| AGAGCAAGTA | GAAGAGGCCA | ATGAAGGAGA | GAACAACAGC | 200 |
| TTGTTACACC | CTATGAGCCA | GCATGGGATG | GAGGACCCGG | 240 |
| AGGGAGAAGT | ATTAGTGTGG | AAGTTTGACA | GCCTCCTAGC | 280 |
| ATTTCGTCAC | ATGGCCCGAG | AGCTGCATCC | GGAGTACTAC | 320 |
| AAAGACTGCT | GACATCGAGC | TTTCTACAAG | GGACTTTCCG | 360 |
| CTGGGGACTT | TCCAGGGAGG | TGTGGCCTGG | GCGGGACTGG | 400 |
| GGAGTGGCGA | GCCCTCAGAT | GCTACATATA | AGCAGCTGCT | 440 |
| TTTTGCCTGT | ACTGGGTCTC | TCTGGTTAGA | CCAGATCTGA | 480 |
| GCCTGGGAGC | TCTCTGGCTA | ACTAGGGAAC | CCACTGCTTA | 520 |
| AGCCTCAATA | AAGCTTGCCT | TGAGTGCTCA | AGTAGTGTG | 560 |
| TGCCCGTCTG | TTGTGTGACT | CTGGTAACTA | GAGATCCCTC | 600 |
| AGACCCTTTT | AGTCAGTGTG | GAAAATCTCT | AGCAGTGGCG | 640 |
| CCCGAACAGG | GACTTGAAAG | CGAAAGTAAA | GCCAGAGGAG | 680 |
| ATCTCTCGAC | GCAGGACTCG | GCTTGCTGAA | GCGCGCACGG | 720 |
| CAAGAGGCGA | GGGGCGGCGA | CTGGTGAGTA | CGCCAAAAAT | 760 |
| TTTGACTAGC | GGAGGCTAGA | AGGAGATTGG | GTGCGAGAGC | 800 |
| GTCGGTATTA | AGCGGGGGAG | AATTAGATAA | ATGGGAAAAA | 840 |
| ATTCGGTTAA | GGCCAGGGGG | AAAGAAACAA | TATAAACTAA | 880 |
| AACATATAGT | ATGGGCAAGC | AGGGAGCTAG | AACGATTCGC | 920 |
| AGTTAATCCT | GGCCTTTTAG | AGACATGAGA | AGGCTGTAGA | 960 |
| CAAATACTGG | GACAGCTACA | ACCATCCCTT | CAGACAGGAT | 1000 |
| CAGAAGAACT | TAGATCATTA | TATAATACAA | TAGCAGTCCT | 1040 |
| CTATTGTGTG | CATCAAAGGA | TAGATGTAAA | AGACACCAAG | 1080 |
| GAAGCCTTAG | ATAAGATATA | GGAAGAGCAA | AACAAAAGTA | 1120 |
| AGAAAAAGGC | ACAGCAAGCA | GCAGCTGACA | CAGGAAACAA | 1160 |
| CAGCCAGGTC | AGCCAAAATT | ACCCTATAGT | GCAGAACCTC | 1200 |
| CAGGGGCAAA | TGGTACATTA | GGCCATATCA | CCTAGAACTT | 1240 |
| TAAATGCATG | GGTAAAAGTA | GTAGAAGAGA | AGGCTTTCAG | 1280 |
| CCCAGAAGTA | ATACCCATGT | TTTCAGCATT | ATCAGAAGGA | 1320 |
| GCCACCCCAC | AAGATTTAAA | TACCATGCTA | AACACAGTGG | 1360 |
| GGGGACATTA | AGCAGCCATG | CAAATGTTAA | AAGAGACCAT | 1400 |
| CAATGAGGAA | GCTGCAGAAT | AATAGGAGAT | GAACCGGGGA | 1440 |
| GTCCCTTTTA | GTCACTTGCT | TCTGGTGCTG | CAACTGGCGC | 1480 |
| TCCTCCCAGC | AGCCACTCAG | GGAAAGAAAG | TGGTGCTGGG | 1520 |
| CAAAAAAGGG | GATACAGTGG | AACTGACCTG | TACAGCTTCC | 1560 |
| CAGAAGAAGA | GCATACAATT | CCACTGGAAA | AACTCCAACC | 1600 |
| AGATAAAGAT | TCTGGGAAAT | CAGGGCTCCT | TCTTAACTAA | 1640 |
| AGGTCCATCC | AAGCTGAATG | ATCGCGCTGA | CTCAAGAAGA | 1680 |
| AGCCTTTGGG | ACCAAGGAAA | CTTCCCCCTG | ATCATTAAGA | 1720 |
| ATCTTAAGAT | AGAAGACTCA | GATACTTACA | TCTGTGAAGT | 1760 |
| GGAGGACCAG | AAGGAGGAGG | TGCAATTGCT | AGTGTTCGGA | 1800 |
| TTGACTGCCA | ACTCTGACAC | CCACCTGCTT | CAGGGGCAGA | 1840 |
| GCCTGACCCT | GACCTTGGAG | AGCCCCCTG | GTAGTAGCCC | 1880 |
| CTCAGTGCAA | TGTAGGAGTC | CAAGGGGTAA | AAACATACAG | 1920 |
| GGGGGGAAGA | CCCTCTCCGT | GTCTCAGCTG | GAGCTCCAGG | 1960 |
| ATAGTGGCAC | CTGGACATGC | ACTGTCTTGC | AGAACCAGAA | 2000 |
| GAAGGTGGAG | TTCAAAATAG | ACATCGTGGT | GCTAGCTTTC | 2040 |

FIG. 25B

```
CAGAAGGCCT CCAGCATAGT CTATAAGAAA GAGGGGGAAC        2080
AGGTGGAGTT CTCCTTCCCA CTCGCCTTTA CAGTTGAAAA        2120
GCTGACGGGC AGTGGCGAGC TGTGGTGGCA GGCGGAGAGG        2160
GCTTCCTCCT CCAAGTCTTG GATCATCTTT GACCTGAAGA        2200
ACAAGGAAGT GTCTGTAAAA CGGGTTACCC AGGACCCTAA        2240
GCTCCAGATG GGCAAGAAGC TCCCGCTCCA CCTCACCCTG        2280
CCCCAGGCCT TGCCTCAGTA TGCTGGCTCT GGAAACCTCA        2320
CCCTGGCCCT TGAAGCGAAA ACAGGAAAGT TGCATCAGGA        2360
AGTGAACCTG GTGGTGATGA GAGCCACTCA GCTCCAGAAA        2400
AATTTGACCT GTGAGGTGTG GGACCCACC TCCCCTAAGC         2440
TGATGCTGAG CTTGAAACTG GAGAACAAGG AGGCAAAGGT        2480
CTCGAAGCGG GAGAAGGCGG TGTGGGTGCT GAACCCTGAG        2520
GCGGGGATGT GGCAGTGTCT GCTGAGTGAC TCGGACAGG         2560
TCCTGCTGGA ATCCAACATC AAGGTTCTGC CCATATGGTC        2600
CACCCCAGTG CAGCCAATGT TATTCATAAT GATAGTAGGA        2640
GGCTTGGTAG GTTTAAGAAT AGTTTTTGCT GTACTTTCTA        2680
TAGTGAATAG AGTTAGGCAG GGATATTCAC CATTATCGTT        2720
TCAGACCCAC CTCCCAATCC CGAGGGGACC CGACAGGCCC        2760
GAAGGAATAG AAGAAGAAGG TGGAGAGAGA GACAGAGACA        2800
GATCCATTCG ATTAGTGAAC GGATCCTTAG CACTTATCTG        2840
GGACGATCTG CGGAGCCTGT GCCTCTTCAG CTACCACGC         2880
TTGAGAGACT TACTCTTGAT TGTAACGAGG ATTGTGGAAC        2920
TTCTGGGACG CAGGGGGTGG GAAGCCCTCA AATATTGGTG        2960
GAATCTCCTA CAGTATTGGA GTCAGGAACT AAAGAATAGT        3000
GCTGTTAACT TGCTCAATGC CACAGCCATA GCAGTAGCTG        3040
AGGGACAGA TAGGGTTATA GAAGTATTAC AAGCAGCTTA         3080
TAGAGCTATT CGCCACATAC CTAGAAGAAT AAGACAGGGC        3120
TTGGAAAGGA TTTTGCTATA AGCATATGGT ACATTGCTGA        3160
TGAGTCCGTG AGGACGAAAC TGTGCTGCGG CCGCAGGAGC        3200
TTTGTTCCTT GGGTTCTTGG GAGCAGCAGG AAGCACTATG        3240
GGCTGCACGT CAATGACGCT GACGGTACAG GCCAGACAAT        3280
TATTGTCTGA TATAGTGCAG CAGCAGAACA ATTTGCTGAG        3320
GGCTATTGAG GCGCAACAGC ATCTGTTGCA ACTCACAGTC        3360
TGGGGCATCA AACAGCTCCA GGCAAGAATC CTGGCTGTGG        3400
AAAGATACCT AAAGGACAAC AGCTCCTGCG GCCGCTATAA        3440
GGTGGCAAGT GGTCAAAAAG TAGTGTGATT GGATGGCCTG        3480
CTGTAAGGGA AAGAATGAGA CGAGCTGAGC CAGCAGCAGA        3520
TGGGGTGGGA GCAGTATCTC GAGCCATAAT ACTGATGAGT        3560
CCGTGAGGAC GAAACTGTGA CGCGGCCGCC TCGAGGCGCG        3600
CGCATGCCTG CAGGTCGACG TTAATTTCTG ATGAGTCCGT        3640
GAGGACGAAA CACATGGTGC CATTTCTGAT GAGTCCGTGA        3680
GGACGAAACA GCAGTGGGTC TTGCTGATGA GTCCGTGAGG        3720
ACGAAACAAT TAATTTTGCT CCTGATGAGT CCGTGAGGAC        3760
GAAACTAATG TGGATCCCAT ACTGATGAGT CCGTGAGGAC        3800
GAAACTGATT AAATCGCAAC TGATGAGTCC GTGAGGACGA        3840
AACCAGCCGT CCATGTGCTG ATGAGTCCGT GAGGACGAAA        3880
CATTGTAGAG GGGCACTGAT GAGTCCGTGA GGACGAAACA        3920
TTGCTACGGT ACCTTTAAGA CCAATGACTT ACAAGGCAGC        3960
TGTAGATCTT AGCCACTTTT TAAAAGAAAA GGGGGGACTG        4000
GAAGGGCTAA TTCACTCCCA AGAAGACAA GATATCCTTG         4040
```

FIG. 25C

```
ATCTGTGGAT CTACCACACA CAAGGCTACT TCCCTGATTG        4080
GCAGAACTAC ACACCAGGGC CAGGGGTCAG ATATCCACTG        4120
ACCTTTGGAT GGTGCTACAA GCTAGTACCA GTTGAGCCAG        4160
ATAAGGTAGA AGAGGCCAAT AAAGGAGAGA ACACCAGCTT        4200
GTTACACCCT GTGAGCCTGC ATGGAATGGA TGACCCTGAG        4240
AGAGAAGTGT TAGAGTGGAG GTTTGACAGC CGCCTAGCAT        4280
TTCATCACGT GGCCCGAGAG CTGCATCCGG AGTACTTCAA        4320
GAACTGCTGA CATCGAGCTT GCTACAAGGG ACTTTCCGCT        4360
GGGGACTTTC CAGGGAGGCG TGGCCTGGGC GGGACTGGGG        4400
AGTGGCGAGC CCTCAGATGC TGCATATAAG CAGCTGCTTT        4440
TTGCCTGTAC TGGGTCTCTC TGGTTAGACC AGATCTGAGC        4480
CTGGGAGCTC TCTGGCTAAC TAGGGAACCC ACTGCTTAAG        4520
CCTCAATAAA GCTTGCCTTG AGTGCTTCAA GTAGTGTGTG        4560
CCCGTCTGTT GTGTGACTCT GGTAACTAGA GATCCCTCAG        4600
ACCCTTTTAG TCAGTGTGGA AAATCTCTAG CA                4632
```

FIG. 26A

```
TGGAAGGGCT AATTTGGTCC CAAAAAAGAC AAGAGATCCT        40
TGATCTGTGG ATCTACCACA CACAAGGCTA CTTCCCTGAT        80
TGGCAGAACT ACACACCAGG GCCAGGGATC AGATATCCAC       120
TGACCTTTGG ATGGTGCTTC AAGTTAGTAC CAGTTGAACC       160
AGAGCAAGTA GAAGAGGCCA AATAAGGAGA GAAGAACAGC       200
TTGTTACACC CTATGAGCCA GCATGGGATG GAGGACCCGG       240
AGGGAGAAGT ATTAGTGTGG AAGTTTGACA GCCTCCTAGC       280
ATTTCGTCAC ATGGCCCGAG AGCTGCATCC GGAGTACTAC       320
AAAGACTGCT GACATCGAGC TTTCTACAAG GGACTTTCCG       360
CTGGGGACTT TCCAGGGAGG TGTGGCCTGG GCGGGACTGG       400
GGAGTGGCGA GCCCTCAGAT GCTACATATA AGCAGCTGCT       440
TTTTGCCTGT ACTGGGTCTC TCTGGTTAGA CCAGATCTGA       480
GCCTGGGAGC TCTCTGGCTA ACTAGGGAAC CCACTGCTTA       520
AGCCTCAATA AAGCTTGCCT TGAGTGCTCA AAGTAGTGTG       560
TGCCCGTCTG TTGTGTGACT CTGGTAACTA GAGATCCCTC       600
AGACCCTTTT AGTCAGTGTG GAAAATCTCT AGCAGTGGCG       640
CCCGAACAGG GACTTGAAAG CGAAAGTAAA GCCAGAGGAG       680
ATCTCTCGAC GCAGGACTCG GCTTGCTGAA GCGCGCACGG       720
CAAGAGGCGA GGGGCGGCGA CTGGTGAGAG ATGGGTGCGA       760
GAGCGTCGGT ATTAAGCGGG GGAGAATTAG ATAAATGGGA       800
AAAAATTCGG TTAAGGCCAG GGGGAAAGAA ACAATATAAA       840
CTAAAACATA TAGTATGGGC AAGCAGGGAG CTAGAACGAT       880
TCGCAGTTAA TCCTGGCCTT TTAGAGACAT CAGAAGGCTG       920
TAGACAAATA CTGGGACAGC TACAACCATC CCTTCAGACA       960
GGATCAGAAG AACTTAGATC ATTATATAAT ACAATAGCAG      1000
TCCTCTATTG TGTGCATCAA AGGATAGATG TAAAAGACAC      1040
CAAGGAAGCC TTAGATAAGA TAGAGGAAGA GCAAAACAAA      1080
AGTAAGAAAA AGGCACAGCA AGCAGCAGCT GACACAGGAA      1120
ACAACAGCCA GGTCAGCCAA AATTACCCTA TAGTGCAGAA      1160
CCTCCAGGGG CAAATGGTAC ATCAGGCCAT ATCACCTAGA      1200
ACTTTAAATG CATGGGTAAA AGTAGTAGAA GAGAAGGCTT      1240
TCAGCCCAGA AGTAATACCC ATGTTTTCAG CATTATCAGA      1280
AGGAGCCACC CCACAAGATT TAAATACCAT GCTAAACACA      1320
GTGGGGGGAC ATCAAGCAGC CATGCAAATG TTAAAAGAGA      1360
CCATCAATGA GGAAGCTGCA GAATGGGATA GATTGCATCC      1400
AGTGCATGCA GGGCCTATTG CACCAGGCCA GATGAGAGAA      1440
CCAAGGGGAA GTGACATAGC AGGAACTACT AGTACCCTTC      1480
AGGAACAAAT AGGATGGATG ACACATAATC CACCTATCCC      1520
AGTAGGAGAA ATCTATAAAA GATGGATAAT CCTGGGATTA      1560
AATAAAATAG TAAGAATGTA TAGCCCTACC AGCATTCTGG      1600
ACATAAGACA AGGACCAAAG GAACCCTTTA GAGACTATGT      1640
AGACCGATTC TATAAAACTC TAAGAGCCGA GCAAGCTTCA      1680
CAAGAGGTAA AAAATTGGAT GACAGAAACC TTGTTGGTCC      1720
AAAATGCGAA CCCAGATTGT AAGACTATTT TAAAAGCATT      1760
GGGACCAGGA GCGACACTAG AAGAAATGAT GACAGCATGT      1800
CAGGGAGTGG GGGGACCCGG CCATAAAGCA AGAGTTTTGG      1840
CTGAAGCAAT GAGCCAAGTA ACAAATCCAG CTACCATAAT      1880
GATACAGAAA GGCAATTTTA GGAACCAAAG AAAGACTGTT      1920
AAGTGTTTCA ATTGTGGCAA AGAAGGGCAC ATAGCCAAAA      1960
ATTGCAGGGC CCCTAGGAAA AAGGGCTGTT GGAAATGTGG      2000
AAAGGAAGGA CACCAAATGA AAGATTGTAC TGAGAGACAG      2040
```

FIG. 26B

```
GCTAATTTTT TAGGGAAGAT CTGGCCTTCC CACAAGGGAA      2080
GGCCAGGGAA TTTTCTTCAG AGCAGACCAG AGCCAACAGC      2120
CCCACCAGAA GAGAGCTTCA GGTTTGGGGA AGAGACAACA      2160
ACTCCCTCTC AGAAGCAGGA GCCGATAGAC AAGGAACTGT      2200
ATCCTTTAGC TTCCCTCAGA TCACTCTTTG GCAGCGACCC      2240
CTCGTCACAA TAAAGATAGG GGGCAATTA AAGGAAGCTC       2280
TATTAGATAC AGGAGCAGAT GATACAGTAT TAGAAGAAAT      2320
GAATTTGCCA GGAAGATGGA AACCAAAAAT GATAGGGGGA      2360
ATTGGAGGTT TTATCAAAGT AGGACAGTAT GATCAGATAC      2400
TCATAGAAAT CTGCGGACAT AAAGCTATAG GTACAGTATT      2440
AGTAGGACCT ACACCTGTCA ACATAATTGG AAGAAATCTG      2480
TTGACTCAGA TTGGCTGCAC TTTAAATTTT CCCATTAGTC      2520
CTATTGAGAC TGTACCAGTA AAATTAAAGC CAGGAATGGA      2560
TGGCCCAAAA GTTAAACAAT GGCCATTGAC AGAAGAAAAA      2600
ATAAAAGCAT TAGTAGAAAT TTGTACAGAA ATGGAAAAGG      2640
AAGGAAAAAT TCAAAAATT GGGCCTGAAA ATCCATACAA       2680
TACTCCAGTA TTTGCCATAA AGAAAAAGA CAGTACTAAA       2720
TGGAGAAAAT TAGTAGATTT CAGAGAACTT AATAAGAGAA      2760
CTCAAGATTT CTGGGAAGTT CAATTAGGAA TACCACATCC      2800
TGCAGGGTTA AAACAGAAAA AATCAGTAAC AGTACTGGAT      2840
GTGGGCGATG CATATTTTTC AGTTCCCTTA GATAAAGACT      2880
TCAGGAAGTA TACTGCATTT ACCATACCTA GTATAAACAA      2920
TGAGACACCA GGGATTAGAT ATCAGTACAA TGTGCTTCCA      2960
CAGGGATGGA AAGGATCACC AGCAATATTC CAGTGTAGCA      3000
TGACAAAAAT CTTAGAGCCT TTTAGAAAAC AAAATCCAGA      3040
CATAGTCATC TATCAATACA TGGATGATTT GTATGTAGGA      3080
TCTGACTTAG AAATAGGGCA GCATAGAACA AAAATAGAGG      3120
AACTGAGACA ACATCTGTTG AGGTGGGGAT TTACCACACC      3160
AGACAAAAAA CATCAGAAAG AACCTCCATT CCTTTGGATG      3200
GGTTATGAAC TCCATCCTGA TAAATGGACA GTACAGCCTA      3240
TAGTGCTGCC AGAAAAGGAC AGCTGGACTG TCAATGACAT      3280
ACAGAAATTA GTGGGAAAAT TGAATTGGGC AAGTCAGATT      3320
TATGCAGGGA TTAAAGTAAG GCAATTATGT AAACTTCTTA      3360
GGGGAACCAA AGCACTAACA GAAGTAGTAC CACTAACAGA      3400
AGAAGCAGAG CTAGAACTGG CAGAAAACAG GGAGATTCTA      3440
AAAGAACCGG TACATGGAGT GTATTATGAC CCATCAAAAG      3480
ACTTAATAGC AGAAATACAG AAGCAGGGGC AAGGCCAATG      3520
GACATATCAA ATTTATCAAG AGCCATTTAA AAATCTGAAA      3560
ACAGGAAAAT ATGCAAGAAT GAAGGGTGCC CACACTAATG      3600
ATGTGAAACA ATTAACAGAG GCAGTACAAA AAATAGCCAC      3640
AGAAAGCATA GTAATATGGG GAAAGACTCC TAAATTTAAA      3680
TTACCCATAC AAAAGGAAAC ATGGGAAGCA TGGTGGACAG      3720
AGTATTGGCA AGCCACCTGG ATTCCTGAGT GGGAGTTTGT      3760
CAATACCCCT CCCTTAGTGA AGTTATGGTA CCAGTTAGAG      3800
AAAGAACCCA TAATAGGAGC AGAAACTTTC TATGTAGATG      3840
GGGCAGCCAA TAGGGAAACT AAATTAGGAA AAGCAGGATA      3880
TGTAACTGAC AGAGGAAGAC AAAAAGTTGT CCCCCTAACG      3920
GACACAACAA ATCAGAAGAC TGAGTTACAA GCAATTCATC      3960
TAGCTTTGCA GGATTCGGGA TTAGAAGTAA ACATAGTGAC      4000
AGACTCACAA TATGCATTGG GAATCATTCA AGCACAACCA      4040
```

FIG. 26C

```
GATAAGAGTG AATCAGAGTT AGTCAGTCAA ATAATAGAGC        4080
AGTTAATAAA AAAGGAAAAA GTCTACCTGG CATGGGTACC        4120
AGCACACAAA GGAATTGGAG GAAATGAACA AGTAGATGGG        4160
TTGGTCAGTG CTGGAATCAG GAAAGTACTA TTTTTAGATG        4200
GAATAGATAA GGCCCAAGAA GAACATGAGA AATATCACAG        4240
TAATTGGAGA GCAATGGCTA GTGATTTTAA CCTACCACCT        4280
GTAGTAGCAA AAGAAATAGT AGCCAGCTGT GATAAATGTC        4320
AGCTAAAAGG GGAAGCCATG CATGGACAAG TAGACTGTAG        4360
CCCAGGAATA TGGCAGCTAG ATTGTACACA TTTAGAAGGA        4400
AAAGTTATCT TGGTAGCAGT TCATGTAGCC AGTGGATATA        4440
TAGAAGCAGA AGTAATTCCA GCAGAGACAG GGCAAGAAAC        4480
AGCATACTTC CTCTTAAAAT TAGCAGGAAG ATGGCCAGTA        4520
AAAACAGTAC ATACAGACAA TGGCAGCAAT TTCACCAGTA        4560
CTACAGTTAA GGCCGCCTGT TGGTGGGCGG GGATCAAGCA        4600
GGAATTTGGC ATTCCCTACA ATCCCCAAAG TCAAGGAGTA        4640
ATAGAATCTA TGAATAAAGA ATTAAAGAAA ATTATAGGAC        4680
AGGTAAGAGA TCAGGCTGAA CATCTTAAGA CAGCAGTACA        4720
AATGGCAGTA TTCATCCACA ATTTTAAAAG AAAAGGGGGG        4760
ATTGGGGGGT ACAGTGCAGG GGAAAGAATA GTAGACATAA        4800
TAGCAACAGA CATACAAACT AAAGAATTAC AAAAACAAAT        4840
TACAAAAATT CAAAATTTTC GGGTTTATTA CAGGGACAGC        4880
AGAGATCCAG TTTGGAAAGG ACCAGCAAAG CTCCTCTGGA        4920
AAGGTGAAGG GGCAGTAGTA ATACAAGATA ATAGTGACAT        4960
AAAAGTAGTG CCAAGAAGAA AAGCAAAGAT CATCAGGGAT        5000
TATGGAAAAC AGATGGCAGG TGATGATTGT GTGGCAAGTA        5040
GACAGGATGA GGATTAACAC ATGGAAAAGA TTAGTAAAAC        5080
ACCATATGTA TATTTCAAGG AAAGCTAAGG ACTGGTTTTA        5120
TAGACATCAC TATGAAAGTA CTAATCCAAA AATAAGTTCA        5160
GAAGTACACA TCCCACTAGG GGATGCTAAA TTAGTAATAA        5200
CAACATATTG GGGTCTGCAT ACAGGAGAAA GAGACTGGCA        5240
TTTGGGTCAG GGAGTCTCCA TAGAATGGAG GAAAAAGAGA        5280
TATAGCACAC AAGTAGACCC TGACCTAGCA GACCAACTAA        5320
TTCATCTGCA CTATTTTGAT TGTTTTTCAG AATCTGCTAT        5360
AAGAAATACC ATATTAGGAC GTATAGTTAG TCCTAGGTGT        5400
GAATATCAAG CAGGACATAA CAAGGTAGGA TCTCTACAGT        5440
ACTTGGCACT AGCAGCATTA ATAAAACCAA AACAGATAAA        5480
GCCACCTTTG CCTAGTGTTA GGAAACTGAC AGAGGACAGA        5520
TGGAACAAGC CCCAGAAGAC CAAGGGCCAC AGAGGGAGCC        5560
ATACAATGAA TGGACACTAG AGCTTTTAGA GGAACTTAAG        5600
AGTGAAGCTG TTAGACATTT TCCTAGGATA TGGCTCCATA        5640
ACTTAGGACA ACATATCTAT GAAACTTACG GGGATACTTG        5680
GGCAGGAGTG GAAGCCATAA TAAGAATTCT GCAACAACTG        5720
CTGTTTATCC ATTTCAGAAT TGGGTGTCGA CATAGCAGAA        5760
TAGGCGTTAC TCGACAGAGG AGAGCAAGAA ATGGAGCCAG        5800
TAGATCCTAG ACTAGAGCCC TGGAAGCATC CAGGAAGTCA        5840
GCCTAAAACT GCTTGTACCA ATTGCTATTG TAAAAAGTGT        5880
TGCTTTCATT GCCAAGTTTG TTTCATGACA AAAGCCTTAG        5920
GCATCTCCTA TGGCAGGAAG AAGCGGAGAC AGCGACGAAG        5960
AGCTCATCAG AACAGTCAGA CTCATCAAGC TTCTCTATCA        6000
AAGCAGTAAG TAGTACATGT AATGCAACCT ATAATAGTAG        6040
```

FIG. 26D

```
CAATAGTAGC ATTAGTAGTA GCAATAATAA TAGCAATAGT         6080
TGTGTGGTCC ATAGTAATCA TAGAATATAG GAAAATATTA         6120
AGACAAAGAA AAATAGACAG GTTAATTGAT AGACTAATAG         6160
AAAGAGCAGA AGACAGTGGC AATGAGAGTG AAGGAGAAGT         6200
ATCAGCACTT GTGGAGATGG GGGTGGAAAT GGGGCACCAT         6240
GCTCCTTGGG ATATTGATGA TCTGTAGAAT AGGAGCTTTG         6280
TTCCTTGGGT TCTTGGGAGC AGCAGGAAGC ACTATGGGCT         6320
GCACGTCAAT GACGCTGACG GTACAGGCCA GACAATTATT         6360
GTCTGATATA GTGCAGCAGC AGAACAATTT GCTGAGGGCT         6400
ATTGAGGCGC AACAGCATCT GTTGCAACTC ACAGTCTGGG         6440
GCATCAAACA GCTCCAGGCA AGAATCCTGG CTGTGGAAAG         6480
ATACCTAAAG GATCAACAGC TCCTGGGGAT TTGGGGTTGC         6520
TCTGGAAAAC TCATTTGCAC CACTGCTGTG CCTTGGAATG         6560
CTAGTTGGAG TAATAAATCT CTGGAACAGA TTTGGAATAA         6600
CATGACCTGG ATGGAGTGGG ACAGAGAAAT TAACAATTAC         6640
ACAAGCTTAA TACACTCCTT AATTGAAGAA TCGCAAAACC         6680
AGCAAGAAAA GAATGAACAA GAATTATTGG AATTAGATAA         6720
ATGGGCAAGT TTGTGGAATT GGTTTAACAT AACAAATTGG         6760
CTGTGGTATA TAAAATTATT CATAATGATA GTAGGAGGCT         6800
TGGTAGGTTT AAGAATAGTT TTTGCTGTAC TTTCTATAGT         6840
GAATAGAGTT AGGCAGGGAT ATTCACCATT ATCGTTTCAG         6880
ACCCACCTCC CAATCCCGAG GGGACCCGAC AGGCCCGAAG         6920
GAATAGAAGA AGAAGGTGGA GAGAGAGACA GAGACAGATC         6960
CATTCGATTA GTGAACGGAT CCTTAGCACT TATCTGGGAC         7000
GATCTGCGGA GCCTGTGCCT CTTCAGCTAC CACCGCTTGA         7040
GAGACTTACT CTTGATTGTA ACGAGGATTG TGGAACTTCT         7080
GGGACGCAGG GGGTGGGAAG CCCTCAAATA TTGGTGGAAT         7120
CTCCTACAGT ATTGGAGTCA GGAACTAAAG AATAGTGCTG         7160
TTAACATAAG ATACATTGAT GAGTTTGGAC AAACCACAAC         7200
TAGAATGCAG TGAAAAAAAT GCTTTATTTG TGAAATTTGT         7240
GATGCTATTG CTTTATTTGT AACCATTATA AGCTGCAATA         7280
AACAAGTTAA CAACAACAAT TGCATTCATT TTATGTTTCA         7320
GGTTCAGGGG GAGGTGTGGG AGGTTTTTTA AAGCAAGTAA         7360
AACCTCTACA AATGTGGTAT GGCTGATTAT GATGCTAGC          7399
```

FIG. 27

```
AAGCTTCATA TGCCATAATA CTGATGAGTC CGTGAGGACG        40
AAACTGTGAC GCGGCCGCCT CGAG                         64
```

FIG. 28

```
AAGCTTCATA TGGTACATTG CTGATGAGTC CGTGAGGACG         40
AAACTGTGCT GCGGCCGCCT CGAG                          64
```

FIG. 29

```
AAGCTTCATA TGCCATAATA CTGATGAGTC CGTGAGGACG        40
AAACTGTGAC GCGGCCGCCT CGAGGCGCGC GCATGCCTGC        80
AGGTCGACGT TAATTTCTGA TGAGTCCGTG AGGACGAAAC       120
ACATGGTGCC ATTTCTGATG AGTCCGTGAG GACGAAACAG       160
CAGTGGGTCT TGCTGATGAG TCCGTGAGGA CGAAACAATT       200
AATTTTGCTC CTGATGAGTC CGTGAGGACG AAACTAATGT       240
GGATCCCATA CTGATGAGTC CGTGAGGACG AAACTGATTA       280
AATCGCAACT GATGAGTCCG TGAGGACGAA ACCAGCCGTC       320
CATGTGCTGA TGAGTCCGTG AGGACGAAAC ATTGTAGAGG       360
GGCACTGATG AGTCCGTGAG GACGAAACAT TGCTACTAGT       400
ACGCGAATTC                                        410
```

FIG. 30

```
AAGCTTCATA TGGTACATTG CTGATGAGTC CGTGAGGACG    40
AAACTGTGCT GCGGCCGCCT CGAGGCGCGC GCATGCCTGC    80
AGGTCGACTC TAGAGGATCC CATACTGATG AGTCCGTGAG   120
GACGAAACTG ATTAAATCGC AACTGATGAG TCCGTGAGGA   160
CGAAACCAGC CGTCCATGTG CTGATGAGTC CGTGAGGACG   200
AAACATTGTA GAGGGCACT GATGAGTCCG TGAGGACGAA   240
ACATTGCTAC TAGTACGCGA ATTC                    264
```

FIG. 31

```
AAGCTTCATA  TGCCATAATA  CTGATGAGTC  CGTGAGGACG              40
AAACTGTGAC  GCGGCCGCCT  CGAGGCGCGC  GCATGCCTGC              80
AGGTCGACTC  TAGAGGATCC  CATACTGATG  AGTCCGTGAG             120
GACGAAACTG  ATTAAATCGC  AACTGATGAG  TCCGTGAGGA             160
CGAAACCAGC  CGTCCATGTG  CTGATGAGTC  CGTGAGGACG             200
AAACATTGTA  GAGGGCACT   GATGAGTCCG  TGAGGACGAA             240
ACATTGCTAC  TAGTACGCGA  ATTC                               264
```

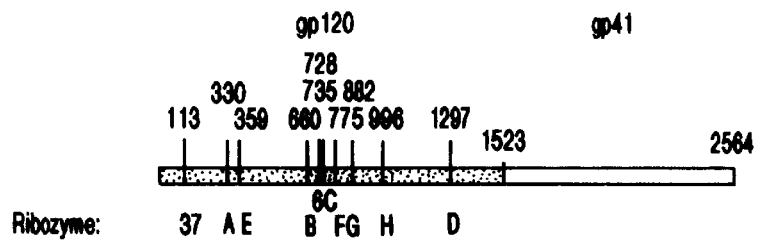
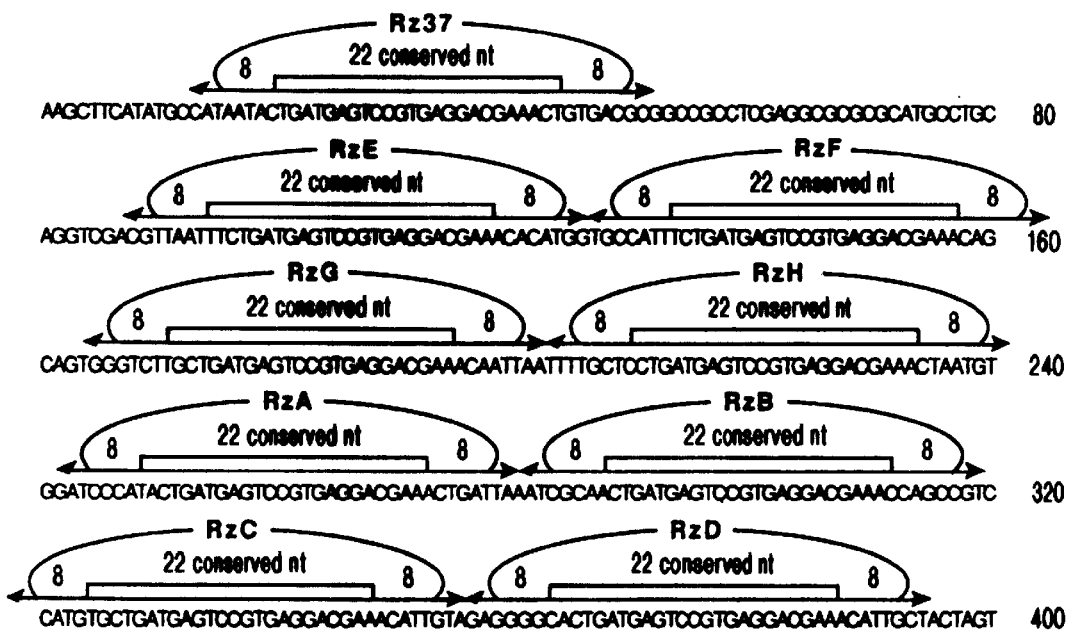
FIG. 32 pNL4-3         pNL4-3 + HD4         pNL4-3 + HD4 deletion

| Transfected Cells | DNAs [a] | p24 (pg/ml) [b] | p24 (%) [c] | Syncytia [d] |
|---|---|---|---|---|
| 1. HeLa | pNL4-3 | 855 | 100 | - |
| | pNL4-3 + HD1 | 521 | 61 | - |
| | pNL4-3 + HD2 | 444 | 52 | - |
| | pNL4-3 + HD3 | 351 | 41 | - |
| 2. HeLa T4 | pNL4-3 | 177,308 | 100 | ++++ |
| | pNL4-3 + HD1 | 24,420 | 14 | + |
| | pNL4-3 + HD2 | 6,871 | 4 | + |
| | pNL4-3 + HD3 | 12,348 | 7 | + |
| 3. HeLa T4 | pNL4-3 | 41,080 | 100 | ++++ |
| | pNL4-3 + HD1 deletion | 20,560 | 50 | ++++ |
| | pNL4-3 + HD3 deletion | 20,840 | 51 | ++++ |
| 4. HeLa T4 | pNL4-3 | 111,608 | 100 | ++++ |
| | pNL4-3 + HD4 | 4,248 | 4 | + |
| | pNL4-3 + HD4 deletion | 8,086 | 7 | + |

FIG. 39

Effect of Nucleotide Changes in HIV-1 env Target Regions on Multitarget-Ribozyme Activity

| | Virus Isolate | Rz37 | RzA | RzE | RzB | Rz6 | RzC | RzF | RzG | RzH | RzD | Conserved |
|---|---|---|---|---|---|---|---|---|---|---|---|---|
| | HIVNL43 | - | - | - | - | - | - | - | - | - | - | 10 |
| | HIVLAI | - | - | - | - | - | - | 1 | - | - | - | 9 |
| | HIVJH3 | - | - | - | - | - | - | - | - | ▨2▨ | - | 9 |
| | HIVSC | - | - | - | ▨5▨ | - | - | 1 | 1 | - | - | 7 |
| | HIVALA1 | - | - | - | - | - | - | - | - | - | - | 10 |
| | HIVBRVA | - | - | - | - | - | - | 1 | - | 2 | - | 8 |
| | HIVMFA | - | - | - | - | - | - | - | - | - | - | 10 |
| | HIVMN | - | - | - | - | - | - | - | - | - | - | 10 |
| North America | HIVADA | (1) | - | - | - | - | - | - | - | 1 | - | 8 |
| | HIVJRFL | - | - | - | - | - | - | ▨1▨ | - | - | - | 9 |
| | JRCSF | - | ▨1▨ | - | - | - | - | ▨1▨ | 1 | 1 | 1 | 5 |
| | HIVBAL1 | - | - | - | - | - | - | - | - | 1 | - | 9 |
| | HIVHXB2 | - | - | - | - | - | - | - | - | - | - | 10 |
| | WMJ22 | - | - | - | - | - | - | - | - | - | - | 10 |
| | HIVJFL | - | - | - | - | - | - | 2 | - | 3 | - | 8 |
| | HIVRF | - | - | - | - | - | - | - | - | 2 | - | 9 |
| | HIVNY5 | - | - | - | - | 1 | - | 1 | - | ▨1▨ | - | 7 |
| | SF162 | - | - | 1 | - | - | - | - | - | ▨2▨ | - | 8 |
| | HIVSF2 | (1) | - | - | - | - | - | - | 1 | 1 | - | 7 |
| | HIVHAN | - | - | - | 1 | 1 | 1 | - | - | 1 | - | 6 |
| | HIVSF33 | (1) | 1 | - | - | - | - | - | - | - | - | 8 |
| | CDC42 | - | ▨1▨ | 1 | 3 | - | - | - | - | 1 | 1 | 5 |
| | HIVOYI | - | - | - | - | - | - | - | - | 2 | - | 9 |
| | HIVELI | (1) | - | - | 1 | - | - | ▨4▨ | - | ▨2▨ | ▨2▨ | 5 |
| | HIVZ2Z6 | ▨1▨ | - | - | 2 | - | - | - | 2 | ▨6▨ | - | 6 |
| Africa | HIVNDK | (1) | - | - | 2 | - | - | - | 1 | ▨3▨ | - | 6 |
| | HIVJY1 | (1) | - | - | 2 | 1 | - | ▨2▨ | 1 | ▨5▨ | 1 | 3 |
| | HIVU455 | 2 | 1+(1) | 1 | 1 | - | - | - | 3 | ▨6▨ | - | 4 |
| | HIVMAL | 1+(1) | - | 2 | 2 | 1 | - | - | 1 | ▨6▨ | 1 | 3 |
| | HIVZ321 | 2 | - | 1 | ▨1▨ | 1 | ▨1▨ | ▨1▨ | 3 | ▨5▨ | - | 2 |

▨▨▨ Ribozyme inactivated    (1) silent    - conserved

FIG. 40

SEQUENCE LISTING ( 1 ) GENERAL INFORMATION:

( i i i ) NUMBER OF SEQUENCES: 77

( 2 ) INFORMATION FOR SEQ ID NO:1:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AAGCTTCATA  TGCCATAATA  CTGATGAGTC  CGTGAGGACG                              40
AAACTGTGAC  GCGGCCGCCT  CGAGGCGCGC  GCATGCCTGC                              80
AGGTCGACTC  TAGAGCTTCA  TATGGTACAT  TGCTGATGAG                             120
TCCGTGAGGA  CGAAACTGTG  CTGCGGCCGC                                         150
```

( 2 ) INFORMATION FOR SEQ ID NO:2:

( i ) SEQUENCE CHARACTERISTICS:
        ( A ) LENGTH: 3426 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
TGGAAGGGCT  AATTTGGTCC  CAAAAAGAC   AAGAGATCCT                              40
TGATCTGTGG  ATCTACCACA  CACAAGGCTA  CTTCCCTGAT                              80
TGGCAGAACT  ACACACCAGG  GCCAGGGATC  AGATATCCAC                             120
TGACCTTTGG  ATGGTGCTTC  AAGTTAGTAC  CAGTTGAACC                             160
AGAGCAAGTA  GAAGAGGCCA  ATGAAGGAGA  GAACAACAGC                             200
TTGTTACACC  CTATGAGCCA  GCATGGGATG  GAGGACCCGG                             240
AGGGAGAAGT  ATTAGTGTGG  AAGTTTGACA  GCCTCCTAGC                             280
ATTTCGTCAC  ATGGCCCGAG  AGCTGCATCC  GGAGTACTAC                             320
AAAGACTGCT  GACATCGAGC  TTTCTACAAG  GGACTTTCCG                             360
CTGGGGACTT  TCCAGGGAGG  TGTGGCCTGG  GCGGGACTGG                             400
GGAGTGGCGA  GCCCTCAGAT  GCTACATATA  AGCAGCTGCT                             440
TTTTGCCTGT  ACTGGGTCTC  TCTGGTTAGA  CCAGATCTGA                             480
GCCTGGGAGC  TCTCTGGCTA  ACTAGGGAAC  CCACTGCTTA                             520
AGCCTCAATA  AAGCTTGCCT  TGAGTGCTCA  AAGTAGTGTG                             560
```

| | | | | |
|---|---|---|---|---|
| TGCCCGTCTG | TTGTGTGACT | CTGGTAACTA | GAGATCCCTC | 600 |
| AGACCCTTTT | AGTCAGTGTG | GAAAATCTCT | AGCAGTGGCG | 640 |
| CCCGAACAGG | GACTTGAAAG | CGAAAGTAAA | GCCAGAGGAG | 680 |
| ATCTCTCGAC | GCAGGACTCG | GCTTGCTGAA | GCGCGCACGG | 720 |
| CAAGAGGCGA | GGGGCGGCGA | CTGGTGAGTA | CGCCAAAAAT | 760 |
| TTTGACTAGC | GGAGGCTAGA | AGGAGAGAGA | TGAACCGGGG | 800 |
| AGTCCCTTTT | AGTCACTTGC | TTCTGGTGCT | GCAACTGGCG | 840 |
| CTCCTCCCAG | CAGCCACTCA | GGGAAAGAAA | GTGGTGCTGG | 880 |
| GCAAAAAAGG | GGATACAGTG | GAACTGACCT | GTACAGCTTC | 920 |
| CCAGAAGAAG | AGCATACAAT | TCCACTGGAA | AAACTCCAAC | 960 |
| CAGATAAAGA | TTCTGGGAAA | TCAGGGCTCC | TTCTTAACTA | 1000 |
| AAGGTCCATC | CAAGCTGAAT | GATCGCGCTG | ACTCAAGAAG | 1040 |
| AAGCCTTTGG | GACCAAGGAA | ACTTCCCCCT | GATCATTAAG | 1080 |
| AATCTTAAGA | TAGAAGACTC | AGATACTTAC | ATCTGTGAAG | 1120 |
| TGGAGGACCA | GAAGGAGGAG | GTGCAATTGC | TAGTGTTCGG | 1160 |
| ATTGACTGCC | AACTCTGACA | CCCACCTGCT | TCAGGGGCAG | 1200 |
| AGCCTGACCC | TGACCTTGGA | GAGCCCCCCT | GGTAGTAGCC | 1240 |
| CCTCAGTGCA | ATGTAGGAGT | CCAAGGGGTA | AAAACATACA | 1280 |
| GGGGGGGAAG | ACCCTCTCCG | TGTCTCAGCT | GGAGCTCCAG | 1320 |
| GATAGTGGCA | CCTGGACATG | CACTGTCTTG | CAGAACCAGA | 1360 |
| AGAAGGTGGA | GTTCAAAATA | GACATCGTGG | TGCTAGCTTT | 1400 |
| CCAGAAGGCC | TCCAGCATAG | TCTATAAGAA | AGAGGGGAA | 1440 |
| CAGGTGGAGT | TCTCCTTCCC | ACTCGCCTTT | ACAGTTGAAA | 1480 |
| AGCTGACGGG | CAGTGGCGAG | CTGTGGTGGC | AGGCGGAGAG | 1520 |
| GGCTTCCTCC | TCCAAGTCTT | GGATCATCTT | TGACCTGAAG | 1560 |
| AACAAGGAAG | TGTCTGTAAA | ACGGGTTACC | CAGGACCCTA | 1600 |
| AGCTCCAGAT | GGGCAAGAAG | CTCCCGCTCC | ACCTCACCCT | 1640 |
| GCCCCAGGCC | TTGCCTCAGT | ATGCTGGCTC | TGGAAACCTC | 1680 |
| ACCCTGGCCC | TTGAAGCGAA | AACAGGAAAG | TTGCATCAGG | 1720 |
| AAGTGAACCT | GGTGGTGATG | AGAGCCACTC | AGCTCCAGAA | 1760 |
| AAATTTGACC | TGTGAGGTGT | GGGGACCCAC | CTCCCCTAAG | 1800 |
| CTGATGCTGA | GCTTGAAACT | GGAGAACAAG | GAGGCAAAGG | 1840 |
| TCTCGAAGCG | GGAGAAGGCG | GTGTGGGTGC | TGAACCCTGA | 1880 |
| GGCGGGGATG | TGGCAGTGTC | TGCTGAGTGA | CTCGGGACAG | 1920 |
| GTCCTGCTGG | AATCCAACAT | CAAGGTTCTG | CCCATATGGT | 1960 |
| CCACCCCAGT | GCAGCCAATG | TTATTCATAA | TGATAGTAGG | 2000 |
| AGGCTTGGTA | GGTTTAAGAA | TAGTTTTTGC | TGTACTTTCT | 2040 |
| ATAGTGAATA | GAGTTAGGCA | GGGATATTCA | CCATTATCGT | 2080 |
| TTCAGACCCA | CCTCCCAATC | CCGAGGGGAC | CCGACAGGCC | 2120 |
| CGAAGGAATA | GAAGAAGAAG | GTGGAGAGAG | AGACAGAGAC | 2160 |

| | | | | |
|---|---|---|---|---|
| AGATCCATTC | GATTAGTGAA | CGGATCCTTA | GCACTTATCT | 2200 |
| GGGACGATCT | GCGGAGCCTG | TGCCTCTTCA | GCTACCACCG | 2240 |
| CTTGAGAGAC | TTACTCTTGA | TTGTAACGAG | GATTGTGGAA | 2280 |
| CTTCTGGGAC | GCAGGGGTG | GGAAGCCCTC | AAATATTGGT | 2320 |
| GGAATCTCCT | ACAGTATTGG | AGTCAGGAAC | TAAAGAATAG | 2360 |
| TGCTGTTAAC | TTGCTCAATG | CCACAGCCAT | AGCAGTAGCT | 2400 |
| GAGGGGACAG | ATAGGGTTAT | AGAAGTATTA | CAAGCAGCTT | 2440 |
| ATAGAGCTAT | TCGCCACATA | CCTAGAAGAA | TAAGACAGGG | 2480 |
| CTTGGAAAGG | ATTTTGCTAT | AAGATGGGTG | GCAAGTGGTC | 2520 |
| AAAAAGTAGT | GTGATTGGAT | GGCCTGCTGT | AAGGGAAAGA | 2560 |
| ATGAGACGAG | CTGAGCCAGC | AGCAGATGGG | GTGGGAGCAG | 2600 |
| TATCTCGAGA | CCTAGAAAAA | CATGGAGCAA | TCACAAGTAG | 2640 |
| CAATACAGCA | GCTAACAATG | CTGCTTGTGC | CTGGCTAGAA | 2680 |
| GCACAAGAGG | AGGAAGAGGT | GGGTTTTCCA | GTCACACCTC | 2720 |
| AGGTACCTTT | AAGACCAATG | ACTTACAAGG | CAGCTGTAGA | 2760 |
| TCTTAGCCAC | TTTTTAAAAG | AAAAGGGGGG | ACTGGAAGGG | 2800 |
| CTAATTCACT | CCCAAAGAAG | ACAAGATATC | CTTGATCTGT | 2840 |
| GGATCTACCA | CACACAAGGC | TACTTCCCTG | ATTGGCAGAA | 2880 |
| CTACACACCA | GGGCCAGGGG | TCAGATATCC | ACTGACCTTT | 2920 |
| GGATGGTGCT | ACAAGCTAGT | ACCAGTTGAG | CCAGATAAGG | 2960 |
| TAGAAGAGGC | CAATAAAGGA | GAGAACACCA | GCTTGTTACA | 3000 |
| CCCTGTGAGC | CTGCATGGAA | TGGATGACCC | TGAGAGAGAA | 3040 |
| GTGTTAGAGT | GGAGGTTTGA | CAGCCGCCTA | GCATTTCATC | 3080 |
| ACGTGGCCCG | AGAGCTGCAT | CCGGAGTACT | TCAAGAACTG | 3120 |
| CTGACATCGA | GCTTGCTACA | AGGGACTTTC | CGCTGGGGAC | 3160 |
| TTTCCAGGGA | GGCGTGGCCT | GGGCGGGACT | GGGGAGTGGC | 3200 |
| GAGCCCTCAG | ATGCTGCATA | TAAGCAGCTG | CTTTTTGCCT | 3240 |
| GTACTGGGTC | TCTCTGGTTA | GACCAGATCT | GAGCCTGGGA | 3280 |
| GCTCTCTGGC | TAACTAGGGA | ACCCACTGCT | TAAGCCTCAA | 3320 |
| TAAAGCTTGC | CTTGAGTGCT | TCAAGTAGTG | TGTGCCCGTC | 3360 |
| TGTTGTGTGA | CTCTGGTAAC | TAGAGATCCC | TCAGACCCTT | 3400 |
| TTAGTCAGTG | TGGAAAATCT | CTAGCA | | 3426 |

( 2 ) INFORMATION FOR SEQ ID NO:3:

( i ) SEQUENCE CHARACTERISTICS:
        ( A ) LENGTH: 2940 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

| | | | | |
|---|---|---|---|---|
| GAATTCTGTA | ATACGACTCA | CTATAGGTCT | CTCTGGTTAG | 40 |
| ACCAGATCTG | AGCCTGGGAG | CTCTCTGGCT | AACTAGGGAA | 80 |

-continued

| | | | | |
|---|---|---|---|---|
| CCCACTGCTT | AAGCCTCAAT | AAAGCTTGCC | TTGAGTGCTC | 120 |
| AAAGTAGTGT | GTGCCCGTCT | GTTGTGTGAC | TCTGGTAACT | 160 |
| AGAGATCCCT | CAGACCCTTT | TAGTCAGTGT | GGAAAATCTC | 200 |
| TAGCAGTGGC | GCCCGAACAG | GGACTTGAAA | GCGAAAGTAA | 240 |
| AGCCAGAGGA | GATCTCTCGA | CGCAGGACTC | GGCTTGCTGA | 280 |
| AGCGCGCACG | GCAAGAGGCG | AGGGCGGCG | ACTGGTGAGT | 320 |
| ACGCCAAAAA | TTTTGACTAG | CGGAGGCTAG | AAGGAGAGAG | 360 |
| ATGAACCGGG | GAGTCCCTTT | TAGTCACTTG | CTTCTGGTGC | 400 |
| TGCAACTGGC | GCTCCTCCCA | GCAGCCACTC | AGGGAAAGAA | 440 |
| AGTGGTGCTG | GGCAAAAAG | GGGATACAGT | GGAACTGACC | 480 |
| TGTACAGCTT | CCCAGAAGAA | GAGCATACAA | TTCCACTGGA | 520 |
| AAAACTCCAA | CCAGATAAAG | ATTCTGGAA | ATCAGGGCTC | 560 |
| CTTCTTAACT | AAAGGTCCAT | CCAAGCTGAA | TGATCGCGCT | 600 |
| GACTCAAGAA | GAAGCCTTTG | GGACCAAGGA | AACTTCCCCC | 640 |
| TGATCATTAA | GAATCTTAAG | ATAGAAGACT | CAGATACTTA | 680 |
| CATCTGTGAA | GTGGAGGACC | AGAAGGAGGA | GGTGCAATTG | 720 |
| CTAGTGTTCG | GATTGACTGC | CAACTCTGAC | ACCCACCTGC | 760 |
| TTCAGGGGCA | GAGCCTGACC | CTGACCTTGG | AGAGCCCCC | 800 |
| TGGTAGTAGC | CCCTCAGTGC | AATGTAGGAG | TCCAAGGGGT | 840 |
| AAAACATAC | AGGGGGGAA | GACCCTCTCC | GTGTCTCAGC | 880 |
| TGGAGCTCCA | GGATAGTGGC | ACCTGGACAT | GCACTGTCTT | 920 |
| GCAGAACCAG | AAGAAGGTGG | AGTTCAAAAT | AGACATCGTG | 960 |
| GTGCTAGCTT | TCCAGAAGGC | CTCCAGCATA | GTCTATAAGA | 1000 |
| AAGAGGGGA | ACAGGTGGAG | TTCTCCTTCC | CACTCGCCTT | 1040 |
| TACAGTTGAA | AAGCTGACGG | GCAGTGGCGA | GCTGTGGTGG | 1080 |
| CAGGCGGAGA | GGGCTTCCTC | CTCCAAGTCT | TGGATCATCT | 1120 |
| TTGACCTGAA | GAACAAGGAA | GTGTCTGTAA | AACGGGTTAC | 1160 |
| CCAGGACCCT | AAGCTCCAGA | TGGGCAAGAA | GCTCCGCTC | 1200 |
| CACCTCACCC | TGCCCCAGGC | CTTGCCTCAG | TATGCTGGCT | 1240 |
| CTGGAAACCT | CACCCTGGCC | CTTGAAGCGA | AAACAGGAAA | 1280 |
| GTTGCATCAG | GAAGTGAACC | TGGTGGTGAT | GAGAGCCACT | 1320 |
| CAGCTCCAGA | AAAATTTGAC | CTGTGAGGTG | TGGGGACCCA | 1360 |
| CCTCCCCTAA | GCTGATGCTG | AGCTTGAAAC | TGGAGAACAA | 1400 |
| GGAGGCAAAG | GTCTCGAAGC | GGGAGAAGGC | GGTGTGGGTG | 1440 |
| CTGAACCCTG | AGGCGGGGAT | GTGGCAGTGT | CTGCTGAGTG | 1480 |
| ACTCGGGACA | GGTCCTGCTG | GAATCCAACA | TCAAGGTTCT | 1520 |
| GCCCATATGG | TCCACCCCAG | TGCAGCCAAT | GTTATTCATA | 1560 |
| ATGATAGTAG | GAGGCTTGGT | AGGTTTAAGA | ATAGTTTTTG | 1600 |
| CTGTACTTTC | TATAGTGAAT | AGAGTTAGGC | AGGGATATTC | 1640 |
| ACCATTATCG | TTTCAGACCC | ACCTCCCAAT | CCCGAGGGGA | 1680 |

| | | | | |
|---|---|---|---|---|
| CCCGACAGGC | CCGAAGGAAT | AGAAGAAGAA | GGTGGAGAGA | 1720 |
| GAGACAGAGA | CAGATCCATT | CGATTAGTGA | ACGGATCCTT | 1760 |
| AGCACTTATC | TGGGACGATC | TGCGGAGCCT | GTGCCTCTTC | 1800 |
| AGCTACCACC | GCTTGAGAGA | CTTACTCTTG | ATTGTAACGA | 1840 |
| GGATTGTGGA | ACTTCTGGGA | CGCAGGGGGG | GGGAAGCCCT | 1880 |
| CAAATATTGG | TGGAATCTCC | TACAGTATTG | GAGTCAGGAA | 1920 |
| CTAAAGAATA | GTGCTGTTAA | CTTGCTCAAT | GCCACAGCCA | 1960 |
| TAGCAGTAGC | TGAGGGACA | GATAGGGTTA | TAGAAGTATT | 2000 |
| ACAAGCAGCT | TATAGAGCTA | TTCGCCACAT | ACCTAGAAGA | 2040 |
| ATAAGACAGG | GCTTGGAAAG | GATTTTGCTA | TAAGATGGGT | 2080 |
| GGCAAGTGGT | CAAAAAGTAG | TGTGATTGGA | TGGCCTGCTG | 2120 |
| TAAGGGAAAG | AATGAGACGA | GCTGAGCCAG | CAGCAGATGG | 2160 |
| GGTGGGAGCA | GTATCTCGAG | ACCTAGAAAA | ACATGGAGCA | 2200 |
| ATCACAAGTA | GCAATACAGC | AGCTAACAAT | GCTGCTTGTG | 2240 |
| CCTGGCTAGA | AGCACAAGAG | GAGGAAGAGG | TGGGTTTTCC | 2280 |
| AGTCACACCT | CAGGTACCTT | TAAGACCAAT | GACTTACAAG | 2320 |
| GCAGCTGTAG | ATCTTAGCCA | CTTTTTAAAA | GAAAAGGGGG | 2360 |
| GACTGGAAGG | GCTAATTCAC | TCCCAAAGAA | GACAAGATAT | 2400 |
| CCTTGATCTG | TGGATCTACC | ACACACAAGG | CTACTTCCCT | 2440 |
| GATTGGCAGA | ACTACACACC | AGGGCCAGGG | GTCAGATATC | 2480 |
| CACTGACCTT | TGGATGGTGC | TACAAGCTAG | TACCAGTTGA | 2520 |
| GCCAGATAAG | GTAGAAGAGG | CCAATAAAGG | AGAGAACACC | 2560 |
| AGCTTGTTAC | ACCCTGTGAG | CCTGCATGGA | ATGGATGACC | 2600 |
| CTGAGAGAGA | AGTGTTAGAG | TGGAGGTTTG | ACAGCCGCCT | 2640 |
| AGCATTTCAT | CACGTGGCCC | GAGAGCTGCA | TCCGGAGTAC | 2680 |
| TTCAAGAACT | GCTGACATCG | AGCTTGCTAC | AAGGGACTTT | 2720 |
| CCGCTGGGGA | CTTTCCAGGG | AGGCGTGGCC | TGGGCGGGAC | 2760 |
| TGGGGAGTGG | CGAGCCCTCA | GATGCTGCAT | ATAAGCAGCT | 2800 |
| GCTTTTTGCC | TGTACTGGGT | CTCTCTGGTT | AGACCAGATC | 2840 |
| TGAGCCTGGG | AGCTCTCTGG | CTAACTAGGG | AACCCACTGC | 2880 |
| TTAAGCCTCA | ATAAAGCTTG | CCTTGAGTGC | TTCAAAAAAA | 2920 |
| AAAAAAAAT | GCATCTGCAG | | | 2940 |

( 2 ) INFORMATION FOR SEQ ID NO:4:

( i ) SEQUENCE CHARACTERISTICS:
        ( A ) LENGTH: 3480 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

| | | | | |
|---|---|---|---|---|
| TGGAAGGGCT | AATTTGGTCC | CAAAAAGAC | AAGAGATCCT | 40 |
| TGATCTGTGG | ATCTACCACA | CACAAGGCTA | CTTCCCTGAT | 80 |
| TGGCAGAACT | ACACACCAGG | GCCAGGGATC | AGATATCCAC | 120 |

| | | | | |
|---|---|---|---|---|
| TGACCTTTGG | ATGGTGCTTC | AAGTTAGTAC | CAGTTGAACC | 160 |
| AGAGCAAGTA | GAAGAGGCCA | ATGAAGGAGA | GAACAACAGC | 200 |
| TTGTTACACC | CTATGAGCCA | GCATGGGATG | GAGGACCCGG | 240 |
| AGGGAGAAGT | ATTAGTGTGG | AAGTTTGACA | GCCTCCTAGC | 280 |
| ATTTCGTCAC | ATGGCCCGAG | AGCTGCATCC | GGAGTACTAC | 320 |
| AAAGACTGCT | GACATCGAGC | TTTCTACAAG | GACTTTCCG | 360 |
| CTGGGGACTT | TCCAGGGAGG | TGTGGCCTGG | GCGGGACTGG | 400 |
| GGAGTGGCGA | GCCCTCAGAT | GCTACATATA | AGCAGCTGCT | 440 |
| TTTTGCCTGT | ACTGGGTCTC | TCTGGTTAGA | CCAGATCTGA | 480 |
| GCCTGGGAGC | TCTCTGGCTA | ACTAGGGAAC | CCACTGCTTA | 520 |
| AGCCTCAATA | AAGCTTGCCT | TGAGTGCTCA | AAGTAGTGTG | 560 |
| TGCCCGTCTG | TTGTGTGACT | CTGGTAACTA | GAGATCCCTC | 600 |
| AGACCCTTTT | AGTCAGTGTG | GAAAATCTCT | AGCAGTGGCG | 640 |
| CCCGAACAGG | GACTTGAAAG | CGAAAGTAAA | GCCAGAGGAG | 680 |
| ATCTCTCGAC | GCAGGACTCG | GCTTGCTGAA | GCGCGCACGG | 720 |
| CAAGAGGCGA | GGGGCGGCGA | CTGGTGAGTA | CGCCAAAAAT | 760 |
| TTTGACTAGC | GGAGGCTAGA | AGGAGAGAGA | TGAACCGGGG | 800 |
| AGTCCCTTTT | AGTCACTTGC | TTCTGGTGCT | GCAACTGGCG | 840 |
| CTCCTCCCAG | CAGCCACTCA | GGGAAAGAAA | GTGGTGCTGG | 880 |
| GCAAAAAAGG | GGATACAGTG | GAACTGACCT | GTACAGCTTC | 920 |
| CCAGAAGAAG | AGCATACAAT | TCCACTGGAA | AAACTCCAAC | 960 |
| CAGATAAAGA | TTCTGGGAAA | TCAGGGCTCC | TTCTTAACTA | 1000 |
| AAGGTCCATC | CAAGCTGAAT | GATCGCGCTG | ACTCAAGAAG | 1040 |
| AAGCCTTTGG | GACCAAGGAA | ACTTCCCCCT | GATCATTAAG | 1080 |
| AATCTTAAGA | TAGAAGACTC | AGATACTTAC | ATCTGTGAAG | 1120 |
| TGGAGGACCA | GAAGGAGGAG | GTGCAATTGC | TAGTGTTCGG | 1160 |
| ATTGACTGCC | AACTCTGACA | CCCACCTGCT | TCAGGGGCAG | 1200 |
| AGCCTGACCC | TGACCTTGGA | GAGCCCCCCT | GGTAGTAGCC | 1240 |
| CCTCAGTGCA | ATGTAGGAGT | CCAAGGGGTA | AAAACATACA | 1280 |
| GGGGGGGAAG | ACCCTCTCCG | TGTCTCAGCT | GGAGCTCCAG | 1320 |
| GATAGTGGCA | CCTGGACATG | CACTGTCTTG | CAGAACCAGA | 1360 |
| AGAAGGTGGA | GTTCAAAATA | GACATCGTGG | TGCTAGCTTT | 1400 |
| CCAGAAGGCC | TCCAGCATAG | TCTATAAGAA | AGAGGGGAA | 1440 |
| CAGGTGGAGT | TCTCCTTCCC | ACTCGCCTTT | ACAGTTGAAA | 1480 |
| AGCTGACGGG | CAGTGGCGAG | CTGTGGTGGC | AGGCGGAGAG | 1520 |
| GGCTTCCTCC | TCCAAGTCTT | GGATCATCTT | TGACCTGAAG | 1560 |
| AACAAGGAAG | TGTCTGTAAA | ACGGGTTACC | CAGGACCCTA | 1600 |
| AGCTCCAGAT | GGGCAAGAAG | CTCCCGCTCC | ACCTCACCCT | 1640 |
| GCCCCAGGCC | TTGCCTCAGT | ATGCTGGCTC | TGGAAACCTC | 1680 |
| ACCCTGGCCC | TTGAAGCGAA | AACAGGAAAG | TTGCATCAGG | 1720 |

```
AAGTGAACCT  GGTGGTGATG  AGAGCCACTC  AGCTCCAGAA                    1760

AAATTTGACC  TGTGAGGTGT  GGGGACCCAC  CTCCCCTAAG                    1800

CTGATGCTGA  GCTTGAAACT  GGAGAACAAG  GAGGCAAAGG                    1840

TCTCGAAGCG  GGAGAAGGCG  GTGTGGGTGC  TGAACCCTGA                    1880

GGCGGGGATG  TGGCAGTGTC  TGCTGAGTGA  CTCGGGACAG                    1920

GTCCTGCTGG  AATCCAACAT  CAAGGTTCTG  CCCATATGGT                    1960

CCACCCCAGT  GCAGCCAATG  TTATTCATAA  TGATAGTAGG                    2000

AGGCTTGGTA  GGTTTAAGAA  TAGTTTTTGC  TGTACTTTCT                    2040

ATAGTGAATA  GAGTTAGGCA  GGGATATTCA  CCATTATCGT                    2080

TTCAGACCCA  CCTCCCAATC  CCGAGGGGAC  CCGACAGGCC                    2120

CGAAGGAATA  GAAGAAGAAG  GTGGAGAGAG  AGACAGAGAC                    2160

AGATCCATTC  GATTAGTGAA  CGGATCCTTA  GCACTTATCT                    2200

GGGACGATCT  GCGGAGCCTG  TGCCTCTTCA  GCTACCACCG                    2240

CTTGAGAGAC  TTACTCTTGA  TTGTAACGAG  GATTGTGGAA                    2280

CTTCTGGGAC  GCAGGGGTG   GGAAGCCCTC  AAATATTGGT                    2320

GGAATCTCCT  ACAGTATTGG  AGTCAGGAAC  TAAAGAATAG                    2360

TGCTGTTAAC  TTGCTCAATG  CCACAGCCAT  AGCAGTAGCT                    2400

GAGGGGACAG  ATAGGGTTAT  AGAAGTATTA  CAAGCAGCTT                    2440

ATAGAGCTAT  TCGCCACATA  CCTAGAAGAA  TAAGACAGGG                    2480

CTTGGAAAGG  ATTTTGCTAT  AAGCATATGG  TACATTGCTG                    2520

ATGAGTCCGT  GAGGACGAAA  CTGTGCTGCG  GCCGCTATAA                    2560

GGTGGCAAGT  GGTCAAAAAG  TAGTGTGATT  GGATGGCCTG                    2600

CTGTAAGGGA  AAGAATGAGA  CGAGCTGAGC  CAGCAGCAGA                    2640

TGGGGTGGGA  GCAGTATCTC  GAGACCTAGA  AAAACATGGA                    2680

GCAATCACAA  GTAGCAATAC  AGCAGCTAAC  AATGCTGCTT                    2720

GTGCCTGGCT  AGAAGCACAA  GAGGAGGAAG  AGGTGGGTTT                    2760

TCCAGTCACA  CCTCAGGTAC  CTTTAAGACC  AATGACTTAC                    2800

AAGGCAGCTG  TAGATCTTAG  CCACTTTTTA  AAAGAAAAGG                    2840

GGGGACTGGA  AGGGCTAATT  CACTCCCAAA  GAAGACAAGA                    2880

TATCCTTGAT  CTGTGGATCT  ACCACACACA  AGGCTACTTC                    2920

CCTGATTGGC  AGAACTACAC  ACCAGGGCCA  GGGGTCAGAT                    2960

ATCCACTGAC  CTTTGGATGG  TGCTACAAGC  TAGTACCAGT                    3000

TGAGCCAGAT  AAGGTAGAAG  AGGCCAATAA  AGGAGAGAAC                    3040

ACCAGCTTGT  TACACCCTGT  GAGCCTGCAT  GGAATGGATG                    3080

ACCCTGAGAG  AGAAGTGTTA  GAGTGGAGGT  TTGACAGCCG                    3120

CCTAGCATTT  CATCACGTGG  CCCGAGAGCT  GCATCCGGAG                    3160

TACTTCAAGA  ACTGCTGACA  TCGAGCTTGC  TACAAGGGAC                    3200

TTTCCGCTGG  GGACTTTCCA  GGGAGGCGTG  GCCTGGGCGG                    3240

GACTGGGGAG  TGGCGAGCCC  TCAGATGCTG  CATATAAGCA                    3280

GCTGCTTTTT  GCCTGTACTG  GGTCTCTCTG  GTTAGACCAG                    3320
```

```
ATCTGAGCCT  GGGAGCTCTC  TGGCTAACTA  GGGAACCCAC                    3360

TGCTTAAGCC  TCAATAAAGC  TTGCCTTGAG  TGCTTCAAGT                    3400

AGTGTGTGCC  CGTCTGTTGT  GTGACTCTGG  TAACTAGAGA                    3440

TCCCTCAGAC  CCTTTTAGTC  AGTGTGGAAA  ATCTCTAGCA                    3480
```

( 2 ) INFORMATION FOR SEQ ID NO:5:

( i ) SEQUENCE CHARACTERISTICS:
        ( A ) LENGTH: 3721 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
TGGAAGGGCT  AATTTGGTCC  CAAAAAAGAC  AAGAGATCCT                      40

TGATCTGTGG  ATCTACCACA  CACAAGGCTA  CTTCCCTGAT                      80

TGGCAGAACT  ACACACCAGG  GCCAGGGATC  AGATATCCAC                     120

TGACCTTTGG  ATGGTGCTTC  AAGTTAGTAC  CAGTTGAACC                     160

AGAGCAAGTA  GAAGAGGCCA  ATGAAGGAGA  GAACAACAGC                     200

TTGTTACACC  CTATGAGCCA  GCATGGGATG  GAGGACCCGG                     240

AGGGAGAAGT  ATTAGTGTGG  AAGTTTGACA  GCCTCCTAGC                     280

ATTTCGTCAC  ATGGCCCGAG  AGCTGCATCC  GGAGTACTAC                     320

AAAGACTGCT  GACATCGAGC  TTTCTACAAG  GGACTTTCCG                     360

CTGGGGACTT  TCCAGGGAGG  TGTGGCCTGG  GCGGGACTGG                     400

GGAGTGGCGA  GCCCTCAGAT  GCTACATATA  AGCAGCTGCT                     440

TTTTGCCTGT  ACTGGGTCTC  TCTGGTTAGA  CCAGATCTGA                     480

GCCTGGGAGC  TCTCTGGCTA  ACTAGGGAAC  CCACTGCTTA                     520

AGCCTCAATA  AAGCTTGCCT  TGAGTGCTCA  AAGTAGTGTG                     560

TGCCCGTCTG  TTGTGTGACT  CTGGTAACTA  GAGATCCCTC                     600

AGACCCTTTT  AGTCAGTGTG  GAAAATCTCT  AGCAGTGGCG                     640

CCCGAACAGG  GACTTGAAAG  CGAAAGTAAA  GCCAGAGGAG                     680

ATCTCTCGAC  GCAGGACTCG  GCTTGCTGAA  GCGCGCACGG                     720

CAAGAGGCGA  GGGGCGGCGA  CTGGTGAGTA  CGCCAAAAAT                     760

TTTGACTAGC  GGAGGCTAGA  AGGAGAGAGA  TGAACCGGGG                     800

AGTCCCTTTT  AGTCACTTGC  TTCTGGTGCT  GCAACTGGCG                     840

CTCCTCCCAG  CAGCCACTCA  GGGAAAGAA   GTGGTGCTGG                     880

GCAAAAAAGG  GGATACAGTG  GAACTGACCT  GTACAGCTTC                     920

CCAGAAGAAG  AGCATACAAT  TCCACTGGAA  AAACTCCAAC                     960

CAGATAAAGA  TTCTGGGAAA  TCAGGGCTCC  TTCTTAACTA                    1000

AAGGTCCATC  CAAGCTGAAT  GATCGCGCTG  ACTCAAGAAG                    1040

AAGCCTTTGG  GACCAAGGAA  ACTTCCCCCT  GATCATTAAG                    1080

AATCTTAAGA  TAGAAGACTC  AGATACTTAC  ATCTGTGAAG                    1120

TGGAGGACCA  GAAGGAGGAG  GTGCAATTGC  TAGTGTTCGG                    1160

ATTGACTGCC  AACTCTGACA  CCCACCTGCT  TCAGGGGCAG                    1200
```

| | | | | |
|---|---|---|---|---|
| AGCCTGACCC | TGACCTTGGA | GAGCCCCCCT | GGTAGTAGCC | 1240 |
| CCTCAGTGCA | ATGTAGGAGT | CCAAGGGGTA | AAAACATACA | 1280 |
| GGGGGGGAAG | ACCCTCTCCG | TGTCTCAGCT | GGAGCTCCAG | 1320 |
| GATAGTGGCA | CCTGGACATG | CACTGTCTTG | CAGAACCAGA | 1360 |
| AGAAGGTGGA | GTTCAAAATA | GACATCGTGG | TGCTAGCTTT | 1400 |
| CCAGAAGGCC | TCCAGCATAG | TCTATAAGAA | AGAGGGGAA | 1440 |
| CAGGTGGAGT | TCTCCTTCCC | ACTCGCCTTT | ACAGTTGAAA | 1480 |
| AGCTGACGGG | CAGTGGCGAG | CTGTGGTGGC | AGGCGGAGAG | 1520 |
| GGCTTCCTCC | TCCAAGTCTT | GGATCATCTT | TGACCTGAAG | 1560 |
| AACAAGGAAG | TGTCTGTAAA | ACGGGTTACC | CAGGACCCTA | 1600 |
| AGCTCCAGAT | GGGCAAGAAG | CTCCCGCTCC | ACCTCACCCT | 1640 |
| GCCCCAGGCC | TTGCCTCAGT | ATGCTGGCTC | TGGAAACCTC | 1680 |
| ACCCTGGCCC | TTGAAGCGAA | AACAGGAAAG | TTGCATCAGG | 1720 |
| AAGTGAACCT | GGTGGTGATG | AGAGCCACTC | AGCTCCAGAA | 1760 |
| AAATTTGACC | TGTGAGGTGT | GGGGACCCAC | CTCCCCTAAG | 1800 |
| CTGATGCTGA | GCTTGAAACT | GGAGAACAAG | GAGGCAAAGG | 1840 |
| TCTCGAAGCG | GGAGAAGGCG | GTGTGGGTGC | TGAACCCTGA | 1880 |
| GGCGGGGATG | TGGCAGTGTC | TGCTGAGTGA | CTCGGGACAG | 1920 |
| GTCCTGCTGG | AATCCAACAT | CAAGGTTCTG | CCCATATGGT | 1960 |
| CCACCCCAGT | GCAGCCAATG | TTATTCATAA | TGATAGTAGG | 2000 |
| AGGCTTGGTA | GGTTTAAGAA | TAGTTTTTGC | TGTACTTTCT | 2040 |
| ATAGTGAATA | GAGTTAGGCA | GGGATATTCA | CCATTATCGT | 2080 |
| TTCAGACCCA | CCTCCCAATC | CCGAGGGGAC | CCGACAGGCC | 2120 |
| CGAAGGAATA | GAAGAAGAAG | GTGGAGAGAG | AGACAGAGAC | 2160 |
| AGATCCATTC | GATTAGTGAA | CGGATCCTTA | GCACTTATCT | 2200 |
| GGGACGATCT | GCGGAGCCTG | TGCCTCTTCA | GCTACCACCG | 2240 |
| CTTGAGAGAC | TTACTCTTGA | TTGTAACGAG | GATTGTGGAA | 2280 |
| CTTCTGGGAC | GCAGGGGGTG | GGAAGCCCTC | AAATATTGGT | 2320 |
| GGAATCTCCT | ACAGTATTGG | AGTCAGGAAC | TAAAGAATAG | 2360 |
| TGCTGTTAAC | TTGCTCAATG | CCACAGCCAT | AGCAGTAGCT | 2400 |
| GAGGGGACAG | ATAGGGTTAT | AGAAGTATTA | CAAGCAGCTT | 2440 |
| ATAGAGCTAT | TCGCCACATA | CCTAGAAGAA | TAAGACAGGG | 2480 |
| CTTGGAAAGG | ATTTTGCTAT | AAGCATATGG | TACATTGCTG | 2520 |
| ATGAGTCCGT | GAGGACGAAA | CTGTGCTGCG | GCCGCAGGAG | 2560 |
| CTTTGTTCCT | TGGGTTCTTG | GGAGCAGCAG | GAAGCACTAT | 2600 |
| GGGCTGCACG | TCAATGACGC | TGACGGTACA | GGCCAGACAA | 2640 |
| TTATTGTCTG | ATATAGTGCA | GCAGCAGAAC | AATTTGCTGA | 2680 |
| GGGCTATTGA | GGCGCAACAG | CATCTGTTGC | AACTCACAGT | 2720 |
| CTGGGGCATC | AAACAGCTCC | AGGCAAGAAT | CCTGGCTGTG | 2760 |
| GAAAGATACC | TAAAGGACAA | CAGCTCCTGC | GGCCGCTATA | 2800 |

| | | | | |
|---|---|---|---|---|
| AGGTGGCAAG | TGGTCAAAAA | GTAGTGTGAT | TGGATGGCCT | 2840 |
| GCTGTAAGGG | AAAGAATGAG | ACGAGCTGAG | CCAGCAGCAG | 2880 |
| ATGGGGTGGG | AGCAGTATCT | CGAGACCTAG | AAAAACATGG | 2920 |
| AGCAATCACA | AGTAGCAATA | CAGCAGCTAA | CAATGCTGCT | 2960 |
| TGTGCCTGGC | TAGAAGCACA | AGAGGAGGAA | GAGGTGGGTT | 3000 |
| TTCCAGTCAC | ACCTCAGGTA | CCTTTAAGAC | CAATGACTTA | 3040 |
| CAAGGCAGCT | GTAGATCTTA | GCCACTTTTT | AAAAGAAAAG | 3080 |
| GGGGGACTGG | AAGGGCTAAT | TCACTCCCAA | AGAAGACAAG | 3120 |
| ATATCCTTGA | TCTGTGGATC | TACCACACAC | AAGGCTACTT | 3160 |
| CCCTGATTGG | CAGAACTACA | CACCAGGGCC | AGGGGTCAGA | 3200 |
| TATCCACTGA | CCTTTGGATG | GTGCTACAAG | CTAGTACCAG | 3240 |
| TTGAGCCAGA | TAAGGTAGAA | GAGGCCAATA | AAGGAGAGAA | 3280 |
| CACCAGCTTG | TTACACCCTG | TGAGCCTGCA | TGGAATGGAT | 3320 |
| GACCCTGAGA | GAGAAGTGTT | AGAGTGGAGG | TTTGACAGCC | 3360 |
| GCCTAGCATT | TCATCACGTG | GCCCGAGAGC | TGCATCCGGA | 3400 |
| GTACTTCAAG | AACTGCTGAC | ATCGAGCTTG | CTACAAGGGA | 3440 |
| CTTTCCGCTG | GGACTTTCC | AGGGAGGCGT | GGCCTGGGCG | 3480 |
| GGACTGGGGA | GTGGCGAGCC | CTCAGATGCT | GCATATAAGC | 3520 |
| AGCTGCTTTT | TGCCTGTACT | GGGTCTCTCT | GGTTAGACCA | 3560 |
| GATCTGAGCC | TGGGAGCTCT | CTGGCTAACT | AGGGAACCCA | 3600 |
| CTGCTTAAGC | CTCAATAAAG | CTTGCCTTGA | GTGCTTCAAG | 3640 |
| TAGTGTGTGC | CCGTCTGTTG | TGTGACTCTG | GTAACTAGAG | 3680 |
| ATCCCTCAGA | CCCTTTTAGT | CAGTGTGGAA | AATCTCTAGC | 3720 |
| A | | | | 3721 |

( 2 ) INFORMATION FOR SEQ ID NO:6:

( i ) SEQUENCE CHARACTERISTICS:
        ( A ) LENGTH: 3993 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

| | | | | |
|---|---|---|---|---|
| TGGAAGGGCT | AATTTGGTCC | CAAAAAAGAC | AAGAGATCCT | 40 |
| TGATCTGTGG | ATCTACCACA | CACAAGGCTA | CTTCCCTGAT | 80 |
| TGGCAGAACT | ACACACCAGG | GCCAGGGATC | AGATATCCAC | 120 |
| TGACCTTTGG | ATGGTGCTTC | AAGTTAGTAC | CAGTTGAACC | 160 |
| AGAGCAAGTA | GAAGAGGCCA | ATGAAGGAGA | GAACAACAGC | 200 |
| TTGTTACACC | CTATGAGCCA | GCATGGGATG | GAGGACCCGG | 240 |
| AGGGAGAAGT | ATTAGTGTGG | AAGTTTGACA | GCCTCCTAGC | 280 |
| ATTTCGTCAC | ATGGCCCGAG | AGCTGCATCC | GGAGTACTAC | 320 |
| AAAGACTGCT | GACATCGAGC | TTTCTACAAG | GGACTTTCCG | 360 |
| CTGGGGACTT | TCCAGGGAGG | TGTGGCCTGG | GCGGGACTGG | 400 |
| GGAGTGGCGA | GCCCTCAGAT | GCTACATATA | AGCAGCTGCT | 440 |

| | | | | |
|---|---|---|---|---|
| TTTTGCCTGT | ACTGGGTCTC | TCTGGTTAGA | CCAGATCTGA | 480 |
| GCCTGGGAGC | TCTCTGGCTA | ACTAGGGAAC | CCACTGCTTA | 520 |
| AGCCTCAATA | AAGCTTGCCT | TGAGTGCTCA | AAGTAGTGTG | 560 |
| TGCCCGTCTG | TTGTGTGACT | CTGGTAACTA | GAGATCCCTC | 600 |
| AGACCCTTTT | AGTCAGTGTG | GAAAATCTCT | AGCAGTGGCG | 640 |
| CCCGAACAGG | GACTTGAAAG | CGAAAGTAAA | GCCAGAGGAG | 680 |
| ATCTCTCGAC | GCAGGACTCG | GCTTGCTGAA | GCGCGCACGG | 720 |
| CAAGAGGCGA | GGGGCGGCGA | CTGGTGAGTA | CGCCAAAAAT | 760 |
| TTTGACTAGC | GGAGGCTAGA | AGGAGAGAGA | TGAACCGGGG | 800 |
| AGTCCCTTTT | AGTCACTTGC | TTCTGGTGCT | GCAACTGGCG | 840 |
| CTCCTCCCAG | CAGCCACTCA | GGGAAAGAAA | GTGGTGCTGG | 880 |
| GCAAAAAAGG | GGATACAGTG | GAACTGACCT | GTACAGCTTC | 920 |
| CCAGAAGAAG | AGCATACAAT | TCCACTGGAA | AAACTCCAAC | 960 |
| CAGATAAAGA | TTCTGGGAAA | TCAGGGCTCC | TTCTTAACTA | 1000 |
| AAGGTCCATC | CAAGCTGAAT | GATCGCGCTG | ACTCAAGAAG | 1040 |
| AAGCCTTTGG | GACCAAGGAA | ACTTCCCCCT | GATCATTAAG | 1080 |
| AATCTTAAGA | TAGAAGACTC | AGATACTTAC | ATCTGTGAAG | 1120 |
| TGGAGGACCA | GAAGGAGGAG | GTGCAATTGC | TAGTGTTCGG | 1160 |
| ATTGACTGCC | AACTCTGACA | CCCACCTGCT | TCAGGGGCAG | 1200 |
| AGCCTGACCC | TGACCTTGGA | GAGCCCCCCT | GGTAGTAGCC | 1240 |
| CCTCAGTGCA | ATGTAGGAGT | CCAAGGGGTA | AAAACATACA | 1280 |
| GGGGGGGAAG | ACCCTCTCCG | TGTCTCAGCT | GGAGCTCCAG | 1320 |
| GATAGTGGCA | CCTGGACATG | CACTGTCTTG | CAGAACCAGA | 1360 |
| AGAAGGTGGA | GTTCAAAATA | GACATCGTGG | TGCTAGCTTT | 1400 |
| CCAGAAGGCC | TCCAGCATAG | TCTATAAGAA | AGAGGGGGAA | 1440 |
| CAGGTGGAGT | TCTCCTTCCC | ACTCGCCTTT | ACAGTTGAAA | 1480 |
| AGCTGACGGG | CAGTGGCGAG | CTGTGGTGGC | AGGCGGAGAG | 1520 |
| GGCTTCCTCC | TCCAAGTCTT | GGATCATCTT | TGACCTGAAG | 1560 |
| AACAAGGAAG | TGTCTGTAAA | ACGGGTTACC | CAGGACCCTA | 1600 |
| AGCTCCAGAT | GGGCAAGAAG | CTCCGCTCC | ACCTCACCCT | 1640 |
| GCCCCAGGCC | TTGCCTCAGT | ATGCTGGCTC | TGGAAACCTC | 1680 |
| ACCCTGGCCC | TTGAAGCGAA | AACAGGAAAG | TTGCATCAGG | 1720 |
| AAGTGAACCT | GGTGGTGATG | AGAGCCACTC | AGCTCCAGAA | 1760 |
| AAATTTGACC | TGTGAGGTGT | GGGGACCCAC | CTCCCCTAAG | 1800 |
| CTGATGCTGA | GCTTGAAACT | GGAGAACAAG | GAGGCAAAGG | 1840 |
| TCTCGAAGCG | GGAGAAGGCG | GTGTGGGTGC | TGAACCCTGA | 1880 |
| GGCGGGGATG | TGGCAGTGTC | TGCTGAGTGA | CTCGGGACAG | 1920 |
| GTCCTGCTGG | AATCCAACAT | CAAGGTTCTG | CCCATATGGT | 1960 |
| CCACCCCAGT | GCAGCCAATG | TTATTCATAA | TGATAGTAGG | 2000 |
| AGGCTTGGTA | GGTTTAAGAA | TAGTTTTTGC | TGTACTTTCT | 2040 |

| | | | | |
|---|---|---|---|---|
| ATAGTGAATA | GAGTTAGGCA | GGGATATTCA | CCATTATCGT | 2080 |
| TTCAGACCCA | CCTCCCAATC | CCGAGGGGAC | CCGACAGGCC | 2120 |
| CGAAGGAATA | GAAGAAGAAG | GTGGAGAGAG | AGACAGAGAC | 2160 |
| AGATCCATTC | GATTAGTGAA | CGGATCCTTA | GCACTTATCT | 2200 |
| GGGACGATCT | GCGGAGCCTG | TGCCTCTTCA | GCTACCACCG | 2240 |
| CTTGAGAGAC | TTACTCTTGA | TTGTAACGAG | GATTGTGGAA | 2280 |
| CTTCTGGGAC | GCAGGGGGTG | GGAAGCCCTC | AAATATTGGT | 2320 |
| GGAATCTCCT | ACAGTATTGG | AGTCAGGAAC | TAAAGAATAG | 2360 |
| TGCTGTTAAC | TTGCTCAATG | CCACAGCCAT | AGCAGTAGCT | 2400 |
| GAGGGGACAG | ATAGGGTTAT | AGAAGTATTA | CAAGCAGCTT | 2440 |
| ATAGAGCTAT | TCGCCACATA | CCTAGAAGAA | TAAGACAGGG | 2480 |
| CTTGGAAAGG | ATTTTGCTAT | AAGCATATGG | TACATTGCTG | 2520 |
| ATGAGTCCGT | GAGGACGAAA | CTGTGCTGCG | GCCGCAGGAG | 2560 |
| CTTTGTTCCT | TGGGTTCTTG | GGAGCAGCAG | GAAGCACTAT | 2600 |
| GGGCTGCACG | TCAATGACGC | TGACGGTACA | GGCCAGACAA | 2640 |
| TTATTGTCTG | ATATAGTGCA | GCAGCAGAAC | AATTTGCTGA | 2680 |
| GGGCTATTGA | GGCGCAACAG | CATCTGTTGC | AACTCACAGT | 2720 |
| CTGGGGCATC | AAACAGCTCC | AGGCAAGAAT | CCTGGCTGTG | 2760 |
| GAAAGATACC | TAAAGGACAA | CAGCTCCTGC | GGCCGCTATA | 2800 |
| AGGTGGCAAG | TGGTCAAAAA | GTAGTGTGAT | TGGATGGCCT | 2840 |
| GCTGTAAGGG | AAAGAATGAG | ACGAGCTGAG | CCAGCAGCAG | 2880 |
| ATGGGGTGGG | AGCAGTATCT | CGAGCCATAA | TACTGATGAG | 2920 |
| TCCGTGAGGA | CGAAACTGTG | ACGCGGCCGC | CTCGAGGCGC | 2960 |
| GCGCATGCCT | GCAGGTCGAC | GTTAATTTCT | GATGAGTCCG | 3000 |
| TGAGGACGAA | ACACATGGTG | CCATTTCTGA | TGAGTCCGTG | 3040 |
| AGGACGAAAC | AGCAGTGGGT | CTTGCTGATG | AGTCCGTGAG | 3080 |
| GACGAAACAA | TTAATTTTGC | TCCTGATGAG | TCCGTGAGGA | 3120 |
| CGAAACTAAT | GTGGATCCCA | TACTGATGAG | TCCGTGAGGA | 3160 |
| CGAAACTGAT | TAAATCGCAA | CTGATGAGTC | CGTGAGGACG | 3200 |
| AAACCAGCCG | TCCATGTGCT | GATGAGTCCG | TGAGGACGAA | 3240 |
| ACATTGTAGA | GGGGCACTGA | TGAGTCCGTG | AGGACGAAAC | 3280 |
| ATTGCTACGG | TACCTTTAAG | ACCAATGACT | TACAAGGCAG | 3320 |
| CTGTAGATCT | TAGCCACTTT | TTAAAAGAAA | AGGGGGGACT | 3360 |
| GGAAGGGCTA | ATTCACTCCC | AAAGAAGACA | AGATATCCTT | 3400 |
| GATCTGTGGA | TCTACCACAC | ACAAGGCTAC | TTCCCTGATT | 3440 |
| GGCAGAACTA | CACACCAGGG | CCAGGGGTCA | GATATCCACT | 3480 |
| GACCTTTGGA | TGGTGCTACA | AGCTAGTACC | AGTTGAGCCA | 3520 |
| GATAAGGTAG | AAGAGGCCAA | TAAAGGAGAG | AACACCAGCT | 3560 |
| TGTTACACCC | TGTGAGCCTG | CATGGAATGG | ATGACCCTGA | 3600 |
| GAGAGAAGTG | TTAGAGTGGA | GGTTTGACAG | CCGCCTAGCA | 3640 |

| | | | | |
|---|---|---|---|---|
| TTTCATCACG | TGGCCCGAGA | GCTGCATCCG | GAGTACTTCA | 3680 |
| AGAACTGCTG | ACATCGAGCT | TGCTACAAGG | GACTTTCCGC | 3720 |
| TGGGGACTTT | CCAGGGAGGC | GTGGCCTGGG | CGGGACTGGG | 3760 |
| GAGTGGCGAG | CCCTCAGATG | CTGCATATAA | GCAGCTGCTT | 3800 |
| TTTGCCTGTA | CTGGGTCTCT | CTGGTTAGAC | CAGATCTGAG | 3840 |
| CCTGGGAGCT | CTCTGGCTAA | CTAGGGAACC | CACTGCTTAA | 3880 |
| GCCTCAATAA | AGCTTGCCTT | GAGTGCTTCA | AGTAGTGTGT | 3920 |
| GCCCGTCTGT | TGTGTGACTC | TGGTAACTAG | AGATCCCTCA | 3960 |
| GACCCTTTTA | GTCAGTGTGG | AAAATCTCTA | GCA | 3993 |

( 2 ) INFORMATION FOR SEQ ID NO:7:

( i ) SEQUENCE CHARACTERISTICS:
        ( A ) LENGTH: 4059 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

| | | | | |
|---|---|---|---|---|
| TGGAAGGGCT | AATTTGGTCC | CAAAAAGAC | AAGAGATCCT | 40 |
| TGATCTGTGG | ATCTACCACA | CACAAGGCTA | CTTCCCTGAT | 80 |
| TGGCAGAACT | ACACACCAGG | GCCAGGGATC | AGATATCCAC | 120 |
| TGACCTTTGG | ATGGTGCTTC | AAGTTAGTAC | CAGTTGAACC | 160 |
| AGAGCAAGTA | GAAGAGGCCA | ATGAAGGAGA | GAACAACAGC | 200 |
| TTGTTACACC | CTATGAGCCA | GCATGGGATG | GAGGACCCGG | 240 |
| AGGGAGAAGT | ATTAGTGTGG | AAGTTTGACA | GCCTCCTAGC | 280 |
| ATTTCGTCAC | ATGGCCCGAG | AGCTGCATCC | GGAGTACTAC | 320 |
| AAAGACTGCT | GACATCGAGC | TTTCTACAAG | GGACTTTCCG | 360 |
| CTGGGGACTT | TCCAGGGAGG | TGTGGCCTGG | GCGGGACTGG | 400 |
| GGAGTGGCGA | GCCCTCAGAT | GCTACATATA | AGCAGCTGCT | 440 |
| TTTTGCCTGT | ACTGGGTCTC | TCTGGTTAGA | CCAGATCTGA | 480 |
| GCCTGGGAGC | TCTCTGGCTA | ACTAGGGAAC | CCACTGCTTA | 520 |
| AGCCTCAATA | AAGCTTGCCT | TGAGTGCTCA | AGTAGTGTG | 560 |
| TGCCCGTCTG | TTGTGTGACT | CTGGTAACTA | GAGATCCCTC | 600 |
| AGACCCTTTT | AGTCAGTGTG | GAAAATCTCT | AGCAGTGGCG | 640 |
| CCCGAACAGG | GACTTGAAAG | CGAAAGTAAA | GCCAGAGGAG | 680 |
| ATCTCTCGAC | GCAGGACTCG | GCTTGCTGAA | GCGCGCACGG | 720 |
| CAAGAGGCGA | GGGGCGGCGA | CTGGTGAGTA | CGCCAAAAAT | 760 |
| TTTGACTAGC | GGAGGCTAGA | AGGAGATTGG | GTGCGAGAGC | 800 |
| GTCGGTATTA | AGCGGGGGAG | AATTAGATAA | ATGGGAAAAA | 840 |
| ATTCGGTAAT | AGGAGATGAA | CCGGGGAGTC | CCTTTTAGTC | 880 |
| ACTTGCTTCT | GGTGCTGCAA | CTGGCGCTCC | TCCCAGCAGC | 920 |
| CACTCAGGGA | AAGAAAGTGG | TGCTGGGCAA | AAAAGGGGAT | 960 |
| ACAGTGGAAC | TGACCTGTAC | AGCTTCCCAG | AAGAAGAGCA | 1000 |

-continued

| | | | | |
|---|---|---|---|---|
| TACAATTCCA | CTGGAAAAAC | TCCAACCAGA | TAAAGATTCT | 1040 |
| GGGAAATCAG | GGCTCCTTCT | TAACTAAAGG | TCCATCCAAG | 1080 |
| CTGAATGATC | GCGCTGACTC | AAGAAGAAGC | CTTTGGGACC | 1120 |
| AAGGAAACTT | CCCCCTGATC | ATTAAGAATC | TTAAGATAGA | 1160 |
| AGACTCAGAT | ACTTACATCT | GTGAAGTGGA | GGACCAGAAG | 1200 |
| GAGGAGGTGC | AATTGCTAGT | GTTCGGATTG | ACTGCCAACT | 1240 |
| CTGACACCCA | CCTGCTTCAG | GGCAGAGCC | TGACCCTGAC | 1280 |
| CTTGGAGAGC | CCCCCTGGTA | GTAGCCCCTC | AGTGCAATGT | 1320 |
| AGGAGTCCAA | GGGGTAAAAA | CATACAGGGG | GGGAAGACCC | 1360 |
| TCTCCGTGTC | TCAGCTGGAG | CTCCAGGATA | GTGGCACCTG | 1400 |
| GACATGCACT | GTCTTGCAGA | ACCAGAAGAA | GGTGGAGTTC | 1440 |
| AAAATAGACA | TCGTGGTGCT | AGCTTTCCAG | AAGGCCTCCA | 1480 |
| GCATAGTCTA | TAAGAAAGAG | GGGGAACAGG | TGGAGTTCTC | 1520 |
| CTTCCCACTC | GCCTTTACAG | TTGAAAAGCT | GACGGGCAGT | 1560 |
| GGCGAGCTGT | GGTGGCAGGC | GGAGAGGGCT | TCCTCCTCCA | 1600 |
| AGTCTTGGAT | CATCTTTGAC | CTGAAGAACA | AGGAAGTGTC | 1640 |
| TGTAAAACGG | GTTACCCAGG | ACCCTAAGCT | CCAGATGGGC | 1680 |
| AAGAAGCTCC | CGCTCCACCT | CACCCTGCCC | CAGGCCTTGC | 1720 |
| CTCAGTATGC | TGGCTCTGGA | AACCTCACCC | TGGCCCTTGA | 1760 |
| AGCGAAAACA | GGAAAGTTGC | ATCAGGAAGT | GAACCTGGTG | 1800 |
| GTGATGAGAG | CCACTCAGCT | CCAGAAAAAT | TTGACCTGTG | 1840 |
| AGGTGTGGGG | ACCCACCTCC | CCTAAGCTGA | TGCTGAGCTT | 1880 |
| GAAACTGGAG | AACAAGGAGG | CAAAGGTCTC | GAAGCGGGAG | 1920 |
| AAGGCGGTGT | GGGTGCTGAA | CCCTGAGGCG | GGGATGTGGC | 1960 |
| AGTGTCTGCT | GAGTGACTCG | GGACAGGTCC | TGCTGGAATC | 2000 |
| CAACATCAAG | GTTCTGCCCA | TATGGTCCAC | CCCAGTGCAG | 2040 |
| CCAATGTTAT | TCATAATGAT | AGTAGGAGGC | TTGGTAGGTT | 2080 |
| TAAGAATAGT | TTTTGCTGTA | CTTTCTATAG | TGAATAGAGT | 2120 |
| TAGGCAGGGA | TATTCACCAT | TATCGTTTCA | GACCCACCTC | 2160 |
| CCAATCCCGA | GGGGACCCGA | CAGGCCCGAA | GGAATAGAAG | 2200 |
| AAGAAGGTGG | AGAGAGAGAC | AGAGACAGAT | CCATTCGATT | 2240 |
| AGTGAACGGA | TCCTTAGCAC | TTATCTGGGA | CGATCTGCGG | 2280 |
| AGCCTGTGCC | TCTTCAGCTA | CCACCGCTTG | AGAGACTTAC | 2320 |
| TCTTGATTGT | AACGAGGATT | GTGGAACTTC | TGGGACGCAG | 2360 |
| GGGGTGGGAA | GCCCTCAAAT | ATTGGTGGAA | TCTCCTACAG | 2400 |
| TATTGGAGTC | AGGAACTAAA | GAATAGTGCT | GTTAACTTGC | 2440 |
| TCAATGCCAC | AGCCATAGCA | GTAGCTGAGG | GGACAGATAG | 2480 |
| GGTTATAGAA | GTATTACAAG | CAGCTTATAG | AGCTATTCGC | 2520 |
| CACATACCTA | GAAGAATAAG | ACAGGGCTTG | GAAAGGATTT | 2560 |
| TGCTATAAGC | ATATGGTACA | TTGCTGATGA | GTCCGTGAGG | 2600 |

| | | | | |
|---|---|---|---|---|
| ACGAAACTGT | GCTGCGGCCG | CAGGAGCTTT | GTTCCTTGGG | 2640 |
| TTCTTGGGAG | CAGCAGGAAG | CACTATGGGC | TGCACGTCAA | 2680 |
| TGACGCTGAC | GGTACAGGCC | AGACAATTAT | TGTCTGATAT | 2720 |
| AGTGCAGCAG | CAGAACAATT | TGCTGAGGGC | TATTGAGGCG | 2760 |
| CAACAGCATC | TGTTGCAACT | CACAGTCTGG | GGCATCAAAC | 2800 |
| AGCTCCAGGC | AAGAATCCTG | GCTGTGGAAA | GATACCTAAA | 2840 |
| GGACAACAGC | TCCTGCGGCC | GCTATAAGGT | GGCAAGTGGT | 2880 |
| CAAAAGTAG | TGTGATTGGA | TGGCCTGCTG | TAAGGGAAAG | 2920 |
| AATGAGACGA | GCTGAGCCAG | CAGCAGATGG | GGTGGGAGCA | 2960 |
| GTATCTCGAG | CCATAATACT | GATGAGTCCG | TGAGGACGAA | 3000 |
| ACTGTGACGC | GGCCGCCTCG | AGGCGCGCGC | ATGCCTGCAG | 3040 |
| GTCGACGTTA | ATTTCTGATG | AGTCCGTGAG | GACGAAACAC | 3080 |
| ATGGTGCCAT | TTCTGATGAG | TCCGTGAGGA | CGAAACAGCA | 3120 |
| GTGGGTCTTG | CTGATGAGTC | CGTGAGGACG | AAACAATTAA | 3160 |
| TTTTGCTCCT | GATGAGTCCG | TGAGGACGAA | ACTAATGTGG | 3200 |
| ATCCCATACT | GATGAGTCCG | TGAGGACGAA | ACTGATTAAA | 3240 |
| TCGCAACTGA | TGAGTCCGTG | AGGACGAAAC | CAGCCGTCCA | 3280 |
| TGTGCTGATG | AGTCCGTGAG | GACGAAACAT | TGTAGAGGGG | 3320 |
| CACTGATGAG | TCCGTGAGGA | CGAAACATTG | CTACGGTACC | 3360 |
| TTTAAGACCA | ATGACTTACA | AGGCAGCTGT | AGATCTTAGC | 3400 |
| CACTTTTTAA | AAGAAAGGG | GGGACTGGAA | GGGCTAATTC | 3440 |
| ACTCCCAAAG | AAGACAAGAT | ATCCTTGATC | TGTGGATCTA | 3480 |
| CCACACACAA | GGCTACTTCC | CTGATTGGCA | GAACTACACA | 3520 |
| CCAGGGCCAG | GGGTCAGATA | TCCACTGACC | TTTGGATGGT | 3560 |
| GCTACAAGCT | AGTACCAGTT | GAGCCAGATA | AGGTAGAAGA | 3600 |
| GGCCAATAAA | GGAGAGAACA | CCAGCTTGTT | ACACCCTGTG | 3640 |
| AGCCTGCATG | GAATGGATGA | CCCTGAGAGA | GAAGTGTTAG | 3680 |
| AGTGGAGGTT | TGACAGCCGC | CTAGCATTTC | ATCACGTGGC | 3720 |
| CCGAGAGCTG | CATCCGGAGT | ACTTCAAGAA | CTGCTGACAT | 3760 |
| CGAGCTTGCT | ACAAGGGACT | TTCCGCTGGG | GACTTTCCAG | 3800 |
| GGAGGCGTGG | CCTGGGCGGG | ACTGGGGAGT | GGCGAGCCCT | 3840 |
| CAGATGCTGC | ATATAAGCAG | CTGCTTTTG | CCTGTACTGG | 3880 |
| GTCTCTCTGG | TTAGACCAGA | TCTGAGCCTG | GGAGCTCTCT | 3920 |
| GGCTAACTAG | GGAACCCACT | GCTTAAGCCT | CAATAAAGCT | 3960 |
| TGCCTTGAGT | GCTTCAAGTA | GTGTGTGCCC | GTCTGTTGTG | 4000 |
| TGACTCTGGT | AACTAGAGAT | CCCTCAGACC | CTTTTAGTCA | 4040 |
| GTGTGGAAAA | TCTCTAGCA | | | 4059 |

( 2 ) INFORMATION FOR SEQ ID NO:8:

( i ) SEQUENCE CHARACTERISTICS:
( A ) LENGTH: 4632 base pairs
( B ) TYPE: nucleic acid ( C ) STRANDEDNESS: single
( D ) TOPOLOGY: linear ( x i ) SEQUENCE DESCRIPTION: SEQ ID NO:8:

| | | | | |
|---|---|---|---|---|
| TGGAAGGGCT | AATTTGGTCC | CAAAAAAGAC | AAGAGATCCT | 40 |
| TGATCTGTGG | ATCTACCACA | CACAAGGCTA | CTTCCCTGAT | 80 |
| TGGCAGAACT | ACACACCAGG | GCCAGGGATC | AGATATCCAC | 120 |
| TGACCTTTGG | ATGGTGCTTC | AAGTTAGTAC | CAGTTGAACC | 160 |
| AGAGCAAGTA | GAAGAGGCCA | ATGAAGGAGA | GAACAACAGC | 200 |
| TTGTTACACC | CTATGAGCCA | GCATGGGATG | GAGGACCCGG | 240 |
| AGGGAGAAGT | ATTAGTGTGG | AAGTTTGACA | GCCTCCTAGC | 280 |
| ATTTCGTCAC | ATGGCCCGAG | AGCTGCATCC | GGAGTACTAC | 320 |
| AAAGACTGCT | GACATCGAGC | TTTCTACAAG | GGACTTTCCG | 360 |
| CTGGGGACTT | TCCAGGGAGG | TGTGGCCTGG | GCGGGACTGG | 400 |
| GGAGTGGCGA | GCCCTCAGAT | GCTACATATA | AGCAGCTGCT | 440 |
| TTTTGCCTGT | ACTGGGTCTC | TCTGGTTAGA | CCAGATCTGA | 480 |
| GCCTGGGAGC | TCTCTGGCTA | ACTAGGGAAC | CCACTGCTTA | 520 |
| AGCCTCAATA | AAGCTTGCCT | TGAGTGCTCA | AAGTAGTGTG | 560 |
| TGCCCGTCTG | TTGTGTGACT | CTGGTAACTA | GAGATCCCTC | 600 |
| AGACCCTTTT | AGTCAGTGTG | GAAAATCTCT | AGCAGTGGCG | 640 |
| CCCGAACAGG | GACTTGAAAG | CGAAAGTAAA | GCCAGAGGAG | 680 |
| ATCTCTCGAC | GCAGGACTCG | GCTTGCTGAA | GCGCGCACGG | 720 |
| CAAGAGGCGA | GGGGCGGCGA | CTGGTGAGTA | CGCCAAAAAT | 760 |
| TTTGACTAGC | GGAGGCTAGA | AGGAGATTGG | GTGCGAGAGC | 800 |
| GTCGGTATTA | AGCGGGGGAG | AATTAGATAA | ATGGGAAAAA | 840 |
| ATTCGGTTAA | GGCCAGGGGG | AAAGAAACAA | TATAAACTAA | 880 |
| AACATATAGT | ATGGGCAAGC | AGGGAGCTAG | AACGATTCGC | 920 |
| AGTTAATCCT | GGCCTTTTAG | AGACATGAGA | AGGCTGTAGA | 960 |
| CAAATACTGG | GACAGCTACA | ACCATCCCTT | CAGACAGGAT | 1000 |
| CAGAAGAACT | TAGATCATTA | TATAATACAA | TAGCAGTCCT | 1040 |
| CTATTGTGTG | CATCAAAGGA | TAGATGTAAA | AGACACCAAG | 1080 |
| GAAGCCTTAG | ATAAGATATA | GGAAGAGCAA | AACAAAAGTA | 1120 |
| AGAAAAAGGC | ACAGCAAGCA | GCAGCTGACA | CAGGAAACAA | 1160 |
| CAGCCAGGTC | AGCCAAAATT | ACCCTATAGT | GCAGAACCTC | 1200 |
| CAGGGGCAAA | TGGTACATTA | GGCCATATCA | CCTAGAACTT | 1240 |
| TAAATGCATG | GGTAAAAGTA | GTAGAAGAGA | AGGCTTTCAG | 1280 |
| CCCAGAAGTA | ATACCCATGT | TTTCAGCATT | ATCAGAAGGA | 1320 |
| GCCACCCCAC | AAGATTTAAA | TACCATGCTA | AACACAGTGG | 1360 |
| GGGGACATTA | AGCAGCCATG | CAAATGTTAA | AAGAGACCAT | 1400 |
| CAATGAGGAA | GCTGCAGAAT | AATAGGAGAT | GAACCGGGGA | 1440 |
| GTCCCTTTTA | GTCACTTGCT | TCTGGTGCTG | CAACTGGCGC | 1480 |
| TCCTCCCAGC | AGCCACTCAG | GGAAAGAAAG | TGGTGCTGGG | 1520 |

-continued

| | | | | |
|---|---|---|---|---|
| CAAAAAAGGG | GATACAGTGG | AACTGACCTG | TACAGCTTCC | 1560 |
| CAGAAGAAGA | GCATACAATT | CCACTGGAAA | AACTCCAACC | 1600 |
| AGATAAAGAT | TCTGGGAAAT | CAGGGCTCCT | TCTTAACTAA | 1640 |
| AGGTCCATCC | AAGCTGAATG | ATCGCGCTGA | CTCAAGAAGA | 1680 |
| AGCCTTTGGG | ACCAAGGAAA | CTTCCCCCTG | ATCATTAAGA | 1720 |
| ATCTTAAGAT | AGAAGACTCA | GATACTTACA | TCTGTGAAGT | 1760 |
| GGAGGACCAG | AAGGAGGAGG | TGCAATTGCT | AGTGTTCGGA | 1800 |
| TTGACTGCCA | ACTCTGACAC | CCACCTGCTT | CAGGGGCAGA | 1840 |
| GCCTGACCCT | GACCTTGGAG | AGCCCCCTG | GTAGTAGCCC | 1880 |
| CTCAGTGCAA | TGTAGGAGTC | CAAGGGGTAA | AAACATACAG | 1920 |
| GGGGGGAAGA | CCCTCTCCGT | GTCTCAGCTG | GAGCTCCAGG | 1960 |
| ATAGTGGCAC | CTGGACATGC | ACTGTCTTGC | AGAACCAGAA | 2000 |
| GAAGGTGGAG | TTCAAAATAG | ACATCGTGGT | GCTAGCTTTC | 2040 |
| CAGAAGGCCT | CCAGCATAGT | CTATAAGAAA | GAGGGGGAAC | 2080 |
| AGGTGGAGTT | CTCCTTCCCA | CTCGCCTTTA | CAGTTGAAAA | 2120 |
| GCTGACGGGC | AGTGGCGAGC | TGTGGTGGCA | GGCGGAGAGG | 2160 |
| GCTTCCTCCT | CCAAGTCTTG | GATCATCTTT | GACCTGAAGA | 2200 |
| ACAAGGAAGT | GTCTGTAAAA | CGGGTTACCC | AGGACCCTAA | 2240 |
| GCTCCAGATG | GGCAAGAAGC | TCCCGCTCCA | CCTCACCCTG | 2280 |
| CCCCAGGCCT | TGCCTCAGTA | TGCTGGCTCT | GGAAACCTCA | 2320 |
| CCCTGGCCCT | TGAAGCGAAA | ACAGGAAAGT | TGCATCAGGA | 2360 |
| AGTGAACCTG | GTGGTGATGA | GAGCCACTCA | GCTCCAGAAA | 2400 |
| AATTTGACCT | GTGAGGTGTG | GGACCCACC | TCCCCTAAGC | 2440 |
| TGATGCTGAG | CTTGAAACTG | GAGAACAAGG | AGGCAAAGGT | 2480 |
| CTCGAAGCGG | GAGAAGGCGG | TGTGGGTGCT | GAACCCTGAG | 2520 |
| GCGGGGATGT | GGCAGTGTCT | GCTGAGTGAC | TCGGGACAGG | 2560 |
| TCCTGCTGGA | ATCCAACATC | AAGGTTCTGC | CCATATGGTC | 2600 |
| CACCCCAGTG | CAGCCAATGT | TATTCATAAT | GATAGTAGGA | 2640 |
| GGCTTGGTAG | GTTTAAGAAT | AGTTTTTGCT | GTACTTTCTA | 2680 |
| TAGTGAATAG | AGTTAGGCAG | GGATATTCAC | CATTATCGTT | 2720 |
| TCAGACCCAC | CTCCCAATCC | CGAGGGGACC | CGACAGGCCC | 2760 |
| GAAGGAATAG | AAGAAGAAGG | TGGAGAGAGA | GACAGAGACA | 2800 |
| GATCCATTCG | ATTAGTGAAC | GGATCCTTAG | CACTTATCTG | 2840 |
| GGACGATCTG | CGGAGCCTGT | GCCTCTTCAG | CTACCACCGC | 2880 |
| TTGAGAGACT | TACTCTTGAT | TGTAACGAGG | ATTGTGGAAC | 2920 |
| TTCTGGGACG | CAGGGGTGG | GAAGCCCTCA | AATATTGGTG | 2960 |
| GAATCTCCTA | CAGTATTGGA | GTCAGGAACT | AAAGAATAGT | 3000 |
| GCTGTTAACT | TGCTCAATGC | CACAGCCATA | GCAGTAGCTG | 3040 |
| AGGGGACAGA | TAGGGTTATA | GAAGTATTAC | AAGCAGCTTA | 3080 |
| TAGAGCTATT | CGCCACATAC | CTAGAAGAAT | AAGACAGGGC | 3120 |

-continued

```
TTGGAAAGGA  TTTTGCTATA  AGCATATGGT  ACATTGCTGA                    3160
TGAGTCCGTG  AGGACGAAAC  TGTGCTGCGG  CCGCAGGAGC                    3200
TTTGTTCCTT  GGGTTCTTGG  GAGCAGCAGG  AAGCACTATG                    3240
GGCTGCACGT  CAATGACGCT  GACGGTACAG  GCCAGACAAT                    3280
TATTGTCTGA  TATAGTGCAG  CAGCAGAACA  ATTTGCTGAG                    3320
GGCTATTGAG  GCGCAACAGC  ATCTGTTGCA  ACTCACAGTC                    3360
TGGGGCATCA  AACAGCTCCA  GGCAAGAATC  CTGGCTGTGG                    3400
AAAGATACCT  AAAGGACAAC  AGCTCCTGCG  GCCGCTATAA                    3440
GGTGGCAAGT  GGTCAAAAAG  TAGTGTGATT  GGATGGCCTG                    3480
CTGTAAGGGA  AAGAATGAGA  CGAGCTGAGC  CAGCAGCAGA                    3520
TGGGGTGGGA  GCAGTATCTC  GAGCCATAAT  ACTGATGAGT                    3560
CCGTGAGGAC  GAAACTGTGA  CGCGGCCGCC  TCGAGGCGCG                    3600
CGCATGCCTG  CAGGTCGACG  TTAATTTCTG  ATGAGTCCGT                    3640
GAGGACGAAA  CACATGGTGC  CATTTCTGAT  GAGTCCGTGA                    3680
GGACGAAACA  GCAGTGGGTC  TTGCTGATGA  GTCCGTGAGG                    3720
ACGAAACAAT  TAATTTTGCT  CCTGATGAGT  CCGTGAGGAC                    3760
GAAACTAATG  TGGATCCCAT  ACTGATGAGT  CCGTGAGGAC                    3800
GAAACTGATT  AAATCGCAAC  TGATGAGTCC  GTGAGGACGA                    3840
AACCAGCCGT  CCATGTGCTG  ATGAGTCCGT  GAGGACGAAA                    3880
CATTGTAGAG  GGGCACTGAT  GAGTCCGTGA  GGACGAAACA                    3920
TTGCTACGGT  ACCTTTAAGA  CCAATGACTT  ACAAGGCAGC                    3960
TGTAGATCTT  AGCCACTTTT  TAAAGAAAA   GGGGGGACTG                    4000
GAAGGGCTAA  TTCACTCCCA  AGAAGACAA   GATATCCTTG                    4040
ATCTGTGGAT  CTACCACACA  CAAGGCTACT  TCCCTGATTG                    4080
GCAGAACTAC  ACACCAGGGC  CAGGGGTCAG  ATATCCACTG                    4120
ACCTTTGGAT  GGTGCTACAA  GCTAGTACCA  GTTGAGCCAG                    4160
ATAAGGTAGA  AGAGGCCAAT  AAAGGAGAGA  ACACCAGCTT                    4200
GTTACACCCT  GTGAGCCTGC  ATGGAATGGA  TGACCCTGAG                    4240
AGAGAAGTGT  TAGAGTGGAG  GTTTGACAGC  CGCCTAGCAT                    4280
TTCATCACGT  GGCCCGAGAG  CTGCATCCGG  AGTACTTCAA                    4320
GAACTGCTGA  CATCGAGCTT  GCTACAAGGG  ACTTTCCGCT                    4360
GGGGACTTTC  CAGGGAGGCG  TGGCCTGGGC  GGGACTGGGG                    4400
AGTGGCGAGC  CCTCAGATGC  TGCATATAAG  CAGCTGCTTT                    4440
TTGCCTGTAC  TGGGTCTCTC  TGGTTAGACC  AGATCTGAGC                    4480
CTGGGAGCTC  TCTGGCTAAC  TAGGGAACCC  ACTGCTTAAG                    4520
CCTCAATAAA  GCTTGCCTTG  AGTGCTTCAA  GTAGTGTGTG                    4560
CCCGTCTGTT  GTGTGACTCT  GGTAACTAGA  GATCCCTCAG                    4600
ACCCTTTTAG  TCAGTGTGGA  AAATCTCTAG  CA                            4632
```

( 2 ) INFORMATION FOR SEQ ID NO:9:

( i ) SEQUENCE CHARACTERISTICS:
  ( A ) LENGTH: 7399 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:9:

| | | | | |
|---|---|---|---|---|
| TGGAAGGGCT | AATTTGGTCC | CAAAAAAGAC | AAGAGATCCT | 40 |
| TGATCTGTGG | ATCTACCACA | CACAAGGCTA | CTTCCCTGAT | 80 |
| TGGCAGAACT | ACACACCAGG | GCCAGGGATC | AGATATCCAC | 120 |
| TGACCTTTGG | ATGGTGCTTC | AAGTTAGTAC | CAGTTGAACC | 160 |
| AGAGCAAGTA | GAAGAGGCCA | ATAAGGAGA | GAAGAACAGC | 200 |
| TTGTTACACC | CTATGAGCCA | GCATGGGATG | GAGGACCCGG | 240 |
| AGGGAGAAGT | ATTAGTGTGG | AAGTTTGACA | GCCTCCTAGC | 280 |
| ATTTCGTCAC | ATGGCCCGAG | AGCTGCATCC | GGAGTACTAC | 320 |
| AAAGACTGCT | GACATCGAGC | TTTCTACAAG | GGACTTTCCG | 360 |
| CTGGGGACTT | TCCAGGGAGG | TGTGGCCTGG | GCGGGACTGG | 400 |
| GGAGTGGCGA | GCCCTCAGAT | GCTACATATA | AGCAGCTGCT | 440 |
| TTTTGCCTGT | ACTGGGTCTC | TCTGGTTAGA | CCAGATCTGA | 480 |
| GCCTGGGAGC | TCTCTGGCTA | ACTAGGGAAC | CCACTGCTTA | 520 |
| AGCCTCAATA | AAGCTTGCCT | TGAGTGCTCA | AAGTAGTGTG | 560 |
| TGCCCGTCTG | TTGTGTGACT | CTGGTAACTA | GAGATCCCTC | 600 |
| AGACCCTTTT | AGTCAGTGTG | GAAAATCTCT | AGCAGTGGCG | 640 |
| CCCGAACAGG | GACTTGAAAG | CGAAAGTAAA | GCCAGAGGAG | 680 |
| ATCTCTCGAC | GCAGGACTCG | GCTTGCTGAA | GCGCGCACGG | 720 |
| CAAGAGGCGA | GGGGCGGCGA | CTGGTGAGAG | ATGGGTGCGA | 760 |
| GAGCGTCGGT | ATTAAGCGGG | GGAGAATTAG | ATAAATGGGA | 800 |
| AAAAATTCGG | TTAAGGCCAG | GGGGAAAGAA | ACAATATAAA | 840 |
| CTAAAACATA | TAGTATGGGC | AAGCAGGGAG | CTAGAACGAT | 880 |
| TCGCAGTTAA | TCCTGGCCTT | TTAGAGACAT | CAGAAGGCTG | 920 |
| TAGACAAATA | CTGGGACAGC | TACAACCATC | CCTTCAGACA | 960 |
| GGATCAGAAG | AACTTAGATC | ATTATATAAT | ACAATAGCAG | 1000 |
| TCCTCTATTG | TGTGCATCAA | AGGATAGATG | TAAAAGACAC | 1040 |
| CAAGGAAGCC | TTAGATAAGA | TAGAGGAAGA | GCAAAACAAA | 1080 |
| AGTAAGAAAA | AGGCACAGCA | AGCAGCAGCT | GACACAGGAA | 1120 |
| ACAACAGCCA | GGTCAGCCAA | AATTACCCTA | TAGTGCAGAA | 1160 |
| CCTCCAGGGG | CAAATGGTAC | ATCAGGCCAT | ATCACCTAGA | 1200 |
| ACTTTAAATG | CATGGGTAAA | AGTAGTAGAA | GAGAAGGCTT | 1240 |
| TCAGCCCAGA | AGTAATACCC | ATGTTTTCAG | CATTATCAGA | 1280 |
| AGGAGCCACC | CCACAAGATT | TAAATACCAT | GCTAAACACA | 1320 |
| GTGGGGGGAC | ATCAAGCAGC | CATGCAAATG | TTAAAAGAGA | 1360 |
| CCATCAATGA | GGAAGCTGCA | GAATGGGATA | GATTGCATCC | 1400 |
| AGTGCATGCA | GGGCCTATTG | CACCAGGCCA | GATGAGAGAA | 1440 |

| | | | | |
|---|---|---|---|---|
| CCAAGGGGAA | GTGACATAGC | AGGAACTACT | AGTACCCTTC | 1480 |
| AGGAACAAAT | AGGATGGATG | ACACATAATC | CACCTATCCC | 1520 |
| AGTAGGAGAA | ATCTATAAAA | GATGGATAAT | CCTGGGATTA | 1560 |
| AATAAAATAG | TAAGAATGTA | TAGCCCTACC | AGCATTCTGG | 1600 |
| ACATAAGACA | AGGACCAAAG | GAACCCTTTA | GAGACTATGT | 1640 |
| AGACCGATTC | TATAAAACTC | TAAGAGCCGA | GCAAGCTTCA | 1680 |
| CAAGAGGTAA | AAAATTGGAT | GACAGAAACC | TTGTTGGTCC | 1720 |
| AAAATGCGAA | CCCAGATTGT | AAGACTATTT | TAAAAGCATT | 1760 |
| GGGACCAGGA | GCGACACTAG | AAGAAATGAT | GACAGCATGT | 1800 |
| CAGGGAGTGG | GGGGACCCGG | CCATAAAGCA | AGAGTTTTGG | 1840 |
| CTGAAGCAAT | GAGCCAAGTA | ACAAATCCAG | CTACCATAAT | 1880 |
| GATACAGAAA | GGCAATTTTA | GGAACCAAAG | AAAGACTGTT | 1920 |
| AAGTGTTTCA | ATTGTGGCAA | AGAAGGGCAC | ATAGCCAAAA | 1960 |
| ATTGCAGGGC | CCCTAGGAAA | AAGGGCTGTT | GGAAATGTGG | 2000 |
| AAAGGAAGGA | CACCAAATGA | AAGATTGTAC | TGAGAGACAG | 2040 |
| GCTAATTTTT | TAGGGAAGAT | CTGGCCTTCC | CACAAGGGAA | 2080 |
| GGCCAGGGAA | TTTTCTTCAG | AGCAGACCAG | AGCCAACAGC | 2120 |
| CCCACCAGAA | GAGAGCTTCA | GGTTTGGGGA | AGAGACAACA | 2160 |
| ACTCCCTCTC | AGAAGCAGGA | GCCGATAGAC | AAGGAACTGT | 2200 |
| ATCCTTTAGC | TTCCCTCAGA | TCACTCTTTG | GCAGCGACCC | 2240 |
| CTCGTCACAA | TAAAGATAGG | GGGGCAATTA | AAGGAAGCTC | 2280 |
| TATTAGATAC | AGGAGCAGAT | GATACAGTAT | TAGAAGAAAT | 2320 |
| GAATTTGCCA | GGAAGATGGA | AACCAAAAAT | GATAGGGGGA | 2360 |
| ATTGGAGGTT | TTATCAAAGT | AGGACAGTAT | GATCAGATAC | 2400 |
| TCATAGAAAT | CTGCGGACAT | AAAGCTATAG | GTACAGTATT | 2440 |
| AGTAGGACCT | ACACCTGTCA | ACATAATTGG | AAGAAATCTG | 2480 |
| TTGACTCAGA | TTGGCTGCAC | TTTAAATTTT | CCCATTAGTC | 2520 |
| CTATTGAGAC | TGTACCAGTA | AAATTAAAGC | CAGGAATGGA | 2560 |
| TGGCCCAAAA | GTTAAACAAT | GGCCATTGAC | AGAAGAAAAA | 2600 |
| ATAAAAGCAT | TAGTAGAAAT | TTGTACAGAA | ATGGAAAAGG | 2640 |
| AAGGAAAAAT | TTCAAAAATT | GGGCCTGAAA | ATCCATACAA | 2680 |
| TACTCCAGTA | TTTGCCATAA | AGAAAAAAGA | CAGTACTAAA | 2720 |
| TGGAGAAAAT | TAGTAGATTT | CAGAGAACTT | AATAAGAGAA | 2760 |
| CTCAAGATTT | CTGGGAAGTT | CAATTAGGAA | TACCACATCC | 2800 |
| TGCAGGGTTA | AAACAGAAAA | AATCAGTAAC | AGTACTGGAT | 2840 |
| GTGGGCGATG | CATATTTTTC | AGTTCCCTTA | GATAAAGACT | 2880 |
| TCAGGAAGTA | TACTGCATTT | ACCATACCTA | GTATAAACAA | 2920 |
| TGAGACACCA | GGGATTAGAT | ATCAGTACAA | TGTGCTTCCA | 2960 |
| CAGGGATGGA | AAGGATCACC | AGCAATATTC | CAGTGTAGCA | 3000 |
| TGACAAAAAT | CTTAGAGCCT | TTTAGAAAAC | AAAATCCAGA | 3040 |

```
CATAGTCATC TATCAATACA TGGATGATTT GTATGTAGGA                    3080

TCTGACTTAG AAATAGGGCA GCATAGAACA AAAATAGAGG                    3120

AACTGAGACA ACATCTGTTG AGGTGGGGAT TTACCACACC                    3160

AGACAAAAAA CATCAGAAAG AACCTCCATT CCTTTGGATG                    3200

GGTTATGAAC TCCATCCTGA TAAATGGACA GTACAGCCTA                    3240

TAGTGCTGCC AGAAAAGGAC AGCTGGACTG TCAATGACAT                    3280

ACAGAAATTA GTGGGAAAAT TGAATTGGGC AAGTCAGATT                    3320

TATGCAGGGA TTAAAGTAAG GCAATTATGT AAACTTCTTA                    3360

GGGGAACCAA AGCACTAACA GAAGTAGTAC CACTAACAGA                    3400

AGAAGCAGAG CTAGAACTGG CAGAAAACAG GGAGATTCTA                    3440

AAAGAACCGG TACATGGAGT GTATTATGAC CCATCAAAAG                    3480

ACTTAATAGC AGAAATACAG AAGCAGGGGC AAGGCCAATG                    3520

GACATATCAA ATTTATCAAG AGCCATTTAA AAATCTGAAA                    3560

ACAGGAAAAT ATGCAAGAAT GAAGGGTGCC CACACTAATG                    3600

ATGTGAAACA ATTAACAGAG GCAGTACAAA AAATAGCCAC                    3640

AGAAAGCATA GTAATATGGG AAAAGACTCC TAAATTTAAA                    3680

TTACCCATAC AAAAGGAAAC ATGGGAAGCA TGGTGGACAG                    3720

AGTATTGGCA AGCCACCTGG ATTCCTGAGT GGGAGTTTGT                    3760

CAATACCCCT CCCTTAGTGA AGTTATGGTA CCAGTTAGAG                    3800

AAAGAACCCA TAATAGGAGC AGAAACTTTC TATGTAGATG                    3840

GGGCAGCCAA TAGGGAAACT AAATTAGGAA AAGCAGGATA                    3880

TGTAACTGAC AGAGGAAGAC AAAAAGTTGT CCCCCTAACG                    3920

GACACAACAA ATCAGAAGAC TGAGTTACAA GCAATTCATC                    3960

TAGCTTTGCA GGATTCGGGA TTAGAAGTAA ACATAGTGAC                    4000

AGACTCACAA TATGCATTGG GAATCATTCA AGCACAACCA                    4040

GATAAGAGTG AATCAGAGTT AGTCAGTCAA ATAATAGAGC                    4080

AGTTAATAAA AAAGGAAAAA GTCTACCTGG CATGGGTACC                    4120

AGCACACAAA GGAATTGGAG GAAATGAACA AGTAGATGGG                    4160

TTGGTCAGTG CTGGAATCAG GAAAGTACTA TTTTTAGATG                    4200

GAATAGATAA GGCCCAAGAA GAACATGAGA AATATCACAG                    4240

TAATTGGAGA GCAATGGCTA GTGATTTTAA CCTACCACCT                    4280

GTAGTAGCAA AAGAAATAGT AGCCAGCTGT GATAAATGTC                    4320

AGCTAAAAGG GGAAGCCATG CATGGACAAG TAGACTGTAG                    4360

CCCAGGAATA TGGCAGCTAG ATTGTACACA TTTAGAAGGA                    4400

AAAGTTATCT TGGTAGCAGT TCATGTAGCC AGTGGATATA                    4440

TAGAAGCAGA AGTAATTCCA GCAGAGACAG GGCAAGAAAC                    4480

AGCATACTTC CTCTTAAAAT TAGCAGGAAG ATGGCCAGTA                    4520

AAAACAGTAC ATACAGACAA TGGCAGCAAT TCACCAGTA                     4560

CTACAGTTAA GGCCGCCTGT TGGTGGGCGG GGATCAAGCA                    4600

GGAATTTGGC ATTCCCTACA ATCCCCAAAG TCAAGGAGTA                    4640
```

| | | | | |
|---|---|---|---|---|
| ATAGAATCTA | TGAATAAAGA | ATTAAAGAAA | ATTATAGGAC | 4680 |
| AGGTAAGAGA | TCAGGCTGAA | CATCTTAAGA | CAGCAGTACA | 4720 |
| AATGGCAGTA | TTCATCCACA | ATTTTAAAAG | AAAAGGGGGG | 4760 |
| ATTGGGGGGT | ACAGTGCAGG | GGAAAGAATA | GTAGACATAA | 4800 |
| TAGCAACAGA | CATACAAACT | AAAGAATTAC | AAAAACAAAT | 4840 |
| TACAAAAATT | CAAAATTTTC | GGGTTTATTA | CAGGGACAGC | 4880 |
| AGAGATCCAG | TTTGGAAAGG | ACCAGCAAAG | CTCCTCTGGA | 4920 |
| AAGGTGAAGG | GGCAGTAGTA | ATACAAGATA | ATAGTGACAT | 4960 |
| AAAAGTAGTG | CCAAGAAGAA | AAGCAAAGAT | CATCAGGGAT | 5000 |
| TATGGAAAAC | AGATGGCAGG | TGATGATTGT | GTGGCAAGTA | 5040 |
| GACAGGATGA | GGATTAACAC | ATGGAAAAGA | TTAGTAAAAC | 5080 |
| ACCATATGTA | TATTTCAAGG | AAAGCTAAGG | ACTGGTTTTA | 5120 |
| TAGACATCAC | TATGAAAGTA | CTAATCCAAA | AATAAGTTCA | 5160 |
| GAAGTACACA | TCCCACTAGG | GGATGCTAAA | TTAGTAATAA | 5200 |
| CAACATATTG | GGGTCTGCAT | ACAGGAGAAA | GAGACTGGCA | 5240 |
| TTTGGGTCAG | GGAGTCTCCA | TAGAATGGAG | GAAAAAGAGA | 5280 |
| TATAGCACAC | AAGTAGACCC | TGACCTAGCA | GACCAACTAA | 5320 |
| TTCATCTGCA | CTATTTTGAT | TGTTTTTCAG | AATCTGCTAT | 5360 |
| AAGAAATACC | ATATTAGGAC | GTATAGTTAG | TCCTAGGTGT | 5400 |
| GAATATCAAG | CAGGACATAA | CAAGGTAGGA | TCTCTACAGT | 5440 |
| ACTTGGCACT | AGCAGCATTA | ATAAAACCAA | AACAGATAAA | 5480 |
| GCCACCTTTG | CCTAGTGTTA | GGAAACTGAC | AGAGGACAGA | 5520 |
| TGGAACAAGC | CCCAGAAGAC | CAAGGGCCAC | AGAGGGAGCC | 5560 |
| ATACAATGAA | TGGACACTAG | AGCTTTTAGA | GGAACTTAAG | 5600 |
| AGTGAAGCTG | TTAGACATTT | TCCTAGGATA | TGGCTCCATA | 5640 |
| ACTTAGGACA | ACATATCTAT | GAAACTTACG | GGGATACTTG | 5680 |
| GGCAGGAGTG | GAAGCCATAA | TAAGAATTCT | GCAACAACTG | 5720 |
| CTGTTTATCC | ATTTCAGAAT | TGGGTGTCGA | CATAGCAGAA | 5760 |
| TAGGCGTTAC | TCGACAGAGG | AGAGCAAGAA | ATGGAGCCAG | 5800 |
| TAGATCCTAG | ACTAGAGCCC | TGGAAGCATC | CAGGAAGTCA | 5840 |
| GCCTAAAACT | GCTTGTACCA | ATTGCTATTG | TAAAAAGTGT | 5880 |
| TGCTTTCATT | GCCAAGTTTG | TTTCATGACA | AAAGCCTTAG | 5920 |
| GCATCTCCTA | TGGCAGGAAG | AAGCGGAGAC | AGCGACGAAG | 5960 |
| AGCTCATCAG | AACAGTCAGA | CTCATCAAGC | TTCTCTATCA | 6000 |
| AAGCAGTAAG | TAGTACATGT | AATGCAACCT | ATAATAGTAG | 6040 |
| CAATAGTAGC | ATTAGTAGTA | GCAATAATAA | TAGCAATAGT | 6080 |
| TGTGTGGTCC | ATAGTAATCA | TAGAATATAG | GAAAATATTA | 6120 |
| AGACAAAGAA | AAATAGACAG | GTTAATTGAT | AGACTAATAG | 6160 |
| AAAGAGCAGA | AGACAGTGGC | AATGAGAGTG | AAGGAGAAGT | 6200 |
| ATCAGCACTT | GTGGAGATGG | GGGTGGAAAT | GGGGCACCAT | 6240 |

| | | | | |
|---|---|---|---|---|
| GCTCCTTGGG | ATATTGATGA | TCTGTAGAAT | AGGAGCTTTG | 6280 |
| TTCCTTGGGT | TCTTGGGAGC | AGCAGGAAGC | ACTATGGGCT | 6320 |
| GCACGTCAAT | GACGCTGACG | GTACAGGCCA | GACAATTATT | 6360 |
| GTCTGATATA | GTGCAGCAGC | AGAACAATTT | GCTGAGGGCT | 6400 |
| ATTGAGGCGC | AACAGCATCT | GTTGCAACTC | ACAGTCTGGG | 6440 |
| GCATCAAACA | GCTCCAGGCA | AGAATCCTGG | CTGTGGAAAG | 6480 |
| ATACCTAAAG | GATCAACAGC | TCCTGGGGAT | TTGGGGTTGC | 6520 |
| TCTGGAAAAC | TCATTTGCAC | CACTGCTGTG | CCTTGGAATG | 6560 |
| CTAGTTGGAG | TAATAAATCT | CTGGAACAGA | TTTGGAATAA | 6600 |
| CATGACCTGG | ATGGAGTGGG | ACAGAGAAAT | TAACAATTAC | 6640 |
| ACAAGCTTAA | TACACTCCTT | AATTGAAGAA | TCGCAAAACC | 6680 |
| AGCAAGAAAA | GAATGAACAA | GAATTATTGG | AATTAGATAA | 6720 |
| ATGGGCAAGT | TTGTGGAATT | GGTTTAACAT | AACAAATTGG | 6760 |
| CTGTGGTATA | TAAAATTATT | CATAATGATA | GTAGGAGGCT | 6800 |
| TGGTAGGTTT | AAGAATAGTT | TTTGCTGTAC | TTTCTATAGT | 6840 |
| GAATAGAGTT | AGGCAGGGAT | ATTCACCATT | ATCGTTTCAG | 6880 |
| ACCCACCTCC | CAATCCCGAG | GGGACCCGAC | AGGCCCGAAG | 6920 |
| GAATAGAAGA | AGAAGGTGGA | GAGAGAGACA | GAGACAGATC | 6960 |
| CATTCGATTA | GTGAACGGAT | CCTTAGCACT | TATCTGGGAC | 7000 |
| GATCTGCGGA | GCCTGTGCCT | CTTCAGCTAC | CACCGCTTGA | 7040 |
| GAGACTTACT | CTTGATTGTA | ACGAGGATTG | TGGAACTTCT | 7080 |
| GGGACGCAGG | GGGTGGGAAG | CCCTCAAATA | TTGGTGGAAT | 7120 |
| CTCCTACAGT | ATTGGAGTCA | GGAACTAAAG | AATAGTGCTG | 7160 |
| TTAACATAAG | ATACATTGAT | GAGTTTGGAC | AAACCACAAC | 7200 |
| TAGAATGCAG | TGAAAAAAAT | GCTTTATTTG | TGAAATTTGT | 7240 |
| GATGCTATTG | CTTTATTTGT | AACCATTATA | AGCTGCAATA | 7280 |
| AACAAGTTAA | CAACAACAAT | TGCATTCATT | TTATGTTTCA | 7320 |
| GGTTCAGGGG | GAGGTGTGGG | AGGTTTTTTA | AAGCAAGTAA | 7360 |
| AACCTCTACA | AATGTGGTAT | GGCTGATTAT | GATGCTAGC | 7399 |

( 2 ) INFORMATION FOR SEQ ID NO:10:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

| | | | | |
|---|---|---|---|---|
| AAGCTTCATA | TGCCATAATA | CTGATGAGTC | CGTGAGGACG | 40 |
| AAACTGTGAC | GCGGCCGCCT | CGAG | | 64 |

( 2 ) INFORMATION FOR SEQ ID NO:11:

( i ) SEQUENCE CHARACTERISTICS:
        ( A ) LENGTH: 64 base pairs
        ( B ) TYPE: nucleic acid
        ( C ) STRANDEDNESS: single ( D ) TOPOLOGY: linear ( x i ) SEQUENCE DESCRIPTION: SEQ ID NO:11:

```
AAGCTTCATA  TGGTACATTG  CTGATGAGTC  CGTGAGGACG                    40
AAACTGTGCT  GCGGCCGCCT  CGAG                                      64
```

( 2 ) INFORMATION FOR SEQ ID NO:12:

( i ) SEQUENCE CHARACTERISTICS:
        ( A ) LENGTH: 410 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
AAGCTTCATA  TGCCATAATA  CTGATGAGTC  CGTGAGGACG                    40
AAACTGTGAC  GCGGCCGCCT  CGAGGCGCGC  GCATGCCTGC                    80
AGGTCGACGT  TAATTTCTGA  TGAGTCCGTG  AGGACGAAAC                   120
ACATGGTGCC  ATTTCTGATG  AGTCCGTGAG  GACGAAACAG                   160
CAGTGGGTCT  TGCTGATGAG  TCCGTGAGGA  CGAAACAATT                   200
AATTTTGCTC  CTGATGAGTC  CGTGAGGACG  AAACTAATGT                   240
GGATCCCATA  CTGATGAGTC  CGTGAGGACG  AAACTGATTA                   280
AATCGCAACT  GATGAGTCCG  TGAGGACGAA  ACCAGCCGTC                   320
CATGTGCTGA  TGAGTCCGTG  AGGACGAAAC  ATTGTAGAGG                   360
GGCACTGATG  AGTCCGTGAG  GACGAAACAT  TGCTACTAGT                   400
ACGCGAATTC                                                       410
```

( 2 ) INFORMATION FOR SEQ ID NO:13:

( i ) SEQUENCE CHARACTERISTICS:
        ( A ) LENGTH: 264 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
AAGCTTCATA  TGGTACATTG  CTGATGAGTC  CGTGAGGACG                    40
AAACTGTGCT  GCGGCCGCCT  CGAGGCGCGC  GCATGCCTGC                    80
AGGTCGACTC  TAGAGGATCC  CATACTGATG  AGTCCGTGAG                   120
GACGAAACTG  ATTAAATCGC  AACTGATGAG  TCCGTGAGGA                   160
CGAAACCAGC  CGTCCATGTG  CTGATGAGTC  CGTGAGGACG                   200
AAACATTGTA  GAGGGGCACT  GATGAGTCCG  TGAGGACGAA                   240
ACATTGCTAC  TAGTACGCGA  ATTC                                     264
```

( 2 ) INFORMATION FOR SEQ ID NO:14:

( i ) SEQUENCE CHARACTERISTICS:
        ( A ) LENGTH: 264 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
AAGCTTCATA  TGCCATAATA  CTGATGAGTC  CGTGAGGACG                    40
AAACTGTGAC  GCGGCCGCCT  CGAGGCGCGC  GCATGCCTGC                    80
```

```
AGGTCGACTC  TAGAGGATCC  CATACTGATG  AGTCCGTGAG                    120

GACGAAACTG  ATTAAATCGC  AACTGATGAG  TCCGTGAGGA                    160

CGAAACCAGC  CGTCCATGTG  CTGATGAGTC  CGTGAGGACG                    200

AAACATTGTA  GAGGGGCACT  GATGAGTCCG  TGAGGACGAA                    240

ACATTGCTAC  TAGTACGCGA  ATTC                                      264
```

( 2 ) INFORMATION FOR SEQ ID NO:15:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ATCTCGAGAT  GAACCGGGGA  GTCCCTTTTA  GGCACTTGCT                     40

T                                                                  41
```

( 2 ) INFORMATION FOR SEQ ID NO:16:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
AGCCTCCTAC  TATCATTATG  AATAACATTG  GCTGCACCGG                     40

GGTGGACCAT                                                         50
```

( 2 ) INFORMATION FOR SEQ ID NO:17:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
ATGGTCCACC  CCGGTGCAGC  CAATGTTATT  CATAATGATA                     40

GTAGGAGGCT                                                         50
```

( 2 ) INFORMATION FOR SEQ ID NO:18:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
ATCGCGCGCA  TCTTATAGCA  AAATCCTTTC  CAAGCCCTGT                     40

CTTA                                                               44
```

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear (x i) SEQUENCE DESCRIPTION: SEQ ID NO:19:

ATAGTCTAGA TGGAAGGGCT AATTTGG 27

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:20:

TTCTTGATGA TCAGGGGGAA GTTTCCTTGG 30

(2) INFORMATION FOR SEQ ID NO:21:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (x i) SEQUENCE DESCRIPTION: SEQ ID NO:21:

CTAAAAGGGA CTCCCCGGTT CATCTCTCTC CTTCTAGCCT 40

CC 42

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (x i) SEQUENCE DESCRIPTION: SEQ ID NO:22:

AAAACGGGTT ACCCAGGACC CTAAGCTCCA 30

(2) INFORMATION FOR SEQ ID NO:23:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (x i) SEQUENCE DESCRIPTION: SEQ ID NO:23:

CGCTGATCAA ACCGCGGTTG GGCCCTGCTA GAGATTTTCC 40

ACTGACTA 48

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (x i) SEQUENCE DESCRIPTION: SEQ ID NO:24:

CAGGCCATCC AATCACACTA 20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single (D) TOPOLOGY: linear (xi) SEQUENCE DESCRIPTION: SEQ ID NO:25:

GGTCAGTGGA TATCTGACCC 20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:26:

AGATCCATTC GATTAGTGAA 20

(2) INFORMATION FOR SEQ ID NO:27:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:27:

CTGATGAGTC CGTGAGGACG AAACTGTGCT GCGGCCGCTA 40

TAAGGTGGCA AGTGGTCAAA A 61

(2) INFORMATION FOR SEQ ID NO:28:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:28:

CGTCCTCACG GACTCATCAG CAATGTACCA TATGCTTATA 40

GCAAAATCCT TT 52

(2) INFORMATION FOR SEQ ID NO:29:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:29:

GAGCTAGCGG CCGCAGGAGC TTTGTTCCTT GGGTT 35

(2) INFORMATION FOR SEQ ID NO:30:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:30:

TCTGAAGCGG CCGCAGGAGC TGTTGATCCT TTAGG 35

(2) INFORMATION FOR SEQ ID NO:31:

(i) SEQUENCE CHARACTERISTICS:
        (A) LENGTH: 30 base pairs ( B ) TYPE: nucleic acid
( C ) STRANDEDNESS: single
( D ) TOPOLOGY: linear ( x i ) SEQUENCE DESCRIPTION: SEQ ID NO:31:

GATCCTCGAG CCATAATACT GATGAGTCCG    30

( 2 ) INFORMATION FOR SEQ ID NO:32:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:32:

GATCGGTACC GTAGCAATGT TTCGTCCTCA    30

( 2 ) INFORMATION FOR SEQ ID NO:33:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:33:

CTGAAGCGCG CACGGCAAGA    20

( 2 ) INFORMATION FOR SEQ ID NO:34:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO:34:

TATCTAATTC TCCCCCGCTT AATACGACG CTCTCGCACC    40

CAACTCTCTC    50

( 2 ) INFORMATION FOR SEQ ID NO:35:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO:35:

TCGCCGGTTC ATCTCCTATT ACCGAATTTT TTCCCATTTA    40

TCTAATTCTC    50

( 2 ) INFORMATION FOR SEQ ID NO:36:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( x i ) SEQUENCE DESCRIPTION: SEQ ID NO:36:

GAGAATTAGA TAAATGGGAA AAAATTCGGT AATAGGAGAT    40

GAACCGGGGA    50

( 2 ) INFORMATION FOR SEQ ID NO:37:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

GGTGCCACTA TCCTGGAGCT CCA                                                         23

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

ACAGCCTTCT CATGTCTCTA                                                             20

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

TAGAGACATG AGAAGGCTGT                                                           20

( 2 ) INFORMATION FOR SEQ ID NO:40:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

GCTCTCCTAT ATCTAATCTA AGGC                                               24

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

TGGCCTAATG TACCATTTGC                                                             20

( 2 ) INFORMATION FOR SEQ ID NO:42:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

GCCTTAGATT AGATAGAGGA GAGC                                               24

( 2 ) INFORMATION FOR SEQ ID NO:43:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:43:

GCATGGCTGC TTAATGTCCC 20

( 2 ) INFORMATION FOR SEQ ID NO:44:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:44:

GCAAATGGTA CATTAGGCCA 20

( 2 ) INFORMATION FOR SEQ ID NO:45:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:45:

ACTCCCCGGT TCATCTCCTA TTATTCTGCA GCTTCCTCAT 40

T 41

( 2 ) INFORMATION FOR SEQ ID NO:46:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:46:

GGGACATTAA GCAGCCATGC 20

( 2 ) INFORMATION FOR SEQ ID NO:47:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:47:

AATGAGGAAG CTGCAGAATA ATAGGAGATG AACCGGGGAG 40

T 41

( 2 ) INFORMATION FOR SEQ ID NO:48:

( i ) SEQUENCE CHARACTERISTICS:
  ( A ) LENGTH: 62 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:48:

GAAGCGCGCA CGGCAAGAGG CGAGGGGCGG CGACTGGTGA 40

GAGATGGGTG CGAGAGCGTC GG 62

( 2 ) INFORMATION FOR SEQ ID NO:49:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:49:

GGCCCTGCAT GCACTGGATG                            20

( 2 ) INFORMATION FOR SEQ ID NO:50:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:50:

CATAATAAGA ATTCTGCAAC                            20

( 2 ) INFORMATION FOR SEQ ID NO:51:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:51:

CAAGTTAACA GCACTATTC                            19

( 2 ) INFORMATION FOR SEQ ID NO:52:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:52:

GGGATATTGA TGATCTGTAG AATAGGAGCT TTGTTCCTTG GG           42

( 2 ) INFORMATION FOR SEQ ID NO:53:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:53:

CCCAAGGAAC AAAGCTCCTA TTCTACAGAT CATCAATATC             40

CC                                             42

( 2 ) INFORMATION FOR SEQ ID NO:54:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:54:

TAGTTAACAT AAGATACATT GATGAGT                       27

( 2 ) INFORMATION FOR SEQ ID NO:55:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

TAGCTAGCAT CATAATCAGC CATACCAC                                            28

( 2 ) INFORMATION FOR SEQ ID NO:56:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

GCGAATTCTG TAATACGACT CACTATAGGT CTCTCTGGTT                               40

AGACCAGATC TGAG                                                           54

( 2 ) INFORMATION FOR SEQ ID NO:57:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

CGCTGCAGAT GCATTTTTTT TTTTTTTTG AAGCACTCAA                                40

GGCAAGCTTT ATTG                                                           54

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

TTGAGCAAGT TAACAGCACT                                                     20

( 2 ) INFORMATION FOR SEQ ID NO:59:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:59:

AGATCCATTC GATTAGTGAA                                                     20

( 2 ) INFORMATION FOR SEQ ID NO:60:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:60:

TTCTCGAGGC GGCCGCGTCA CAGTTTCGTC CTCACGGACT 40

CATCAG 46

( 2 ) INFORMATION FOR SEQ ID NO:61:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:61:

TTAAGCTTCA TATGCCATAA TACTGATGAG TCCGTGAGGA 40

CG 42

( 2 ) INFORMATION FOR SEQ ID NO:62:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:62:

TTTCTCGAGG CGGCCGCAGC ACAGTTTCGT CCTCACGGAC 40

TCATCAG 47

( 2 ) INFORMATION FOR SEQ ID NO:63:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:63:

TTAAGCTTCA TATGGTACAT TGCTGATGAG TCCGTGAGGA 40

CG 42

( 2 ) INFORMATION FOR SEQ ID NO:64:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

TTATGCATCC CGGGATCCCA TACTGATGAG TCCGTGAGGA 40

CGAAACTGAT TAAATCGCAA CTGATGAGTC CG 72

( 2 ) INFORMATION FOR SEQ ID NO:65:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

CGGGACTCAT CAGCACATGG ACGGCTGGTT TCGTCCTCAC 40

GGACTCATCA GTTGCGATT 59

( 2 ) INFORMATION FOR SEQ ID NO:66:

( i ) SEQUENCE CHARACTERISTICS:
            ( A ) LENGTH: 58 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:66:

```
TCCATGTGCT GATGAGTCCG TGAGGACGAA ACATTGTAGA                40

GGGGCACTGA TGAGTCCG                                        58
```

( 2 ) INFORMATION FOR SEQ ID NO:67:

( i ) SEQUENCE CHARACTERISTICS:
            ( A ) LENGTH: 52 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:67:

```
TTACGCGTAC TAGTAGCAAT GTTTCGTCCT CACGGACTCA                40

TCAGTGCCCC TC                                              52
```

( 2 ) INFORMATION FOR SEQ ID NO:68:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:68:

```
GATCCTCGAG ATCCCGGGAT CCCATACTGA                           30
```

( 2 ) INFORMATION FOR SEQ ID NO:69:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:69:

```
GATCGAATTC GCGTACTAGT AGCAATGTTT CG                        32
```

( 2 ) INFORMATION FOR SEQ ID NO:70:

( i ) SEQUENCE CHARACTERISTICS:
            ( A ) LENGTH: 65 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:70:

```
GATCGTCCGA CGTTAATTTC TGATGAGTCC GTGAGGACGA                40

AACACATGGT GCCATTTCTG ATGAG                                65
```

( 2 ) INFORMATION FOR SEQ ID NO:71:

( i ) SEQUENCE CHARACTERISTICS:
            ( A ) LENGTH: 54 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:71:

CTCATCAGCA AGACCCACTG CTGTTTCGTC CTCACGGACT 40

CATCAGAAAT GGCA 54

( 2 ) INFORMATION FOR SEQ ID NO:72:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:72:

GGGTCTTGCT GATGAGTCCG TGAGGACGAA ACAATTAATT 40

TTGCTCCTGA TGAG 54

( 2 ) INFORMATION FOR SEQ ID NO:73:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:73:

GATCGGATCC ACATTAGTTT CGTCCTCACG GACTCATCAG 40

GAGCAAAA 48

( 2 ) INFORMATION FOR SEQ ID NO:74:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:74:

GATCGGATCC ACATTAGTTT CG 22

( 2 ) INFORMATION FOR SEQ ID NO:75:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:75:

GATCGTCGAC GTTAATTTCT GA 22

( 2 ) INFORMATION FOR SEQ ID NO:76:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:76:

CUGAUGAGUC CGUGAGGACG AAAC 24

( 2 ) INFORMATION FOR SEQ ID NO:77:

( i ) SEQUENCE CHARACTERISTICS:
    ( A ) LENGTH: 234 base pairs (B) TYPE: nucleic acid
(C) STRANDEDNESS: single
(D) TOPOLOGY: linear (xi) SEQUENCE DESCRIPTION: SEQ ID NO:77:

| | | | | |
|---|---|---|---|---|
| UCCUCGACAA | CUAGGAAAUC | CAUAGAAAGG | UGUCGGUCCU | 40 |
| AAGAACGGAC | CUCGACGAAC | UACGGGGUCU | GACACUCAAC | 80 |
| GUUGUCUACG | ACAACGCGGA | GUUAUCGGGA | GUCGUUUAAC | 120 |
| AAGACGACGA | CGUGAUAUGG | UCUGUUAUUA | ACAGACCGGA | 160 |
| CAUGGCAGUC | GCAGUAACUG | CGACGCGGGU | AUCACGAAGG | 200 |
| ACGACGAGGG | UUCUUGGGUU | CCUUGUUUCG | AGGA | 234 |

DNA CONSTRUCTS ENCODING CD4 FUSION PROTEINS

This is a continuation of application Ser. No. 07/936,849, filed on Aug. 28, 1992 now abandoned which is a continuation-in-part of Ser. No. 07/751,830 filed Aug. 30, 1991, abandoned.

BACKGROUND OF THE INVENTION

1. Technical Field

The subject invention relates to defective, interfering HIV particles and uses thereof. In particular, these particles encode a membrane bound receptor protein which interferes with the production of infectious HIV by a host cell by downregulating the amount of HIV envelope protein on the surface of the cell.

One facet of the subject invention relates to multitarget-ribozymes which may cleave up to nine HIV-env RNA regions thereby preventing HIV replication.

2. Background Information

As of today, no therapy is available which completely prevents the onset of AIDS in HIV infected patients. Currently, the most commonly used drug, which is approved by the FDA and which interferes with HIV replication, is AZT (Mitsuya, H., et al., Proc. Natl. Acad. Sci. USA 82:7096–7100 (1985), Fischl, M. A., et al., N. Engl. J. Med. 317:185–191 (1987)). AZT appears to inhibit the viral reverse transcriptase and thereby delays, but does not prevent the onset of AIDS. Unfortunately, in the presence of AZT, there is a continuous natural selection of AZT resistant mutants of HIV which are generated at a low level of HIV replication in a subset of infected cells (Larder, B. A., et al., Science 243:1731–1734 (1989)).

The potential use of transdominant mutants of the HIV gag (Trono, D.,et al., Cell 59, 113–120 (1989)), tat (Green M., et al., Cell 58:215–223 (1989)) and rev (Malim, M. H., et al., Cell 58:205–214 (1989)) genes has been proposed as a means of "intracellular immunization" (Baltimore, D., et al., Nature 335:395–396 (1988)). This is a form of gene therapy which initially involves the protection of precursor cells of the T4 helper cell lineage from the killing by HIV. It has been proposed that defective proviruses could, for example, express a soluble CD4 retained in the endoplasmic reticulum (Buonocore, L., et al., Nature 345:625–628 (1990)), an antisense RNA (Sczakiel, G., et al., J. Virol. 65:468–472 (1991); Han, L., et al., Proc. Natl. Acad. Sci. USA 88:4313–4317 (1991)) or ribozymes (Sarver, N., et al., Science 247:1222–1225 (1990)) directed against HIV RNAs etc. In all of these approaches, stem cells have to be isolated from each patient. The interfering gene has to be specifically inserted into the genome of these cells. The altered cells are subsequently reintroduced into the patient. In the patient, it is anticipated that progeny of these stem cells will then stay resistant to HIV. A rapid depletion of the T4 helper cells, like during the late phase of an HIV infection, may thereby be avoided for some time.

The addition of various inhibitors to HIV replication has not yielded the anticipated protection as yet without the elimination of accompanying toxicity. The in vitro targeting and specific cell killing of HIV infected cells by chimeric CD4-toxin proteins has been described (Berger, E. A., et al., Proc. Natl. Acad. Sci. USA 86:9539–9543 (1989); Chaudhary, V. K., et al., Nature 355:369–372 (1988); M. A. Till, et al., Science 242:1166–1168 (1988)). This approach is impressively effective in tissue culture, however, the stability of the protein as well as the amounts which are needed to assure constant protection seem to make this approach not only very costly, but reaching the target cells may be difficult. This is also the case with synthetic peptides or antisense oligonucleotides (Matsukura, N., et al., Proc. Nat. Acad. Sci. USA 86:4244–4248 (1989)) which may have inhibitory activity in tissue culture, but because of their usual very short half life or inefficient cellular uptake, often can only give a temporary protection. In addition, some peptides may potentially trigger an undesired immune response.

The use of drugs and other specific compounds, which inhibit various stages of HIV replication from viral adsorption to the cell, viral entry, uncoating, reverse transcription, integration, protease activity, myristoylation of gag, viral assembly and the packaging of the genome etc., is limited (Deen, K. C., et al., Nature 331:82–84 (1988); Traunecker, A., et al., Nature 339:68–70 (1989); Capon, D. J., et al., Nature 337:525–531 (1989); Mitsuya, H., et al., Science 240:646–649 (1988); Pal, R., et al., AIDS Res. Hum. Retrov. 6:721–730 (1990); Hirsch, M. S., et al., "Antiviral Agents" in Virology (B. N. Fields, and D. M. Knipe, eds.) Raven Press, New York, N.Y., pp. 441–468 (1990)). The compounds have to be kept continuously at often high concentrations to be active with potential high levels of toxicity. At the same time, it can be expected that resistant virus is slowly generated and selected. The intracellular immunization gene therapy (Baltimore, D., et al., Nature 335:395–396 (1988)) on the other hand, only protects a small fraction of the stem cells, but also most progeny, which are derived from the resistant stem cell. Unfortunately, not all stem cells can be made resistant. The procedure is laborious and the resistant fraction may be too small or insufficient to prevent the depletion of the T4 helper cells over a longer period of time.

The present invention differs from the above therapies in many ways. For example, the invention differs decisively from the gene therapy approach because it involves a mobile element, namely a specifically targeted, defective interfering HIV particle, which will be continuously replicated only in HIV infected cells. This would allow, for the first time, spread of the interfering genes encoded in the defective HIV genome, throughout the various populations of HIV expressing cells, and also to CD4+ cells which are not infected by HIV.

All U.S. patents and publications referred to herein are hereby incorporated by reference.

SUMMARY OF THE INVENTION

The present invention relates to multiple generations of DNA constructs which represent novel defective interfering HIV proviral genomes and to uses thereof. The initial parental DNA construct as well as the individual DNA additions in the other prototypes have been completely sequenced. They all encode a functional chimeric HIV receptor protein (CD4/env). High levels of expression of this membrane bound receptor interferes with the production of infectious HIV by down regulating the amount of HIV envelope protein on the cell surface. Some DNA constructs encode, in addition, a regulatory element (RRE) and/or different ribozymes, which selectively cleave HIV RNA transcripts at one or at multiple sites within the HIV env coding region in vivo.

The invention also describes the necessary DNA additions for the packaging of these defective genomic RNAs into the first defective interfering HIV particles. The potential therapeutical use of these HIV particles against AIDS is indicated. Towards this goal, these defective interfering particles are specifically designed to initially target HIV envelope protein (env) expressing cells. This may be achieved by inserting the chimeric HIV receptor itself (CD4/env) into the envelope of the defective interfering HIV particle, which will be possible after down regulating the amount of env protein in the plasma membrane through the expression of CD4/env. In addition, having low concentrations of the HIV env protein in their envelope, these particles will also be able to spread the interfering gene(s) to uninfected CD4+ cells.

In particular, the present invention includes a viral particle which interferes with the replication of a retrovirus present in a host cell wherein the genome of the viral particle comprises a gene operably linked to at least one LTR promoter sequence of the retrovirus, wherein the gene comprises a nucleic acid sequence which encodes the ectodomain portion of a membrane bound protein of the host cell, and wherein the membrane bound protein binds to the envelope protein of the retrovirus and serves as the receptor of the virus.

The genome of the viral particle may also contain at least one ribozyme, or a multitarget ribozyme, wherein the ribozyme selectively cleaves the nucleic acid sequence of the retrovirus without cleaving the nucleic acid sequence of the particle or of the host cell. The at least one ribozyme may be a multiribozyme containing from 2 to 20 different ribozymes. The retrovirus may be HIV, and the membrane bound protein may be CD4.

The gene noted above may further comprise the transmembrane and cytoplasmic portions of the HIV envelope protein gene, such that the gene encodes a chimeric protein comprising the ectodomain of CD4 and the transmembrane and cytoplasmic portions of the HIV envelope protein.

The RNA genome of the viral particle may be transcribed from, for example, the DNA sequence shown in FIG. 24 or FIG. 25.

The present invention also encompasses a host cell stably transformed with the genome of the viral particle.

Furthermore, the present invention also includes a recombinant DNA molecule, which when transcribed into genomic viral RNA, can be packaged into a viral particle and interferes with the replication of a retrovirus present in a host cell, comprising:

(i) a DNA segment which encodes a chimeric protein which interferes with the replication of a retrovirus in a host cell infected with the retrovirus; and (ii) a vector for introducing the DNA segment into said infected host cell. The sequence of the DNA segment may be any one of the sequences shown in FIGS. 19, and 21–25, or portions or allelic variations thereof. The vector may be, for example, a plasmid such as pGem4XB. The chimeric protein referred to above may be CD4/env.

Furthermore, the invention also includes a DNA construct selected from the group consisting of: HD1, HD2, HD3, HD4, HD5 and HD6. The DNA sequence of each construct is shown in FIGS. 19, 21, 22, 23, 24, and 25, respectively.

The present invention also encompasses a DNA construct selected from the group consisting of: DIRz27, HDPACK1, MONORz37, MONORz6, NONARz63-6, PENTARz51, and PENTARz63. The nucleotide sequence of each construct is shown in FIGS. 18, 26, 27, 28, 29, 30 and 31, respectively.

In addition, the invention includes a method of preparing a viral particle which interferes with the replication of a retrovirus in a host cell infected with the retrovirus comprising the steps of:

a) transfecting helper provirus DNA into CD4 positive cells;

b) selecting transfected cells which express the helper provirus DNA by cotransfecting low amounts of a drug resistant marker gene, such as the neomycin resistance gene, together with the helper provirus DNA; and c) transfecting the selected cells of step (b) with the recombinant molecule referred to above under conditions such that said resulting transfected cells produce said viral particle. The invention also includes the viral particle produced by this method.

An alternative method is also included which allows for the production of viral particles by co-transfections of helper provirus DNA with the recombinant molecule.

Furthermore, the invention also includes a pharmaceutical composition comprising the viral particle and a pharmaceutically acceptable carrier.

Also, the invention encompasses a method of treating a patient infected with a human immunodeficiency virus comprising administering to the patient an amount of the above-composition sufficient to effect said treatment.

The invention also includes a host cell which produces the viral particle.

Additionally, the present invention encompasses a method of preventing HIV-infected cells in a patient from producing infectious HIV comprising the steps of:

a) removing stem cells from the patient;

b) transfecting the stem cells with the recombinant molecule; and c) reintroducing the transfected cells into the patient such that when infected with HIV, said transfected cells produce low amounts of less or non-infectious HIV. In this manner, the spread of the virus is hindered.

Figure 1:
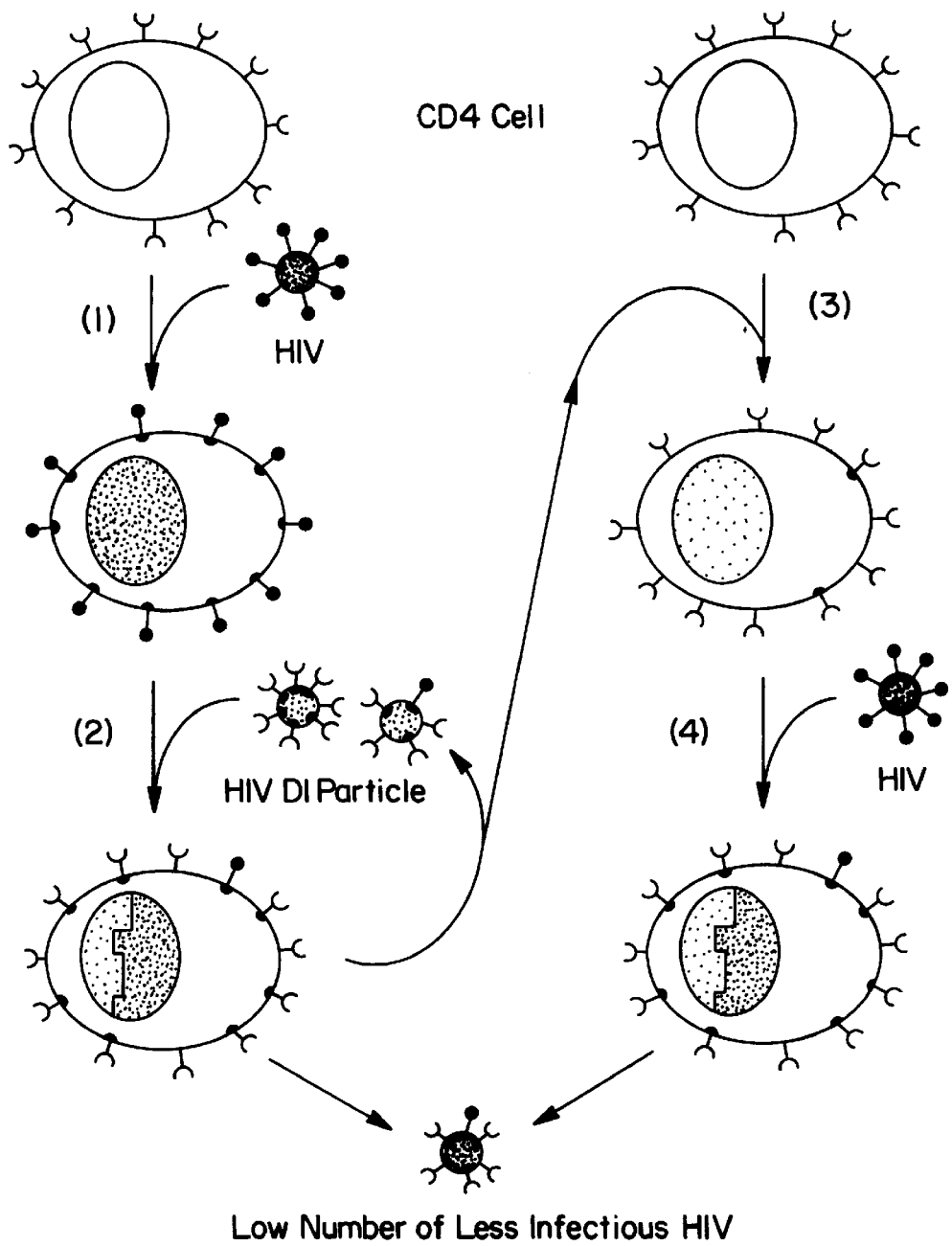
FIG. 1 represents the antiviral strategy against AIDS using the targeted defective interfering HIV particles.

(1) During infection of CD4+ cells with HIV, the HIV envelope protein (env) at the surface of the virus particle specifically binds to its receptor, the CD4 protein (Maddon, P. J., et al., Cell 47:333–348 (1986)) present at the surface of cells, like T4 helper cells, macrophages, etc. The env protein contains a fusion domain, which carries out the fusion of the viral envelope membrane with the cellular plasma membrane. This allows entry of the viral core into the cell, where it is subsequently uncoated. Packaged reverse transcriptase synthesizes a DNA copy of the viral genomic RNA, which is made double stranded and integrated into the host genome by the viral integrase protein packaged in the virion. Upon activation of the cell, the HIV proviral genome is transcribed and the regulatory (like tat, rev) and structural proteins (like gag, pol and env) are translated. The expression of the env protein causes a downregulation of the receptor, the CD4 protein, on the cell surface, and the cell exhibits the HIV env on its surface instead. This results in a viral exclusion which prevents other HIV particles from superinfecting the same cell. In the late stage of the infection, HIV particles are released from this cell, which can again infect other CD4+ cells.

(2) The genomes of the targeted defective interfering HIV particles of the present invention encode a chimeric CD4/env protein, which is placed under control of the HIV LTR promoter. In addition, the genome of the particle may contain a multitargeted ribozyme which specifically cleaves the HIV genome and the env mRNA within the gp 120 region. The defective interfering particle is replication defective, and it needs all essential structural and regulatory proteins provided in trans by the wildtype helper virus. The defective interfering particle carries a functional HIV receptor in its envelope, comprising the ectodomain portion of the CD4 protein, and is able to bind and specifically infect HIV infected cells which express the env protein on their surface, and to which the CD4 protein binds. This unique feature of the defective particle allows it to circumvent the viral exclusion of homologous virus, normally caused by the endogenous virus.

After adsorption and entry into these cells, the defective genome is uncoated, reverse transcribed and integrated into the host chromosome like HIV itself. The HIV virus previously infecting the cell now acts as a "helper" virus. The transactivator protein tat, provided by the HIV helper virus, transactivates the expression of the defective genome. The rev responsive element RRE (Malim, M. H., et al., Nature 338:254–256 (1989)) in its genomic RNA makes the defective particle RNA responsive to the presence of the rev protein, again provided by the helper virus (for review Chen, I. S. Y., Cell 47:1–2 (1986); Haseltine, W. A., J. Acquuir. Imm. Defic. Syndr. 1:217–240 (1988); Cullen, B. R., et al., Virol. 178:1–5 (1990)). After transcription of the defective provirus and translation of the encoded CD4/env protein, CD4/env interacts with the HIV env protein in the endoplasmic reticulum and arrests its transport to the plasma membrane (Buonocore, L., et al., Nature 345:625–628 (1990); Crise, B., et al., Virol. 64:5585–5593 (1990); Kawamura, I., et al., J. Virol. 63:3748–3754 (1989)). Overexpression of CD4/env causes a downregulation of the surface expression of env. This interaction of the CD4 ectodomain with the HIV env is probably one of the most specific interactions of the virus with a cellular component. The dissociation constant is in the order of $10^{-9}$. The infected cell now expresses the chimeric CD4 on its surface instead of the env protein. Any virus which is released from these cells will have a different makeup. They may either lack the env protein altogether, replaced by the chimeric CD4/env protein, or they may contain a severely reduced number of env on their surface. Consequently, in either case, they are less infectious.

The genome of the defective interfering particle is transcribed in the presence of HIV. The defective RNA contains packaging sequences, which allows for the packaging of the defective genome during the assembly of new virus particles, using all the necessary proteins provided in trans by the helper virus. Since the defective RNA has ribozyme activity, it interacts and specifically cleaves the HIV genome and env mRNA. This will not only inactivate some of the HIV genome before packaging, but it will also decrease the amount of env protein in the cell. The assembly of the defective interfering particle is, therefore, favored by this antiviral approach at the expense of the helper virus. The defective interfering particle will be able to repeat the same cycle in other HIV env expressing cells.

(3) It can be anticipated that some of the defective HIV particles also contain low amounts of env protein which have escaped interference. These particles are able to infect CD4+ cells, which have not previously been infected by HIV. Again, the defective genome will use the packaged reverse transcriptase and integrase supplied by the HIV helper virus, to integrate into the host genome. Since, in this case, the regulatory proteins of HIV are absent, there is no transactivation of viral transcription and the expression of the defective genome will be low or even silent.

(4) Upon infection of this cell with HIV, however, transactivation of gene expression will occur, which leads to the same cycle of viral expression as in (2). The result will be identical with respect to the release to low numbers of infectious HIV particles, while the assembly of the defective interfering genome is favored. Alternatively, if there is low expression of the defective provirus in the absence of HIV, the possibility exists that the encoded ribozymes may already be able to inactivate the RNA genome of the incoming virus, as was suggested as a possibility in the presence of higher levels of constitutively expressed monoribozyme (Sarver, N., et al., Science 247:1222–1225 (1990)).

Figure 3:
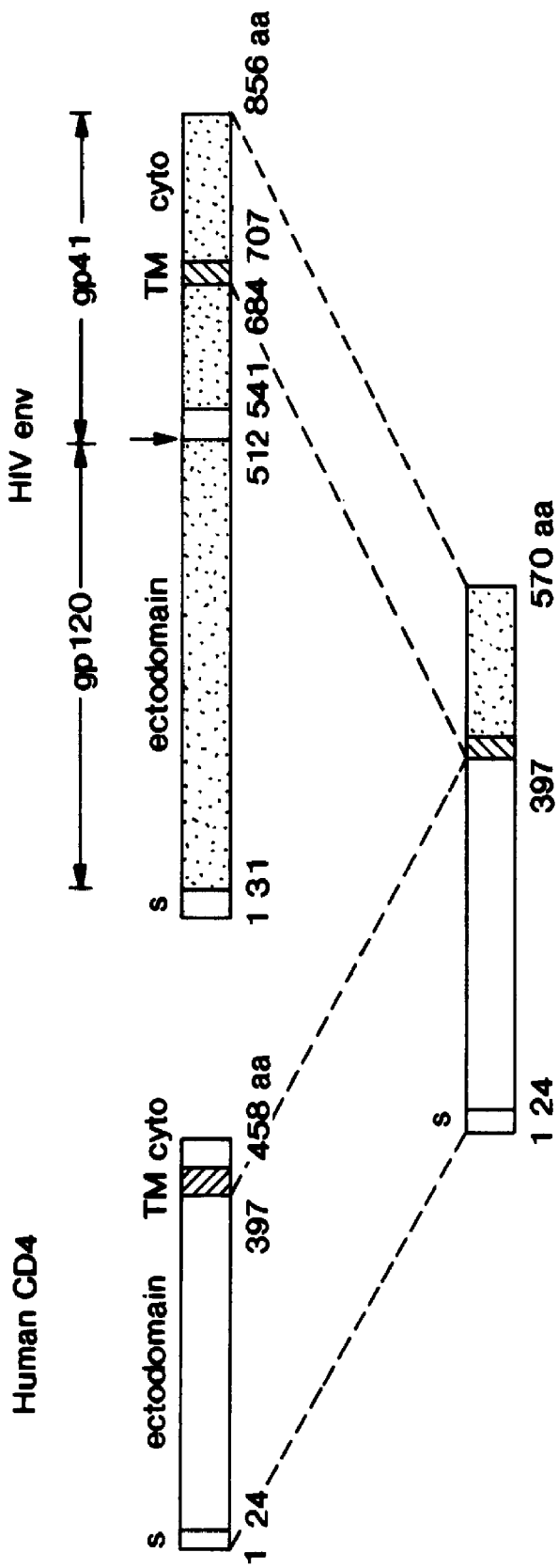

FIG. 2 shows the structure of the first prototype defective interfering HIV proviruses. Prototype HD1 contains a precise fusion of the ectodomain region of the human CD4 into the HIV genome by replacing the entire HIV region, starting with the first AUG of gag, which is replaced by the AUG of CD4, and ending after the last amino acid of the ectodomain of the HIV envelope protein region (FIG. 3). This construct leaves the transmembrane and cytoplasmic domains of the env region intact. It also retains the entire nef region and both 5' and 3' LTRs while all other genes are removed. Transcripts made from this DNA encode both the chimeric CD4/env protein as well as the nef protein (see FIG. 7). The complete sequence of this construct (HD1) has been determined. Prototype HD2 is identical to prototype HD1, but it has a short single target ribozyme inserted at the position as indicated. This ribozyme is directed against a specific site in the gp 120 ectodomain region of the HIV env mRNA (position 728 in FIG. 13). The third prototype (HD3) has, in addition, a 240 nucleotide long rev responsive element inserted. In the prototype HD4 DNA, a 118 bp portion of the nef region is replaced by a novel multitarget-ribozyme (nonaribozyme 63–6) which cleaves HIV env mRNA at the nine different sites as shown in FIG. 15. The functional pentaribozyme shown in FIG. 14 is part of this nonaribozyme. HD5 and HD6 have different size packaging signals inserted (approximately 63 bp and 639 bp, respectively), which are derived from the beginning of the HIV gag gene. Both the elimination of the AUG translation start and the introduction of stop codons at various sites with the larger 639 gag fragment will prevent translation of this region even after potential recombinational events with other, naturally occurring defective HIV genomes.

FIG. 3 represents the precise fusion of the CD4 and HIV env DNA clones for the encoding of a functional chimeric CD4/env receptor. The chimeric gene was generated by a rapid gene fusion reaction using specific fusion oligonucleotides and polymerase chain reaction (Schubert, M., et al., J. Virol. (66:1579–89 (1992) (66:1579–89 (1991); Yon, J., et al., Nucl. Acids. Res. 17:4895 (1989)). The sequence was determined after insertion into the prototype HD1 construct shown in FIG. 2. The protein has been expressed in vitro and in vivo, and its functionality as a receptor was demonstrated in a syncytia forming assay when coexpressed with the HIV envelope protein.

Figure 4:
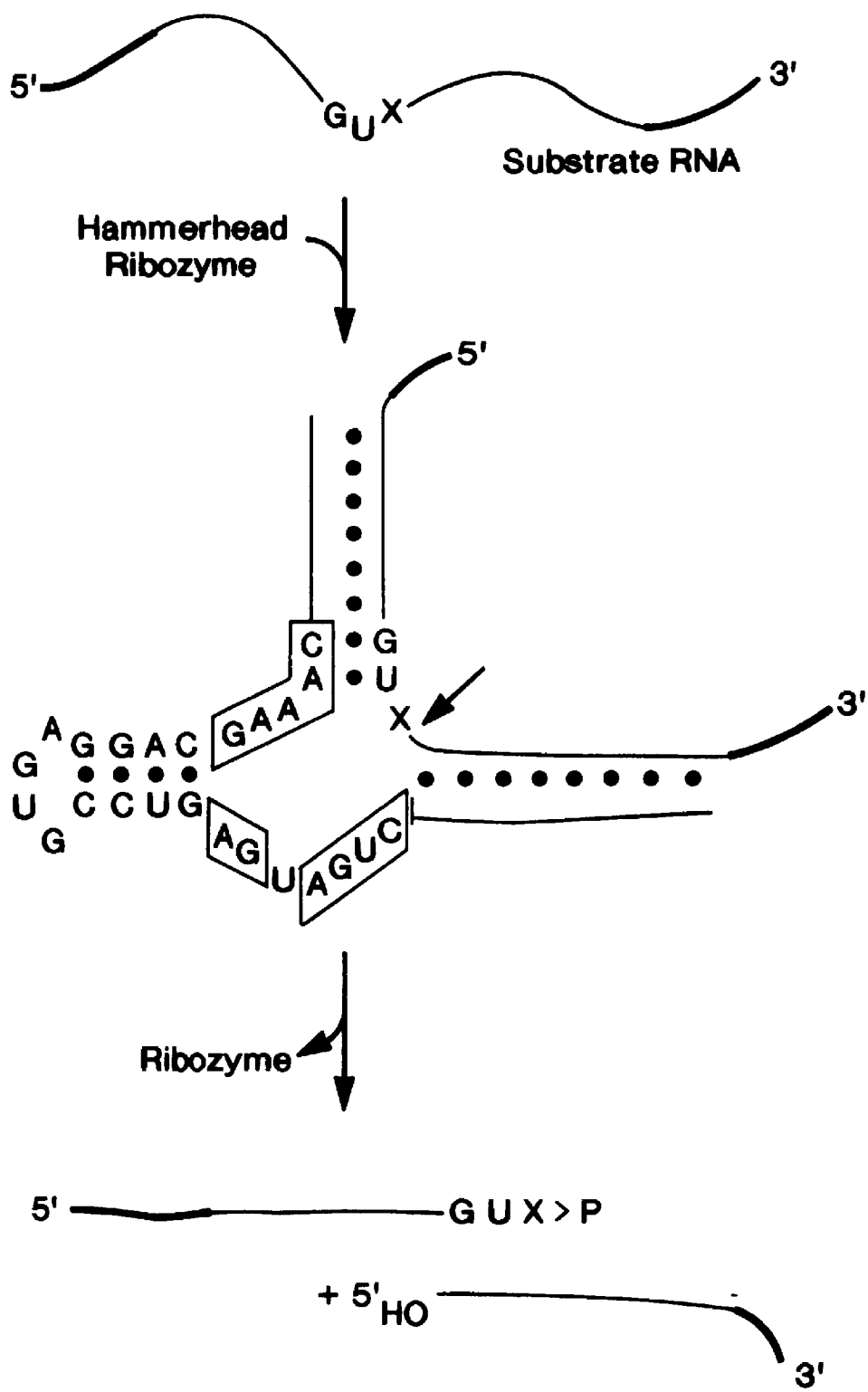

FIG. 4 shows the structure of a hammerhead type (SEQ ID NO: 76) ribozyme according to Haseloff and Gerlach (Haseloff, J., et al., Nature 334:585–591 (1988)). The substrate RNA and the ribozyme RNA are shown after annealing. The ribozyme cleaves the target RNA after the GUX triplet. Specific targeting is achieved by the flanking sequences which are complementary to the ribozyme sequences as indicated. Multitarget-ribozymes, like the pentaribozymes shown in FIG. 14, are repeats of this general structure which are covalently linked, with each ribozyme unit within that structure having different flanking sequences directed at the individual selected target sites.

Figure 5:
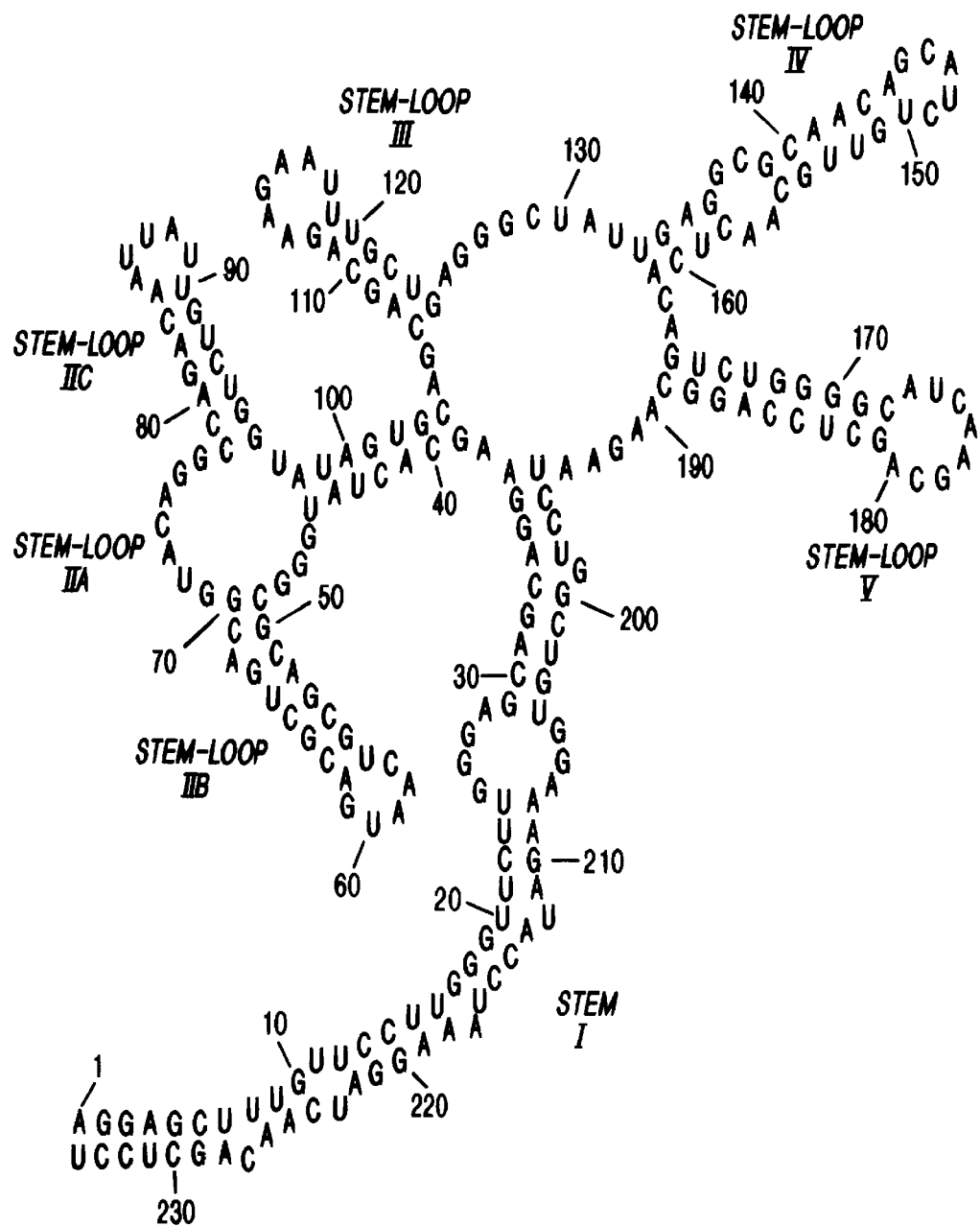

FIG. 5 shows the nucleotide sequence of a rev responsive element (SEQ ID NO: 77) as described in Malim et al., Nature 338:254–56 (1989). The ref responsive element of the HIV-1 clone pNL4-3 (Adachi, Aikio, et al., J. Virol. 59:284–291 (1986)) was amplified by polymerase chain reaction and cloned into the Not 1 site of HD2. The element was sequenced and confirmed with one nucleotide missing at position 2788 in the HD3 sequence which should not affect the functionality of the element.

Figure 6:
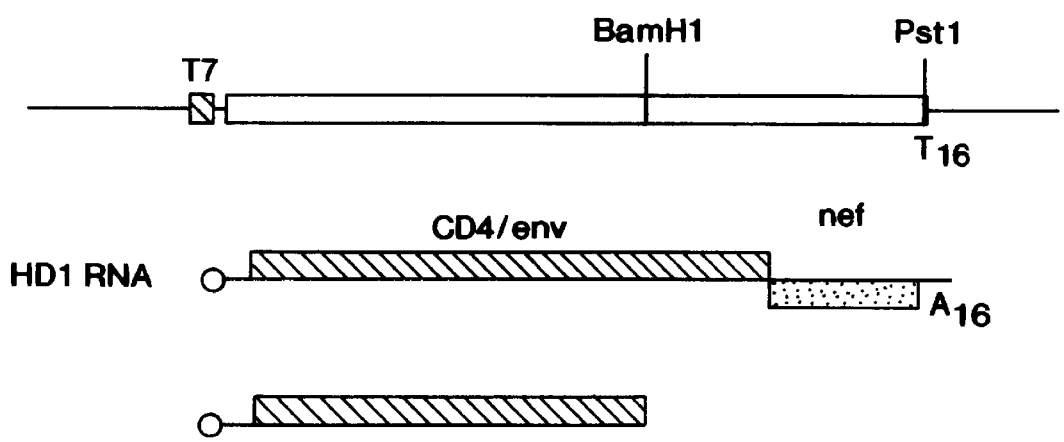

FIG. 6 shows the construction of a prototype HD1 defective interfering HIV particle DNA, HD1(T7) which can be expressed by T7 RNA polymerase in vitro and in vivo (Fuerst, T. R., et al., Proc. Natl. Acad. Sci. USA 83:8122–8126 (1986)). The promoter for T7 RNA polymerase was precisely fused to the HD1 DNA so that transcription of this DNA with T7 RNA polymerase results in a precise initiation of the transcript at a site within the HIV LTR which is also precisely used by the cellular RNA polymerase II. The larger poly A tail, which is normally found with mRNAs in vivo, is replaced by a shorter tail of 16 A residues by run-off transcription after cleavage with Pst1. By adding T7 RNA polymerase to this DNA in vitro, precise RNA transcripts are made which can be translated in vitro into the chimeric CD4/env and the nef proteins. The translation of run-off transcripts made after BamH1 cleavage results in a truncated CD4/env protein and an absence of nef protein. These data show that the mRNA functions as a bicistronic messenger RNA in vitro. Products of the transcription and translation are shown in FIG. 7.

Figures 7A, 7B, 7C:
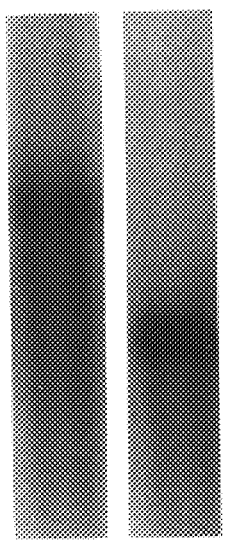

FIGS. 7A–7C represent in vitro transcription of HD1(T7) and translation of the mRNA. HD1(T7) DNA was transcribed in vitro using T7 RNA polymerase according to standard procedures (FIG. 7A, lane 1). A truncated version of the transcript was also synthesized after linearization of HD1(T7) DNA using BamH1 restriction endonuclease (FIG. 7A, lane 2). Both mRNAs were translated in an in vitro translation system using a reticulocyte lysate as shown in FIG. 7B, lanes 1 and 2, respectively. As can be seen, when the complete transcript, which is basically identical to the HD1 RNA genome, is translated, two major proteins corresponding to the chimeric CD4/env (63 KDa) and the nef protein (27KDa) are detected which have the expected sizes as compared to protein standard size markers (FIG. 7B, lane 1). The positions of the size markers which were not isotopically labelled are indicated, and their sizes are listed in kilodaltons. As expected, when the truncated RNA shown in lane 2, FIG. 7A was translated, a shorter CD4/env protein was detected which contains the amino terminal portion of the protein (FIG. 7B, lane 2). Nef is not encoded within this mRNA. The identity of these proteins was confirmed by immunoprecipitations of these proteins using antibodies directed against an ectodomain region of CD4 located in CD4/env (FIG. 7C, lane 2). Antibodies to nef in turn specifically immunoprecipitate the nef protein encoded in the complete bicistronic transcript (FIG. 7C, lane 1).

Figure 8A:
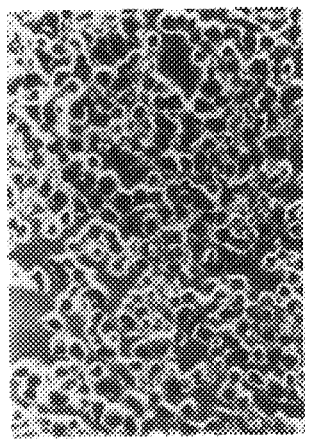
Figure 8B:
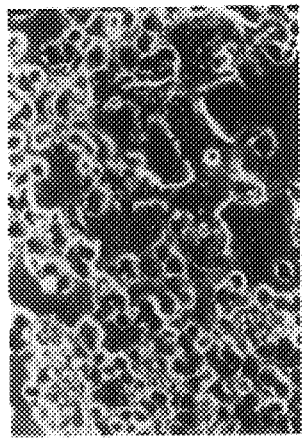
Figure 8C:
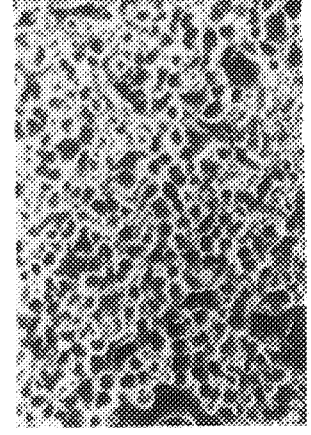
Figure 8D:
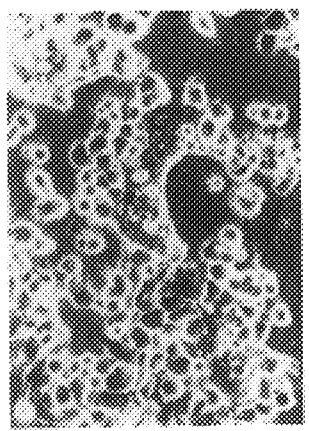
Figure 8E:
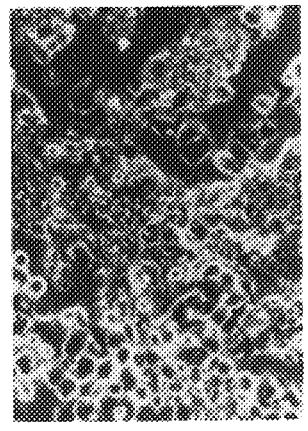
Figure 8F:
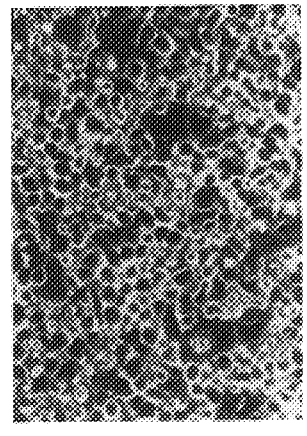

FIGS. 8A–8F show inhibition of syncytia formation by CD4/env using the vaccinia virus expression system. A cDNA clone which encodes the entire HIV envelope protein penv5 under control of the T7 RNA polymerase promoter (Earl, P. L., et al., J. Virol. 64:2448–2451 (1990)) was cotransfected with HD1(T7) DNA into Hela cells which constitutively express the CD4 protein. Transfections were carried out using the Lipofectin method. After transfection, all cells were infected with the vaccinia virus recombinant (Fuerst, T. R., Proc. Natl. Acad. Sci. USA 83:8122–8126 (1986)) expressing the T7 RNA polymerase. FIG. 8A shows the cytopathic effect caused by vaccinia virus alone in the absence of the two DNAs. In the presence of env expression (FIG. 8B) a characteristic fusion of the Hela T4 cells is observed which is as expected absent when only the HD1 (T7) DNA is transfected into the cells (FIG. 8C). During the cotransfections of HD1(T7) and penv5, different results were obtained depending on the amount of pHD1 (T7) DNA added and the amount of CD4/env protein encoded by the HD1(T7) transcripts (FIGS. 8D–8F). As can be seen, low amounts of HD1 (T7) DNA have no inhibitory effect on syncytia formation, however, a fourfold excess was able to dramatically inhibit the fusogenic activity of env, presumably by the formation of CD4/env protein/env protein complexes in the endoplasmic reticulum or the golgi apparatus. This result demonstrates that the CD4/env interferes with the transport and the functionality of env by neutralizing it in the cytoplasm. Small excess of the CD4/env DNA is able to tip the balance towards inhibition of fusion. As an additional control, cotransfection of penv5 with a 20 fold excess of an unrelated DNA, which also carries a T7 RNA polymerase promoter, did not result in a competition for limited amounts of T7 RNA polymerase and an inhibition of syncytia formation.

Figure 9:
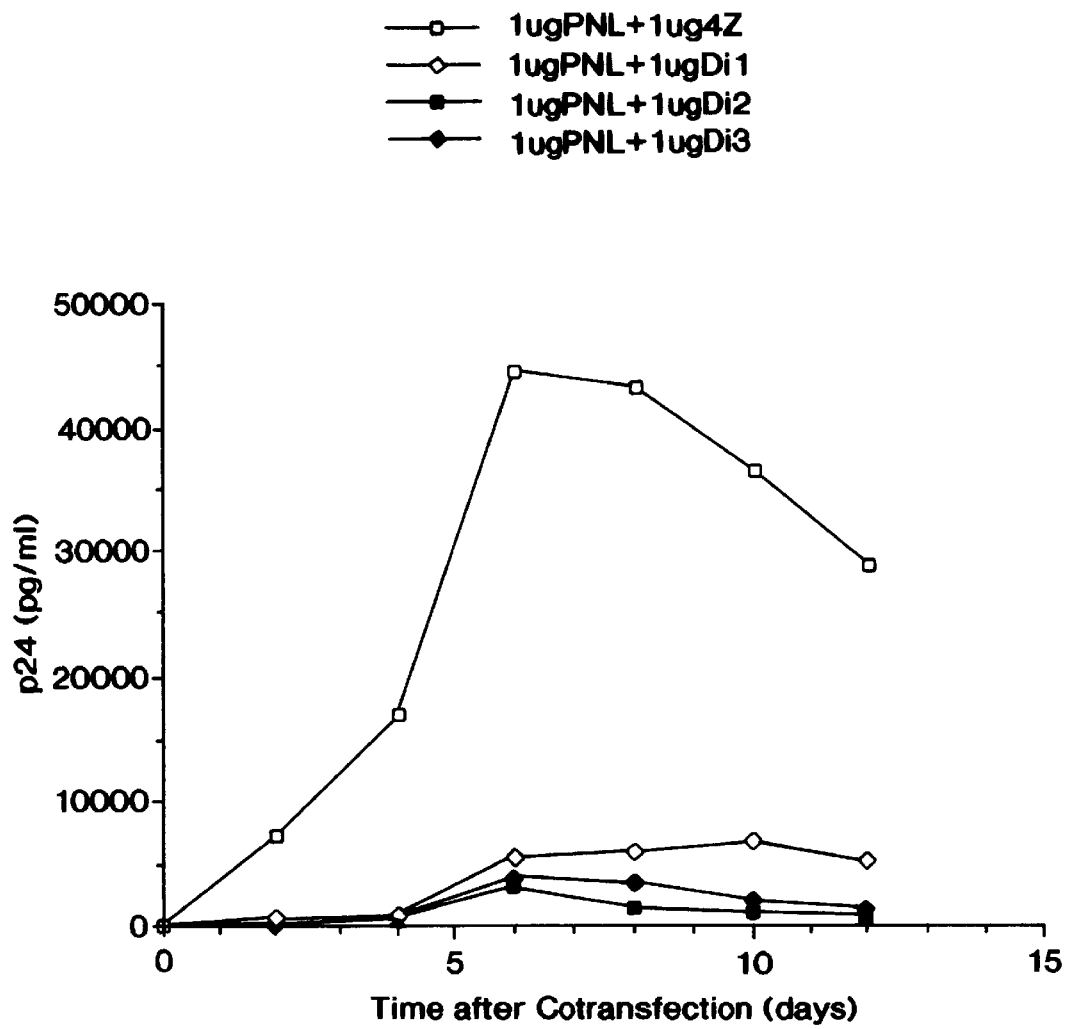

FIG. 9 represents interference of HD1, HD2 and HD3 with HIV replication. The infectious HIV-1 clone pNL4-3 (PNL) (Adachi et al., J. Virol. 59:284–91 (1986)) was cotransfected with the same amount of the three different defective HIV DNAs (Di1, Di2, Di3) and an unrelated control DNA (4Z) into Hela T4 cells. The amounts of p24 antigen in the supernatant of the transfected cells were determined at intervals using a capture-elisa assay.

Figure 10A:
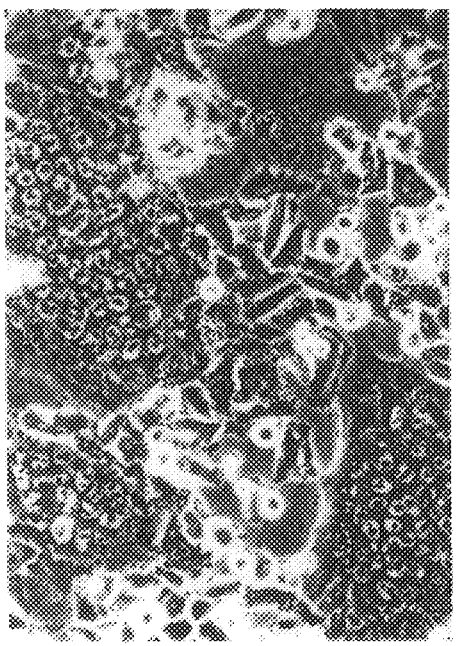
Figure 10B:
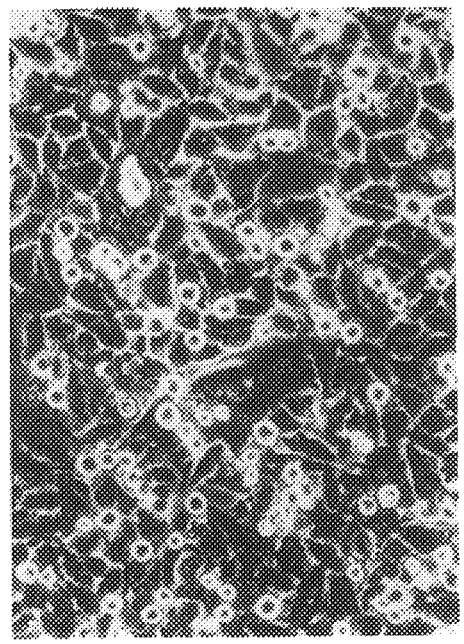

FIGS. 10A and 10B show the inhibition of syncytia formation caused by HIV-1 infections. Hela T4 cells were cotransfected with pNL4-3, which is a complete infectious clone of HIV, and with the same amount of an unrelated DNA. Five days after transfection the formation of syncytia was scored which were large and very frequent (panel A). In contrast, when the cells were cotransfected with either the HD1, HD2 or HD3 prototype DNAs, very few syncytia were observed (panel B, the result with HD3 is shown). This demonstrates that the expression of CD4/env from the HIV LTR promoter alone (like with HD1) is sufficient not only for the inhibition of syncytia formation but, as the low level of released p24 antigen demonstrates (see FIG. 9), it also inhibits the spread of the virus to neighboring Hela T4 cells, which are all permissive for HIV infections and which would support HIV production in the absence of the defective interfering HIV genome.

FIG. 11 shows deletion mutations in HD1 and HD3 which eliminate the amino terminal region of CD4/env and which restore high levels of p24 antigen release as well as syncytia formation in a cotransfection with the infectious HIV clone pNL4-3. Cotransfections of Hela T4 cells were carried out as described above with respect to FIGS. 9 and 10. The deletion mutants of HD1 and HD3, which had precisely 527 bp deleted including the AUG start codon of CD4/env, did not prevent virus spread as measured by p24 release and the presence of syncytia after 5 days in culture. This confirms that the main factor for the efficient inhibition of HIV replication and virus spread was the CD4/env protein.

Figure 12:
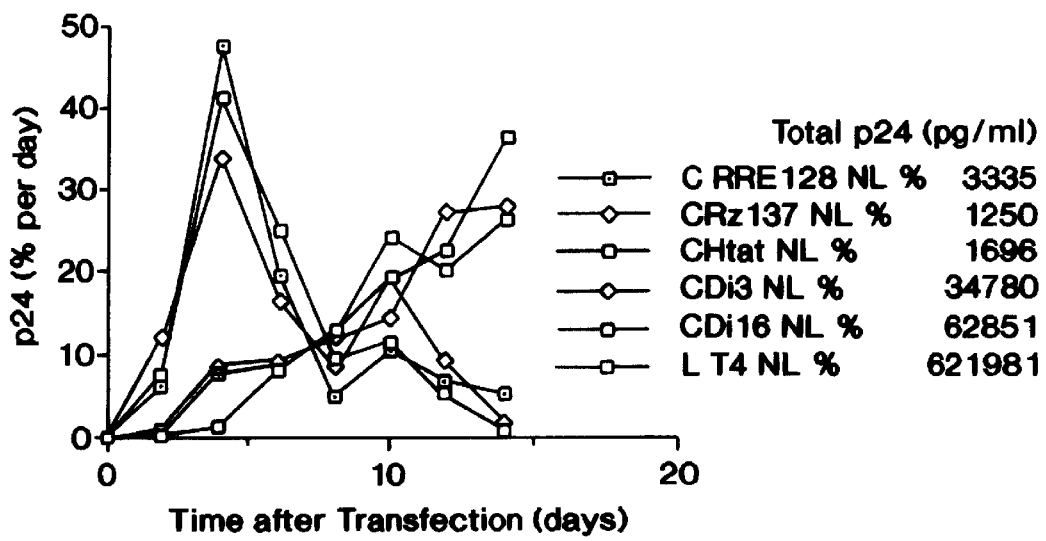

FIG. 12 shows the transfection of selected stable Hela T4 cell lines which harbor the defective interfering HIV provirus HD1, HD2 and HD3, with the infectious HIV clone pNL4-3. The three prototype defective interfering proviral DNAs HD1, HD2 and HD3 were transfected into Hela T4 cells (Maddon, P. J., et al., Cell 47:333–348 (1986)) using a plasmid vector containing the hygromycin resistant gene. Individual cell clones were selected in the presence of hygromycin B. They were picked after two weeks of selection, expanded and tested for their ability to replicate HIV-1. From a large collection of isolated cell clones, a select few are shown in this figure. CRRE128 contains HD3 and CRz137 contains HD2. CHtat is a Hela cell which does not express the CD4 molecule on its surface, and it cannot be infected by HIV. CDi3 and CDi16 contain HD1. Southern blot analyses of these only singly cloned cell lines confirmed the integration of these proviruses. LT4 is the Hela T4 parental cell clone which was used for the generation of the other cell lines. A syncytia forming assay using a vaccinia virus recombinant expressing the HIV env protein (Earl, P. L., et al., J. Virol. 64:2448–2451 (1990)) confirmed the presence of CD4 on the surface of these cell lines.

After transfection with the infectious clone pNL4-3, the release of HIV antigen p24 from these cell lines was determined by ELISA and the results are shown for a period of two weeks. The total amount of p24 released during this time is listed for each cell line. To normalize for potential differences in transfection efficiencies for each cell clone, the release of p24 antigen of each collection day was calculated as a fraction of the total amount of p24 antigen found in the supernatant of these cell lines within the two week period. Note the differences in the kinetics of p24 (virus) release. Cell lines like CDi3, CDi16 and the control LT4 showed high amounts of p24 release with a continuous production of p24 until day 14. This is the result of continuous reinfections of the neighboring permissive cells by the released HIV. In contrast, the cell lines CRRE128, CRz137 and CHtat had a quite different kinetic of virus release. All three showed low amounts of p24 antigen in the supernatant and the infection peaked at about day 4. There was a dramatic drop in virus release during the next 10 days. The kinetics of virus release by CRRE128 and CRz137 was similar to CHtat. Since CHtat lacks the CD4 receptor and CRRE128 and CRZ137 do not, the spread of the infection is obviously not hindered by a lack of CD4 on the cell surface. This strongly suggests that the virus which is released from CRRE128 and CRz137 is less infectious. The decrease in viral infectivity is most likely caused by the expression of CD4/env encoded by the defective interfering provirus HD2 and HD3 which traps the HIV env protein inside the cell. The lack of inhibition with CDi3 and CDi16, which both contain HD1 integrated, suggests that these cell clones are most likely heterogeneous with many cells present which do not contain HD1 and are permissive to HIV replication.

Figure 13:
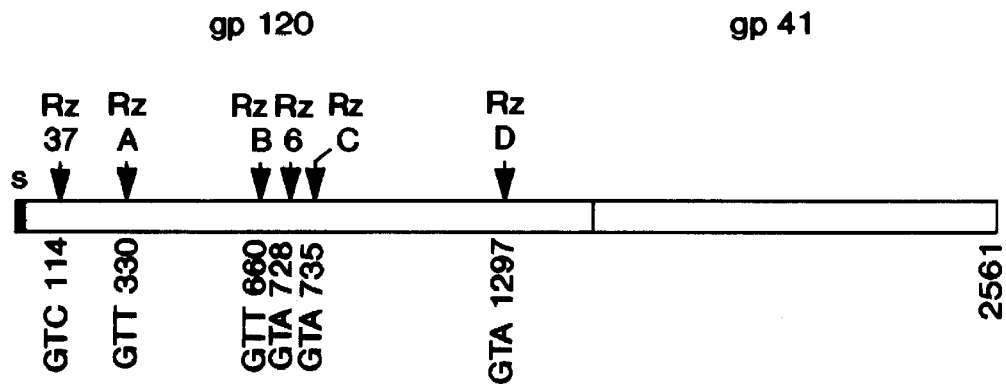

FIG. 13 represents HIV env mRNA against which the two pentaribozymes shown in FIGS. 30 and 31 were synthesized. The sites were chosen based on the nucleotide sequence comparison of different HIV isolates as described in Starcich et al., Cell 45:637–48 (1986). For the construction of the nonaribozyme, these and four additional sites at positions 359, 775, 883 and 996 were selected as shown in FIG. 15.

Figures 14A, 14B:
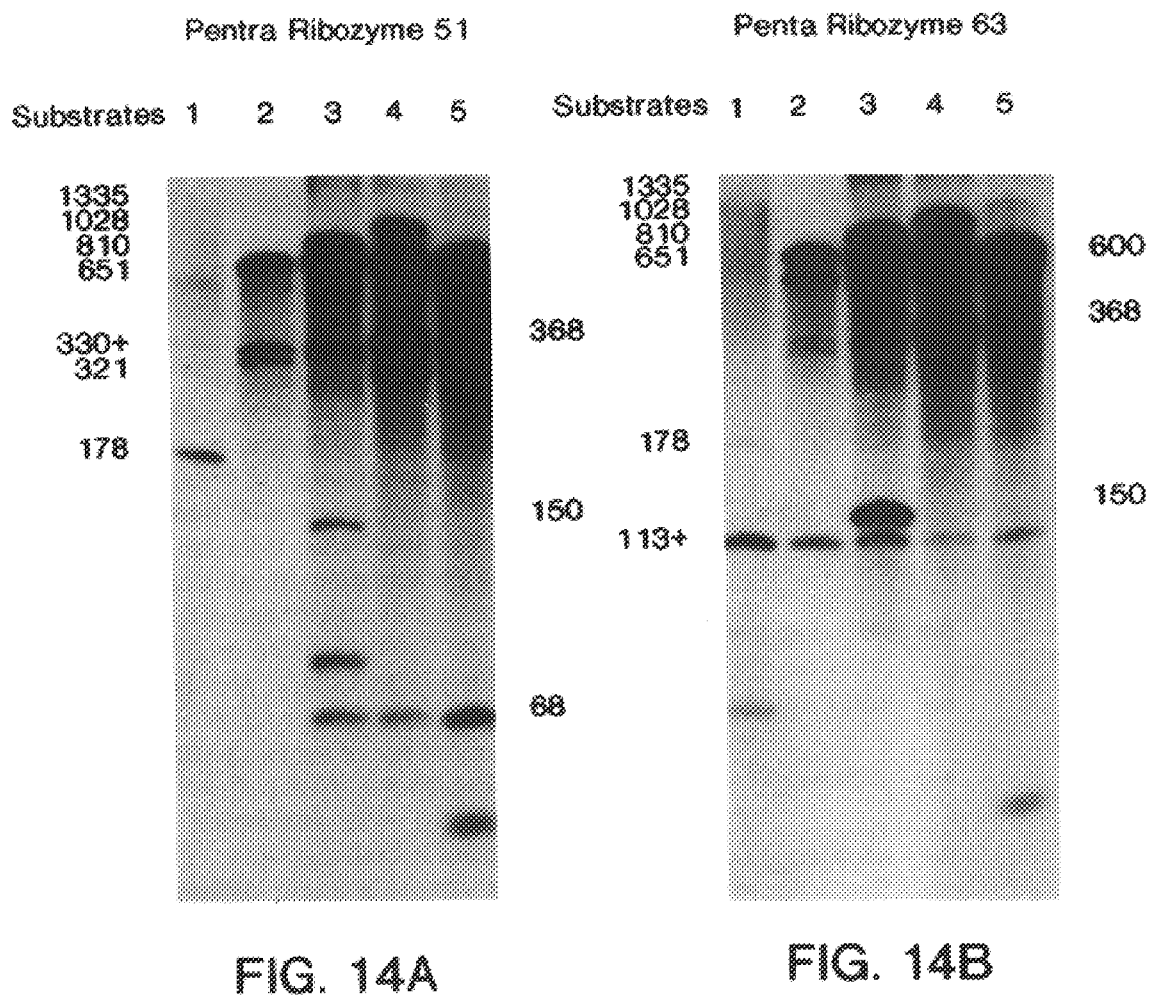
Figure 15:
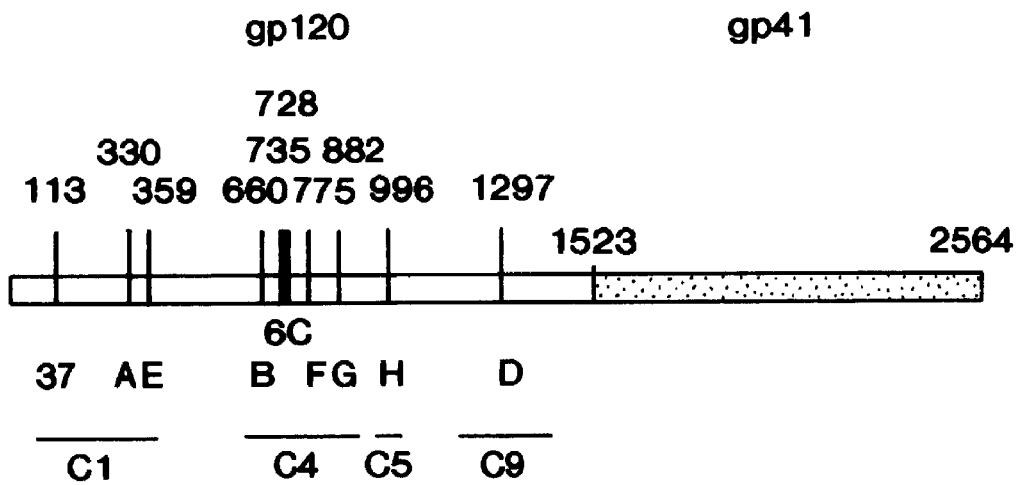

FIGS. 14A and 14B represent digestion of HIV env mRNA by two different pentaribozyme RNAs. Five different radiolabelled substrate RNAs 178 nt. (lanes 1), 651 nt. (lanes 2), 810 nt. (lanes 3), 1028 nt. (lanes 4), and 1335 nt. (lanes 5) in length were transcribed by T7 RNA polymerase in vitro using a clone of the HIV env gene under control of the T7 promoter. These substrate RNAs are a set of different run-off transcripts sharing the same 5' and terminating at the indicated sites with the gp 120 region. The transcripts therefore, contain, depending on their size, the ribozyme target sites listed in FIG. 13. These substrate RNAs were incubated under standard conditions with the two pentaribozyme constructs 51 (FIG. 14A) and 63 (FIG. 14B) which share 4 target sites in env (A, B, C, D; FIG. 13) but differ in the fifth site (6 vs. 37; FIG. 13). This is the reason why both digestion patterns differ slightly. Most digestions were partial with different efficiencies depending on the individual target site. The use of the different substrate lengths and the two different pentaribozymes allowed for the identification of the target sites for the ribozymes which were functional. The digestion pattern indicates that all target sites were used, except target site C. Site C was not functional despite the fact that the correct sequences are present in both, the ribozyme as well as the target RNA. Both pentaribozymes function, therefore, as tetraribozymes under standard digestion conditions. Note that the 1335 nt. substrate was completely cleaved with both pentaribozymes and is absent in lane 5. This result demonstrates the potential superiority of the multitarget-ribozyme approach when it is important to cleave the target RNA at least once and to inactivate it.

FIG. 15 shows selected target sites for the ribozymes to cleave within the HIV-1 env region which were used for the construction of HD4. HD4 contains all the target sites as listed here. The nonaribozyme (63-6) which was inserted into HD3 to create HD4 contains nine individual ribozymes in the following order 37, E, F, G, H, A, B, C, D. Ribozyme 6 was already inserted into the HD3 prototype. The marked regions C1, C4, C5, C9 indicate conserved regions within env according to Starcich et al. (Cell 45:637–48 (1986)).

Figure 16:
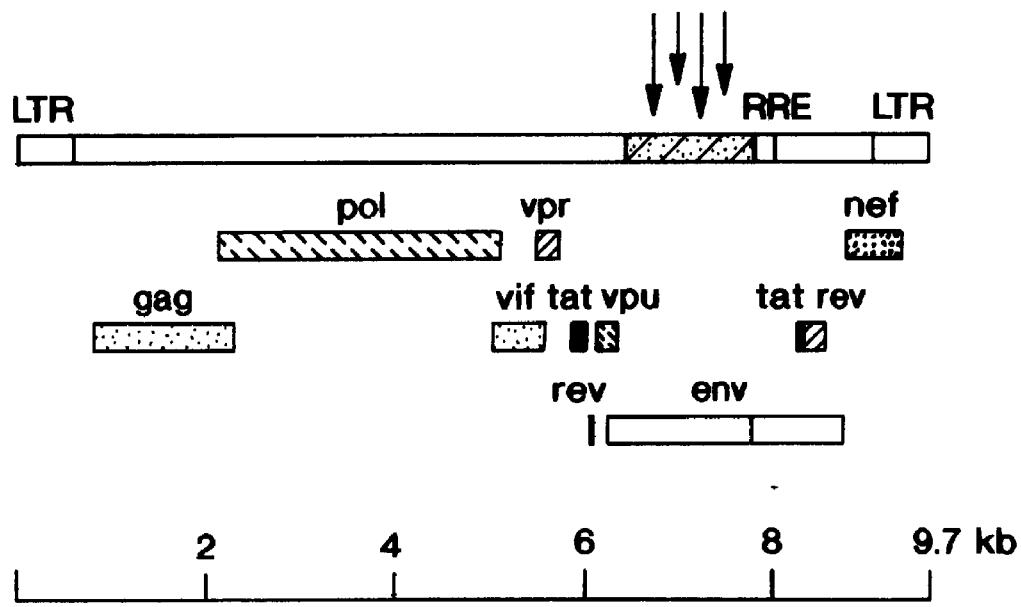

FIG. 16 shows the region in the env gene which is targeted to be cleaved in relation to the positions of all other coding regions and regulatory regions like the RRE and the LTRs. Except for env, none of the other coding regions as well as regulatory regions are affected by the ribozymes. Only unspliced mRNAs are cleaved. Spliced mRNAs encoding the tat and rev regulatory proteins are not targets.

Figure 17:
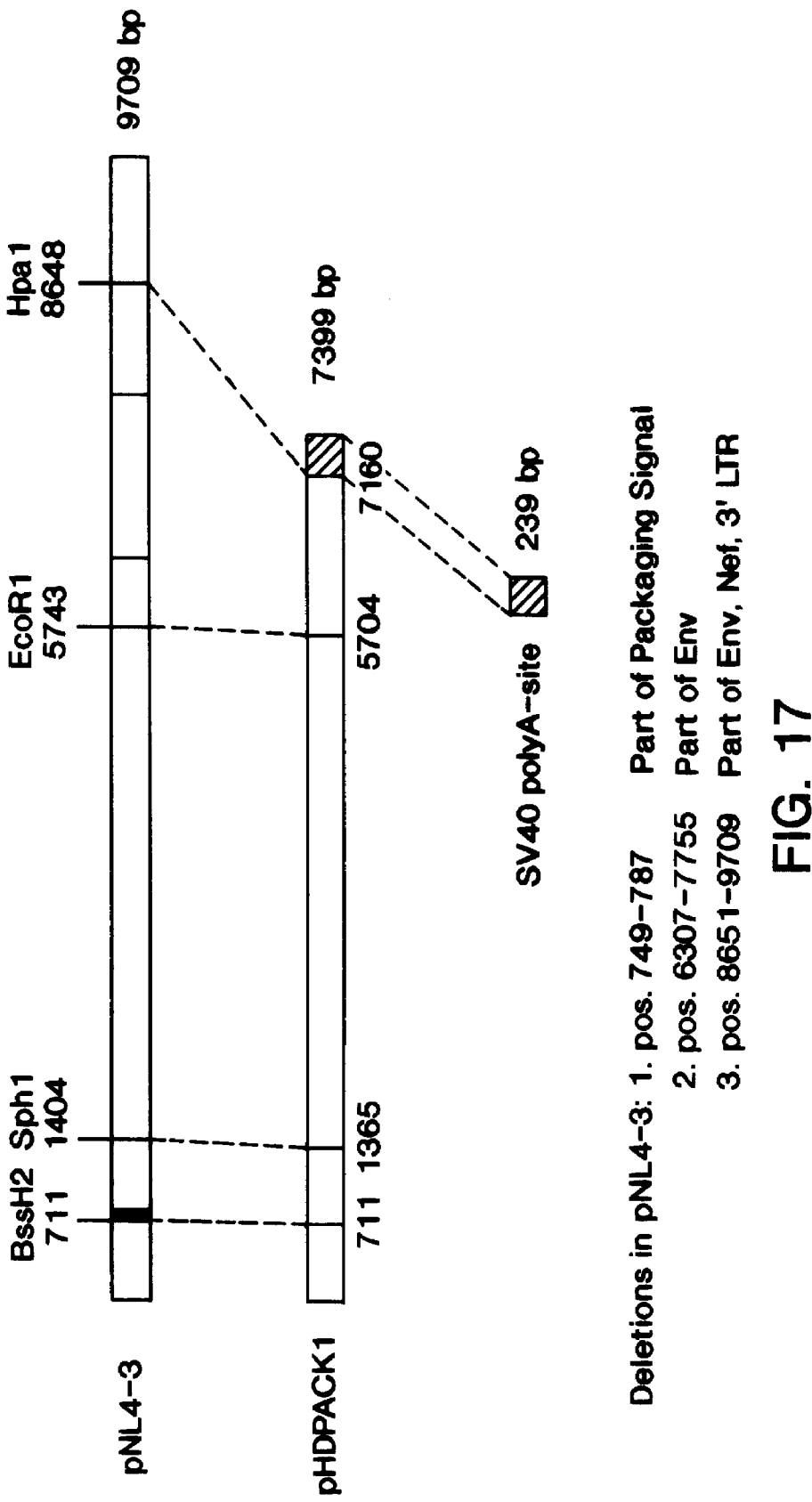

FIG. 17 shows the construction of a helper provirus DNA for the packaging of the targeted defective interfering HIV particles using precise gene fusion techniques (Schubert, M., et al., J. Virol. 66:1579–89 (1992); Yon, J., et al., Nucl. Acids. Res. 17:4895 (1989)). The three deleted areas of pNL4-3 are listed. The borders are precisely defined as indicated at the bottom of the graph. The deletions affect the coding regions of env and nef as well as the packaging and polyadenylation of the parental provirus DNA. The 3' LTR is deleted in its entirety which also removes the polyadenylation site. Polyadenylation of the transcripts is therefore restored by adding a polyadenylation site of SV40 which originates from the vector DNA pJC119 (Sprague, J., J., et al., Virol. 45:773–781 (1983)). This 239 bp polyadenylation region is amplified from this vector DNA by using a polymerase chain reaction (Saike, R. K., et al., Science 239:487–491 (1988)). The final pHDPACK1 construct expresses all HIV structural and regulatory proteins of HIV except env and nef. It can constitutively supply these proteins in trans when integrated into the genome of a host cell line or transiently after transfection. The cell line is selected in the presence of G418 after cotransfection of pHDPACK1 with a neomycin resistant marker gene according to standard procedures. It is also possible to insert a resistant marker gene directly into the unique Hpal site at position 8648 and select cell lines for efficient expression of both the resistant marker gene as well as the other HIV proteins which are expressed from the same 5' HIV LTR promoter, located within the first 640 nucleotides of pNL4-3 as well as in pHDPack 1.

FIG. 18 represents the nucleotide sequence (SEQ ID NO:1:) of DIRz27. This diribozyme is targeted to cleave HIV genomic RNA and/or env mRNA at positions 6334 and 6949 (numbering system pNL4-3).

FIGS. 19A and 19B represent the nucleotide sequence (SEQ ID NO: 2:) of DNA construct HD1, the first prototype defective interfering provirus construct. HD1 was completely sequenced with respect to both DNA strands. The DNA contains both HIV LTRs with the entire gag, pol and most of the env region of HIV replaced by the ectodomain region of CD4. Coexpression of this DNA with HIV DNA results in interference with HIV replication.

FIGS. 20A and 20B represent the nucleotide sequence (SEQ ID NO: 3:)of DNA construct HD1(T7). HD1(T7) contains a T7 RNA polymerase promoter which allows it to precisely transcribe HD1 RNA in vitro as well as in vivo using T7 RNA polymerase. The resulting transcript is almost identical to the transcript that cellular RNA polymerase II transcribes from integrated HD1 DNA.

FIGS. 21A and 21B represents the nucleotide sequence (SEQ ID NO: 4:) of DNA construct HD2. This construct has a monoribozyme inserted which is targeted to cleave HIV env RNA at target site No. 6 as shown in FIG. 15. The ribozyme is inserted at the beginning of the nef gene in HD1 which also eliminates the translational start codon for nef.

FIG. 22A and 22B represent the nucleotide sequence SEQ ID NO: 5:) of DNA construct HD3. HD3 has, in addition, a rev responsive element inserted downstream of the ribozyme region in HD2. This structural element is designed to increase the amount of unspliced defective RNA in the cytoplasm for a more efficient CD4/env expression as well as packaging of the genome. Expression of a full length transcript of the defective interfering particle will be dependent on both regulatory proteins of HIV (tat and rev) which further limits the expression of HD3 in the absence of HIV.

FIGS. 23A and 23B represent the nucleotide sequence (SEQ ID NO: 6:) of DNA construct HD4. This construct has, in addition, the nonaribozyme Rz63-6 (of approximately 400 bp) inserted into HD3 which is targeted to cleave HIV RNA at nine different sites within the gp1120region of env. The interference by the defective proviruses is thereby expanded to included HIV env RNA genome cleavage.

FIGS. 24A–24C represent the nucleotide sequence (SEQ ID NO: 7:) of DNA construct HD5. This construct is identical to HD4 but contains, in addition, short sequences (66 bp) from the beginning of the HIV gag region without encoding portions of gag. Including these sequences increases the efficiency of packaging the RNA into particles.

FIGS. 25A–25C represent the nucleotide sequence (SEQ ID NO: 8:) of DNA construct HD6. This construct is similar to HD5 except it contains even a larger region from the beginning of the HIV gag region (639 bp). This may further increase the level of packaging of the RNA during virus assembly without the expression of any translation of the gag sequence.

FIGS. 26A–26D represent the nucleotide sequence (SEQ ID NO: 9:) of the construct HDPACK1. This construct is identical to HIV with 3 important deletions which eliminate an essential packaging signal, part of the env region and the nef and 3' LTR region which is replaced by the polyA site of the SV40 late genes. This construct when coexpressed with the defective RNAs provides all proteins for the assembly of new defective virus particles.

FIG. 27 represents the nucleotide sequence (SEQ ID NO: 10:) of MONORz37, a monoribozyme targeted to cleave HIV genomic RNA and/or env mRNA at position 6334 (numbering system of pNL4-3).

FIG. 28 represents the nucleotide sequence (SEQ ID NO: 11:) of MONORz6, a monoribozyme targeted to cleave HIV genomic RNA and/or env mRNA at position 6949 (numbering system of pNL4-3).

FIG. 29 represents the nucleotide sequence (SEQ ID NO: 12:) of NONARz63-6, a nonaribozyme targeted to cleave HIV genomic RNA and/or env mRNA at nine different positions: 6334, 6551, 6580, 6881, 6956, 6996, 7103, 7217 and 7518 (numbering system of pNL4-3).

FIG. 30 represents the nucleotide sequence (SEQ ID NO: 13:) of PENTARz51, a pentaribozyme targeted to cleave HIV genomic RNA and/or env mRNA at five different positions: 6551, 6881, 6949, 6956 and 7518 (numbering system of pNL4-3).

FIG. 31 represents the nucleotide sequence (SEQ ID NO: 14:) of PENTARz63, a pentaribozyme targeted to cleave HIV genomic RNA and/or env mRNA at five different positions: 6334, 6551, 6881, 6956 and 7518 (numbering system of pNL4-3).

FIG. 32 represents the structural organization of the nine catalytic sites of the nonaribozyme NONARz63-6 (SEQ ID NO: 12). The positions of the nine, 22 nucleotides long, conserved hammerhead motifs are listed within the molecule. Each motif is flanked on either side by unique, 8 nucleotide long regions which are homologous to the corresponding target sites within the gp120 region of HIV-1 env RNA listed above.

Figure 33:
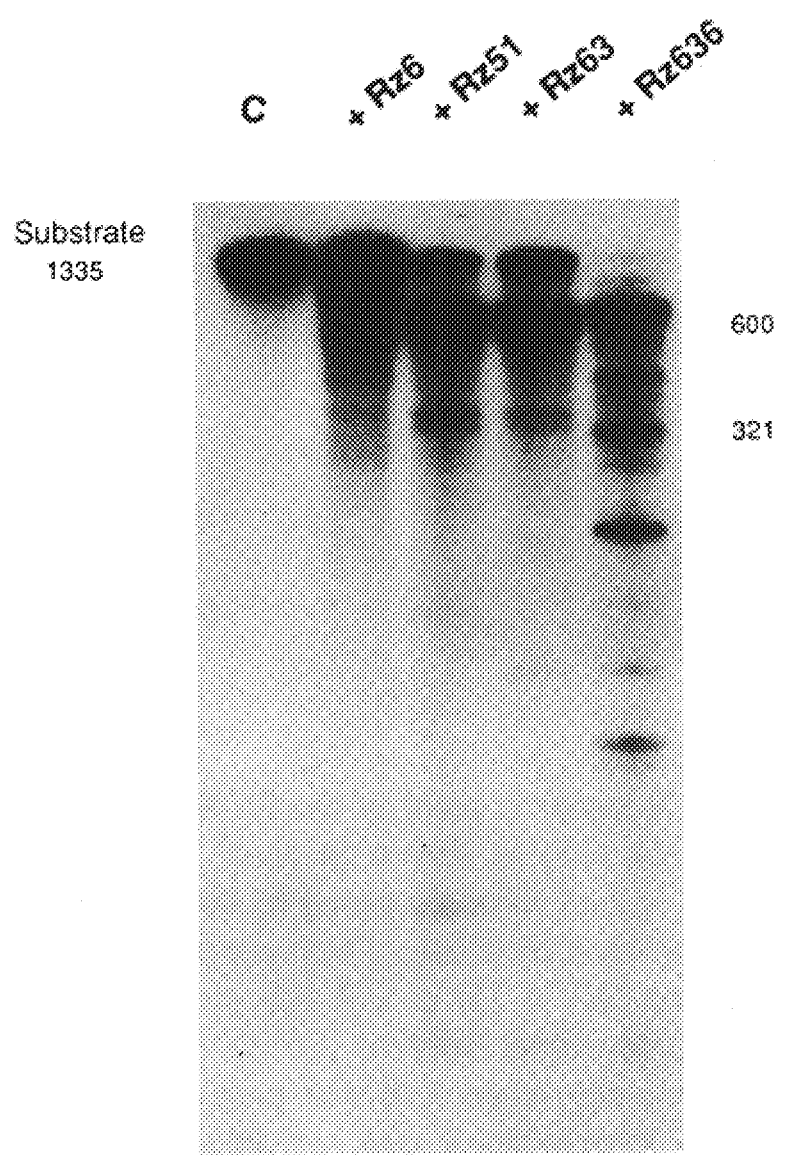

FIG. 33 compares the efficiency of ribozyme cleavage of a 1335 nucleotide long HIV-1 env transcript with either the monoribozyme Rz6, the two pentaribozymes Rz51 or Rz63, or the nonaribozyme Rz63-6. The same amounts of substrate RNA were incubated for 1 hr at 57° C. with equal molar amounts of one of the four ribozyme transcripts. The digestion products were separated on a polyacrylamide gel according to standard procedures. Note that the complete substrate (lane C) was completely degraded in the presence of the nonaribozyme while some undigested substrate still remained with either the monoribozyme as well as with the two pentaribozymes. This demonstrates that at the same molar concentrations, nonaribozyme Rz63-6 is more efficient in destroying the same HIV env RNA target in vitro than either the monoribozyme or the pentaribozymes.

Figure 34:
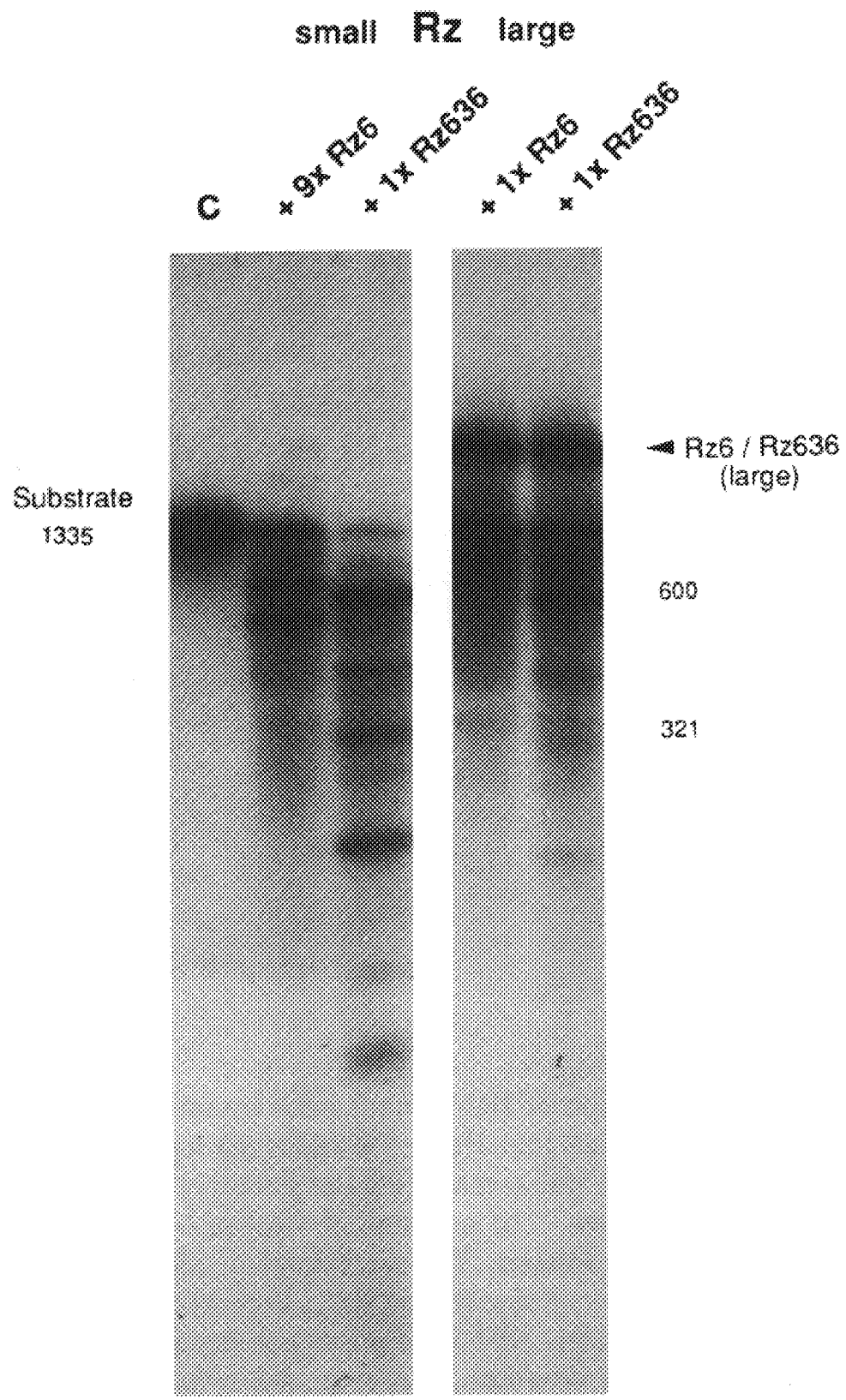

FIG. 34 establishes that multi-target ribozymes unlike monoribozymes, retain much of their activity in vitro when they are a part of a large transcript. The monoribozyme Rz6 as well as other ribozymes, when expressed as large transcripts, do not significantly cleave target RNAs, especially if the target RNA is also large. The figure shows that the nonaribozyme Rz63-6, however, is still active when it is part of a large RNA transcript and even when it is targeted to cleave a large 1335 nucleotides long HIV-1 env RNA. This would also be the case with the expression of the monoribozyme and the nonaribozyme in vivo when they are both part of large defective interfering RNAs HD3 and HD4 (see FIG. 38).

Figure 35:
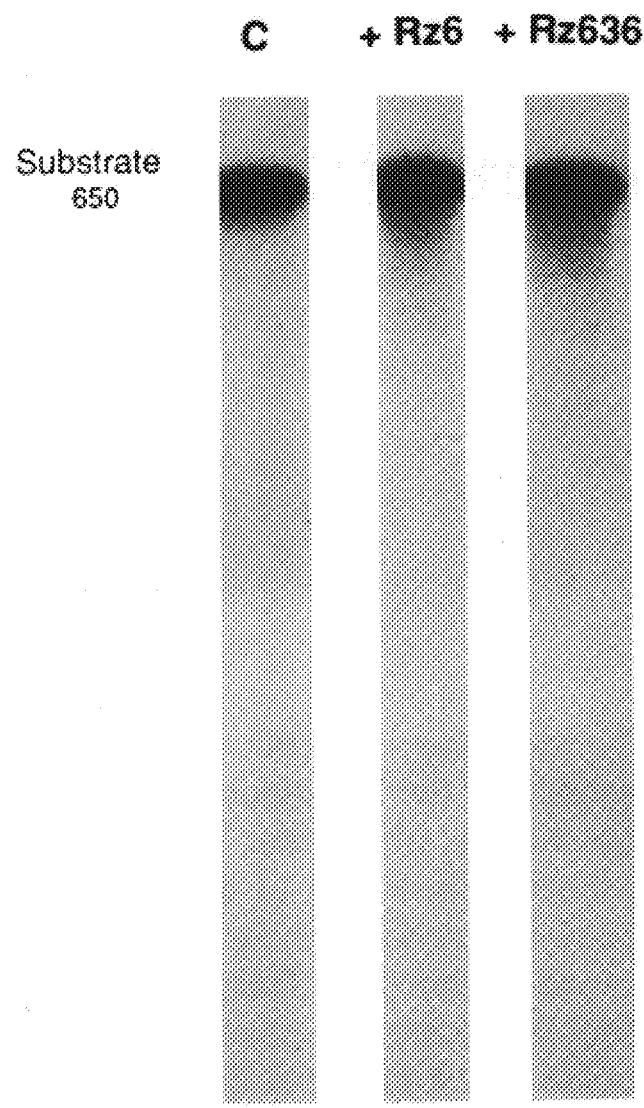

FIG. 35 shows, as a control, that the ribozymes are specific for their target RNA. An unrelated 650 nucleotides long substrate RNA is uncleaved in the presence of either the monoribozyme RZ6 as well as the nonaribozyme RZ63-6 under standard digestion conditions and at the optimal temperature of 57° C. There are no cleavage products below the undigested substrate demonstrating that even the multi-target nonaribozyme does not accept this unrelated RNA as a substrate.

Figure 36:
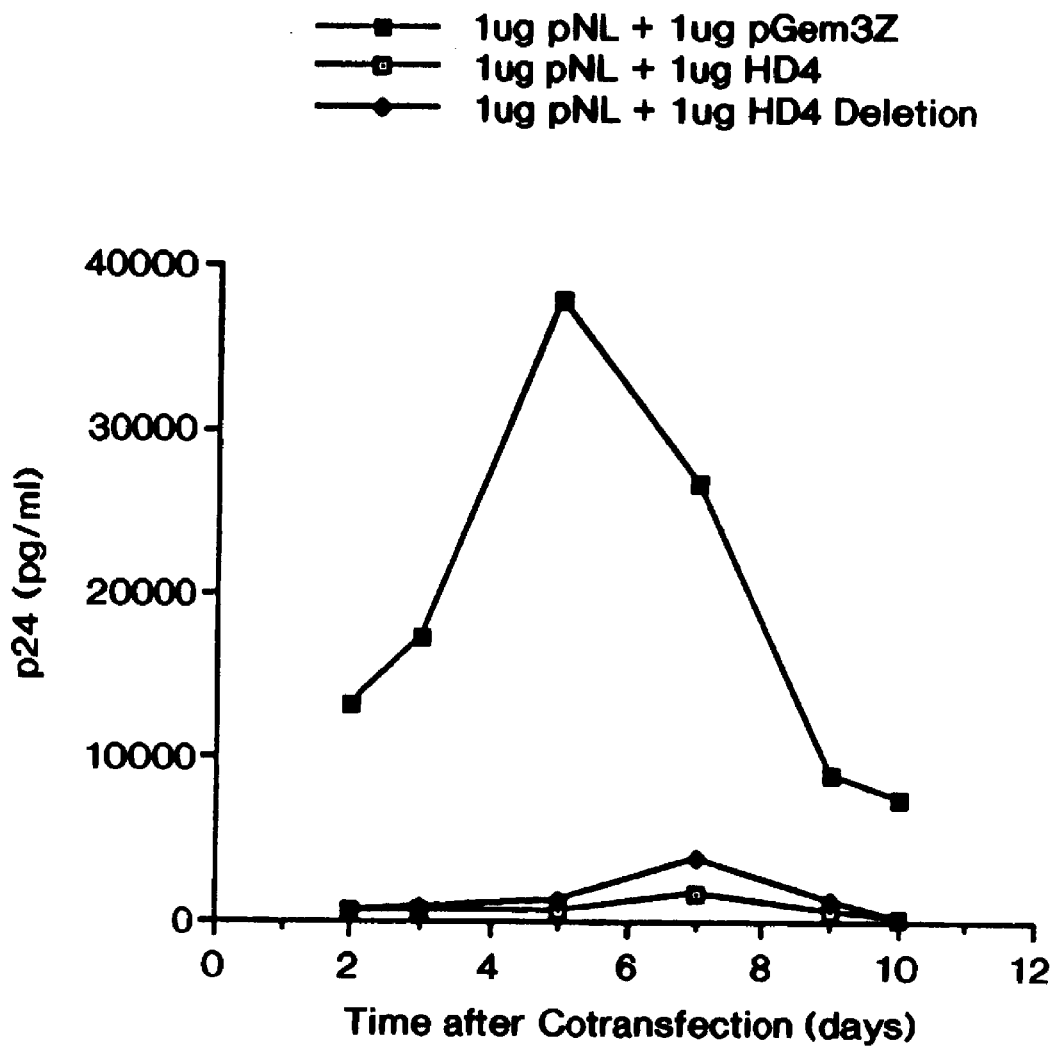

FIG. 36 demonstrates that the nonaribozyme expressed as part of the HD4 construct is functional against HIV-1.

To distinguish the interference action by CD4/env from the action of the nonaribozyme, again, a 527 bp deletion was made like with HD1 and HD3 above (see FIG. 11). HD4 with or without the deletion were cotransfected with equal amounts of pNL4-3 DNA into HeLa T4 cells and the concentration of p24 antigen released into the medium was determined. As can be seen there was a dramatic decrease in released p24 antigen over the ten days in culture. In contrast to the HD3 deletion construct, however, eliminating the expression of CD4/env did not restore HIV-1 replication as measured by p24 antigen release. This result demonstrates that the expression of the nonaribozyme by HD4, which is absent in the third generation construct HD3, is sufficient to dramatically inhibit HIV-1 replication.

Figure 37A:
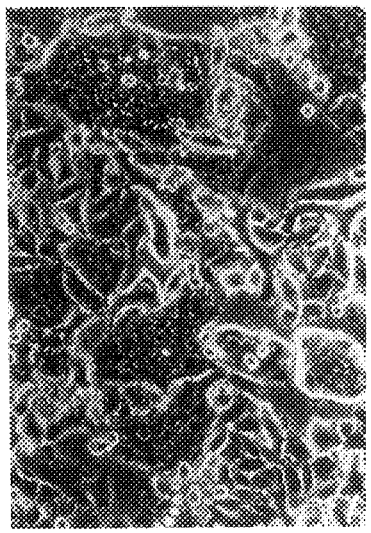
Figure 37B:
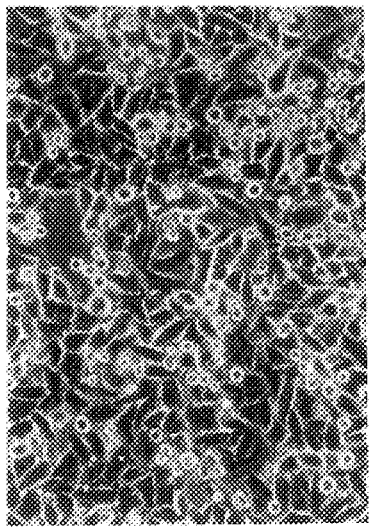
Figure 37C:
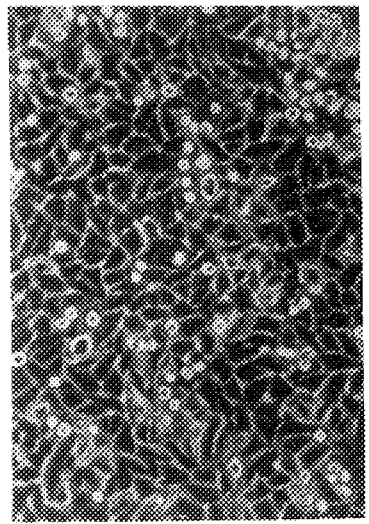

FIGS. 37A–37C establishes that there is an absence of syncytia formation in cotransfections of HIV-1 DNA (PNL4-3) (FIG. 37A) with HD4 which contains (FIG. 37C) or does not contain (FIG. 37B) the 527 bp deletion. This result confirms the observation in FIG. 36 that the nonaribozyme alone which is part of the HD4 deletion construct is able to inhibit HIV-1 replication and cell fusion. The deletion of 527 bp which, in the case of the HD3 deletion construct restores p24 antigen release and syncytia formation (see FIG. 11) by eliminating CD4/env expression, does not permit viral replication because of the nonaribozyme activity.

Figure 38:
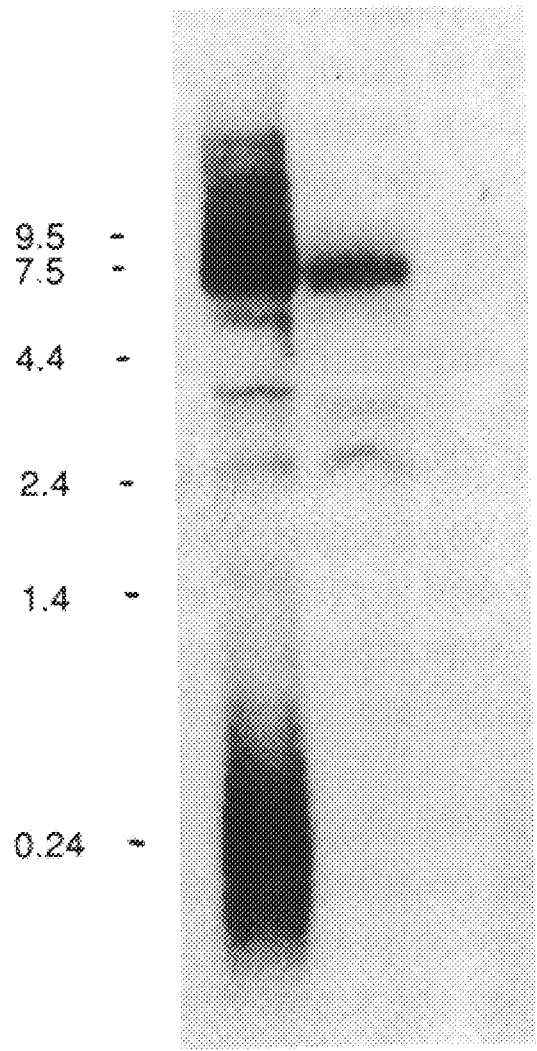

FIG. 38 represents the dramatic disappearance of the env mRNA in the presence of the HD4 construct. To demonstrate cleavage of the HIV env RNA, the present inventors cotransfected a DNA which encodes the HIV env RNA with equal amounts of either HD3 or HD4. The total cellular RNA was analyzed after transfer to a membrane by the Northern blotting procedure.

With the HD3 construct, which contains only a single ribozyme, the amount of env mRNA in the cells is reduced but it is still abundant. In the presence of HD4, however, env mRNA almost completely disappeared. This emphasizes the superior activity of the nonaribozyme by HD4 in vivo as compared to the monoribozyme expressed by HD3. This is consistent with the finding that the HD3 Deletion construct does not interfere with HIV-1 replication but the HD4 Deletion construct does.

FIG. 39 represents a comparison of virus release in the presence of the various DNA constructs emphasizing the specificity and efficiency of interference. In particular, the figure shows a comparison of the level of interference in HeLa cells vs. HeLa T4 cells. The results indicate that the defective interfering HIV DNAs do not significantly interfere with the gene expression of HIV-1. There is only a 50% reduction in the amount of p24 antigen released from HeLa cells in the presence of the HD1 through HD3. With the same constructs, there is more than a 90% decrease in HIV-1 replication in HeLa T4 cells. Although gene expression is not inhibited and roughly the same amount of virus is released from the cells, there is an apparent inhibition in the spread of wild type HIV-1 to susceptible neighboring HeLa T4 cells. This demonstrates indirectly that the makeup of the virus has most likely changed. Released virus appears less infectious. This decrease in infectivity is caused by a lower amount of Env protein in the virus envelope which is downregulated by either CD4/env and/or multitarget-ribozyme, both expressed from the defective interfering HIV-1 DNA constructs. Each experiment represents a summary of a time course and the amounts of p24 antigen are as expected proportional to the extent of syncytia formation.

FIG. 40 represents a summary of comparison of the selected multiple target site sequences from all HIV-1 isolates (about 30) which have presently been sequenced. This Figure reveals that the nonaribozyme would be effective against most, if not all isolates from North America and Africa. Because CD4 is the conserved receptor of HIV-1, which is presumably used by all HIV-1 isolates, this dual inhibition of HIV-1 replication by CD4/env and the nonaribozyme could be quite effective with a low probability for the selection of escape mutants.

Figure 41:
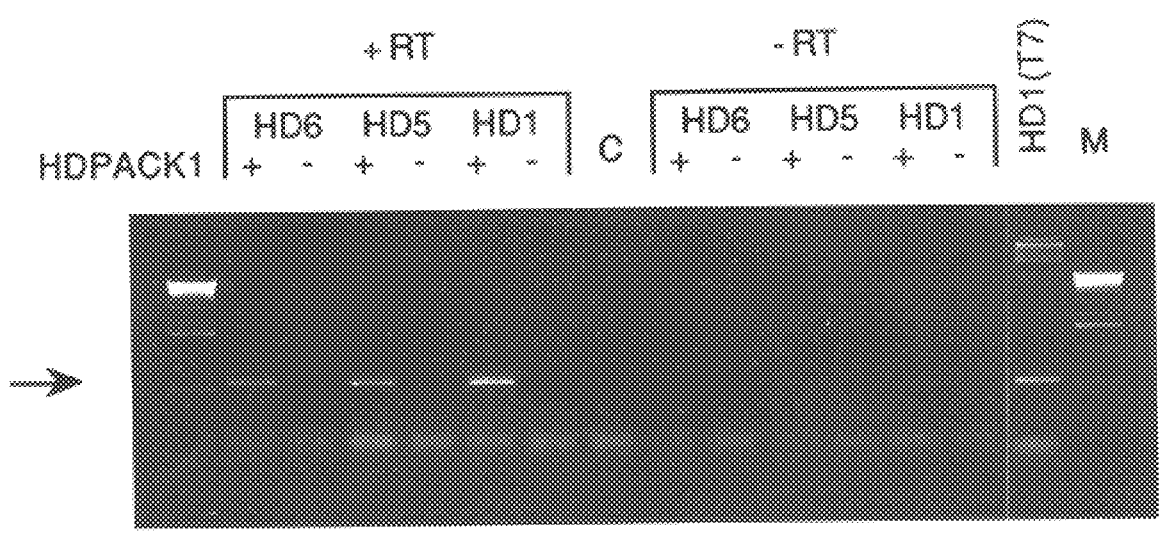

FIG. 41 shows that, after cotransfection of HDPACK1 with the defective interfering HIV-1 DNA constructs HD1, HD5 and HD6 which are shown here as examples, the present inventors found genomic RNA of these constructs in the supernatant of transfected cells. The detection of the RNAs was dependent on reverse transcription (+RT) which was followed by polymerase chain reactions, resulting in a specific 550 bp DNA fragment. Less than 1 ul was necessary for this assay, suggesting a good level of particle production even during the transient coexpression in a low number of cells. The assay was specific for the polyadenylated defective genomic RNA. Because of the choice of primers, the RNA had to be polyadenylated to be accepted as a substrate for reverse transcription. The resultant amplified DNA fragments from HD1, HD5 and HD6 had the correct size. They were only detected in cell supernatants from cotransfections with HDPACK1 DNA. In the absence of HDPACK1, no defective interfering genomic RNA was detected in the medium. This strongly suggests that the defective interfering HIV-1 RNAs were specifically packaged into virus particles which were subsequently released from the cotransfected cells as described in FIG. 1. These particles were also able to band on sucrose gradients. The p24 antigen which they contain was detected at the same location on the gradient as the genomic defective interfering RNA. These defective HIV like particles are safe and any recombinational events between HDPACK1 and the HD1–6 DNAs could not restore a complete HIV genome. The defective interfering particles thus were generated in the complete absence of HIV-1.

DETAILED DESCRIPTION OF THE INVENTION

Several prototypes or DNA constructs have been developed with respect to the present invention, and each of these prototypes differs from its counterparts with respect to the make-up of components found within its genome.

The initial genome prototypes of the defective interfering proviral particles of this invention are shown in FIG. 2. The entire provirus constructs are between 3.4 kb to 5 kb in length. In each case both 5' and 3' LTRs of the parental HIV virus are conserved. The entire coding regions of the parental virus are replaced by the ectodomain region of the human CD4 protein. The replacement starts precisely at the AUG of the gag region up to and includes the last amino acid of the extracellular region of the HIV envelope protein (see the chimeric DNA in FIG. 3). This leaves the transmembrane and cytoplasmic tail region of the env protein intact, followed by a complete nef region and the 3' LTR. This proviral construct, HD1, encodes both the chimeric CD4/env protein as well as the HIV nef protein. A complete construct of this prototype has been assembled, starting with the infectious DNA clone pNL4-3 (Adachi, Akio, et al., J. Virol. 59:284–291 (1986)) and a clone for the human CD4 protein (Maddon, P. J., et al., Cell 42:93–104 (1985)). The complete sequence of this DNA construct was determined as shown in FIG. 19.

Three more prototypes (HD2, HD3 and HD4) can be generated initially starting from this first clone. As shown in FIG. 2, these three clones have insertions in the nef region with the AUG start of nef removed and replaced by the first hammerhead ribozyme sequence. This ribozyme is targeted to specifically cleave the HIV genome or HIV env mRNA at nucleotide 728 within the coding region for the HIV env protein (FIG. 13). (This ribozyme was constructed by the present inventors, and they confirmed the specificity of cleavage in vitro.) In prototype HD3, the ribozyme sequence is followed by the sequence of an approximately 240 bp rev responsive element of HIV (RRE) (FIG. 5) (Malim, M. H., et al., Nature 338:254–256 (1989)) which the present inventors have synthesized by polymerase chain reaction from the infectious clone pNL4-3. This element is inserted into HD2 at a Not 1 cleavage site 3' of the ribozyme sequence. Currently it is not clear whether the RRE will actually be needed. Prototype HD4 is constructed by inserting a non-aribozyme adjacent to the 3' site of the RRE, thereby eliminating a Xho1 to Kpn1 fragment within the nef region. Prototypes HD5 and HD6 will be described below. The sequences of all six prototypes are shown in the FIGURES. Furthermore, methods for the construction of these prototypes are shown in the Examples.

It should also be noted that the present invention covers portions of all sequences shown in the FIGURES (i.e., the 6 prototypes as well as the additional constructs) as well as allelic variations thereof.

The defective interfering viral particles of the present invention have many advantageous properties. For example, it is believed that constructs HD4, HD5 and HD6 (i.e., the fourth, the fifth and the sixth generation constructs) can:

1) target HIV infected cells by specifically binding to HIV env protein expressing cells and entering these cells,
2) interfere with the replication of HIV in these cells through the expression of a chimeric CD4-HIV env protein as well as by the expression of additional gene(s) and/or nucleotide sequences, which enhance the interfering capability of the defective provirus like novel multitarget-ribozymes,
3) replicate using HIV itself as the helper virus for the source of the structural and regulatory proteins of the virus,
4) transfer this ability to interfere with HIV replication to other HIV infected cells and repeat the cycle, and
5) transfer the ability to interfere with HIV replication to uninfected CD4+ cells, causing protection and intracellular immunization of these cells against high levels of HIV production.

These five features, which are outlined in more detail in the legend to FIG. 1, are important elements of this invention. It is hoped that all of them may be used in concert to downregulate the replication of HIV, and thereby slow the spread of HIV within the various populations of HIV infected cells. These targeted defective interfering particles may circumvent the natural exclusion of superinfection, which is normally caused by the downregulation of the receptor on the cell surface. This may be achieved as proposed in some sort of a role reversal, in which the HIV infected cell will provide the membrane fusion function, while the targeted defective interfering HIV virus provides the receptor function by binding to the fusogenic env protein to its surface (FIG. 1).

FIGS. 7A–7C demonstrate that the chimeric CD4/env protein encoded by defective provirus construct (HD1) can be translated in vitro from an in vitro transcript of HD1(T7) (see FIG. 6) using T7 RNA polymerase. The CD4/env chimeric membrane bound protein is like the chimeric CD4/G protein which consists of the ectodomain of CD4 precisely fused to the transmembrane and cytoplasmic domains of the Vesicular stomatitis virus glycoprotein G, and which is functional as a receptor in a syncytia forming assay in vivo when expressed with the HIV env protein in Hela cells. Expressed at increased levels, syncytia formation is inhibited by either one of the chimeric receptor proteins. At lower CD4/env or CD4/G concentrations, when coexpressed with the HIV env protein, the cells fuse forming multinucleated cells like during a normal HIV infection of CD4+ cells. Interestingly, as FIG. 8F , panel F shows, only a slight increase in the expression of the chimeric CD4/env protein over the env protein results in an inhibition of syncytia formation when coexpressed with the HIV env protein in Hela T4 cells. This suggests that a fine balance exists between the surface expression of both proteins. Thus, downregulation of env can be with low amounts of CD4/env. Since CD4/env is functional in a syncytia forming assay, it can, therefore, also be expected, that it can be used as a functional receptor when it is inserted into the viral envelope and binds to env protein expressing cells. Whether this binding will lead to membrane fusion and efficient infection is still uncertain at this time. However, the present antiviral strategy is not completely dependent on this function.

Coexpression of HIV DNA together with the defective interfering HIV prototype DNAs HD1 through HD3, which all encode the chimeric receptor, results in a significant interference with wildtype virus production as shown in FIG. 9 for p24 antigen release and in FIGS. 10A and 10B for the inhibition of syncytia formation. This interference is presumably caused by the expression of CD4/env in these cells. This is supported by the result that the cotransfection of HD1 and HD3 deletion mutants, which have the amino-terminal region of CD4/env deleted for 527 bases (including the transnational start codon), does not inhibit HIV replication as summarized in FIG. 11.

In addition, as mentioned above, the present inventors have selected a number of different stable Hela T4 cell lines which individually harbor the defective provirus constructs HD1 through HD3. Some of these cells lines strongly interfere with HIV replication after transfection with HIV DNA or after infection with HIV virus stock. Furthermore, data on the kinetics of virus release from these cells (FIG. 12) demonstrate that the expression of the wildtype virus is not completely inhibited in such initial DNA cotransfections, as measured by p24 antigen levels in cell supernatants at early times after transfection. Released virus particles are inefficient in reinfecting neighboring CD4-positive cells. This is exactly what is expected from the antiviral strategy. It strongly suggests that the makeup of the virus released from these cells has changed, and that the virus particles lack or may have lower amounts of the HIV env protein, as shown in FIG. 1. These data strongly suggest that this interference element of the invention performs as intended.

Furthermore, the ability of this defective provirus to interfere with the replication of the wildtype HIV virus may be increased by inserting multitarget-ribozymes into the genome of the constructs or prototypes. This interference has to be highly specific for the wildtype HIV, and it should not permit the wildtype virus to escape this interference as is typical for many antiviral approaches with single targets.

Mono-, di- and pentaribozymes can be created which are specifically designed to cleave the HIV env mRNA and the HIV genomic RNA at precise and relatively conserved sites within the gp 120 ectodomain region of env (Starcich et al., Cell 45:637–48 (1986), FIG. 13). All of these constructs may cleave HIV env mRNA in in vitro assays as shown for the pentaribozymes in FIG. 14. (Monoribozymes have previously been shown by others to be functional against HIV in vivo (Sarver, N., et al., Science 247:1222–1225 (1990)). It can, therefore, be expected that multitarget-ribozymes will also be effective in vivo. Clearly, the intended purpose of the multitarget-ribozymes of the invention, which are part of the defective interfering HIV genome, is to lower the amount of env produced by wildtype HIV, but also to cleave and thereby inactivate the HIV genome itself before packaging into virus particles. This will lower the total amount of infectious HIV genomes in circulation without affecting the amount of the defective genome. Therefore, from the fourth HD generation on, the defective interfering particles are specifically designed to interfere with HIV-1 replication by two mechanisms: the downregulation of env on the cell surface by CD4/env expression and the cleavage of env RNA or HIV-1 genomic by the multitarget-ribozymes. In fact, the genomic RNAs of the defective, interfering particles themselves have catalytic activity and function as multitarget-ribozyme.

Since HIV mutates rapidly, like most RNA viruses, the present invention also encompasses the construct, cloning and sequencing of a novel nonaribozyme which is targeted to cleave at nine different, but relatively conserved sites within the gp 120 region of env. The pentaribozyme (actually a functional tetraribozyme in vitro) which is shown in a functional assay in FIGS. 14A and 14B is part of this construct. The additional target sites are listed in FIG. 15. Such a combination should make it virtually impossible for the virus to escape inactivation by a single point mutation. Again, the expression of the other viral proteins as well as the expression of the defective interfering virus will not be affected (FIG. 16). The synthetic nonaribozyme construct, which is approximately 400 nucleotides in length, can be inserted into the defective interfering virus genome HD3 at the Xho1-Kpn1 sites shortly downstream of the rev responsive element. This insertion eliminates 118 bp of the nef coding region. Nef is not needed for virus replication. Contrary to earlier suggestions, it may actually enhance pathogenesis, as was recently shown for the nef protein of the simian immunodeficiency virus (Kestler III., H. W., et al., Cell 65:651–662 (1991)). The nucleotide sequences of all of the ribozyme constructs are shown in the figures. Thus, the multi-target ribozymes should increase the ability of the defective, interfering particles of the present invention to interfere with HIV viral replication. Such multi-target ribozymes are discussed, in great detail, below.

The packaging of HIV genomic RNA into virus particles requires specific sequences which, at this time, are not well defined. Most importantly, however, it has already been shown that including the first 66 nucleotides of the HIV gag gene region allows packaging of the RNA (Poznansky, M., et al., J. Virol. 64:1920–1926 (1990)). Thus, construct HD5 shall contain this additional short stretch of nucleotides (prototype HD5, FIG. 2). At the same time, the AUG of the gag gene may be mutated by site specific mutagenesis using synthetic oligonucleotides. The first AUG in the defective interfering virus genome can be that of the chimeric CD4/env gene.

The efficiency of packaging may be increased by including even more sequences of the gag region. In an additional construct, up to 639 bases of the beginning of the gag gene can be included, again, with the first and only AUG of gag removed. The first AUG of the transcript will again be from the open reading frame of the chimeric CD4/env gene. Additional translational stop codons can be introduced into this 639 bp gag region to prevent any recombinational events with naturally occurring defective HIV genomes which could result in a restoration of a functional gag region (prototype HD6, FIG. 2). The insertion of these additional gag sequences will probably allow more efficient packaging of the defective, interfering HIV genomic RNAs.

Overexpression of the chimeric CD4/env protein encoded by the defective interfering particle as described above, together with the cleavage of env mRNA by the multitarget-ribozyme causes a downregulation of the HIV env protein on the surface of the infected cell. At the same time, the concentration of the CD4/env protein will increase at the plasma membrane. Its expression is not affected by any ribozyme cleavage. At the site of assembly of the defective, interfering HIV particle, this receptor can then be packaged into the viral envelope. In a very similar situation, a chimeric CD4 molecule has previously been inserted efficiently into the envelope of vesicular stomatitis virus particles (Schubert, M., et al., 66:1579–89 J. Virol. (1992)). The insertion of a chimeric CD4 molecule has also been shown for avian leukosis virus (Young, J. A. T., et al., Science 250:1421–1423 (1990)). Thus, it is likely that the chimeric receptor will also be inserted into the defective interfering particles. Since the chimeric receptor is functional during membrane fusion of two cells, it will probably also be functional during the membrane fusion when inserted into the viral membrane. It is important to point out that HIV particle formation does not require env and can be carried out by gag or gag-pol gene products of HIV.

To initially generate and replicate the defective interfering HIV particles, a packaging cell line for HIV is needed. A stable cell line which expresses high levels of the human CD4 protein on its surface is preferred. A defective HIV provirus (pHDPACK1 as shown in FIG. 17) may be used to generate a packaging cell line. This defective packaging provirus is specifically designed to prevent packaging of its own genome, but it promotes efficient packaging of the defective interfering HIV RNA genome. The HIV provirus of the packaging cell line also does not encode a complete envelope protein. The nef protein region and the 3' LTR are also deleted. All other proteins, however, are functionally expressed, including all regulatory proteins. For this reason, the rev and tat encoding exons within the env region will be retained in the packaging helper provirus. To reduce or to rule out packaging of its own RNA, the region located between the splice donor and the AUG of the gag open reading frame, which is essential for packaging, may be removed without affecting gag protein expression (Aldovini, A., et al., J. Virol. 64:1920–1926 (1990)). These DNA constructions can easily be carried out using the gene fusion methods which have been previously developed (Schubert, M., et al., J. Virol. 66:1597–89 (1992)).

Finally, the DNA of the defective interfering HIV proviral genomes will be inserted into the genome of the packaging cell line by cotransfections with a selectable marker DNA. Producer cell lines can thereby be selected. Supernatants of these cells will then contain the defective interfering HIV virus which carries the CD4 as well as the chimeric CD4/env in its envelope. These particles which are free of wildtype HIV virus will be purified and concentrated, after which they are ready to target HIV env expressing cells.

Alternatively, the defective interfering virus can also be targeted to CD4+ cells by the additional coexpression of env in the cell line. It is almost certain, that a small portion will escape inactivation by the multitarget-ribozymes as well as escape the arrest by CD4/env in the endoplasmic reticulum.

It should be noted that chimeric membrane bound CD4 molecules, other than the CD4/env protein, can be utilized for the purpose of interfering with HIV replication. CD4/G for example, was mentioned above. Furthermore, it may be possible to use the complete human CD4 molecule for purposes of the present invention instead of a chimeric protein. For syncytia formation, only the ectodomain of CD4 is required. The transmembrane and cytoplasmic portions of the construct can be from other proteins. CD4/G functions in the same manner as CD4/env. Thus, other chimeric CD4 molecules and the complete CD4 receptor should also function in the same manner as CD4/env.

After the replication of the defective virus in a selected packaging cell line (or generated by cotransfection) and the purification of the particles by standard filtration and ultracentrifugation procedures, the virus particles are suspended in sterile isotonic solutions for the intravenous administration of the particles into HIV infected patients. Depending on the state and the extent of the HIV infection within the patient, a dose of about 1 million to 1000 million defective particles can be administered slowly by transfusion in about 300 ml of solution to assure efficient mixing of the virus with the entire blood of the patient and to increase the chance of the defective particle meeting its initial target cells, the HIV-1 expressing cells. During the asymptomatic phase of the disease, the patient usually has a low number of about 1/10000 T4 lymphocytes infected which express HIV antigen. It is therefore crucial that a close contact is established for the initial infection by the defective virus. Alternatively, this can also be achieved by removing about 50 ml of blood from the HIV infected patient, partially purifying the T lymphocytes and monocytes and, after infection with the defective interfering particles in vitro, returning these cells back to the patient. This allows the establishment of a close proximity between the infected cell and the defective virus, in a small volume, with fewer defective viruses needed and a higher success rate for the infection, under conditions which can be controlled better.

It should be emphasized that the defective interfering particle, when administered as outlined above, will not have an immediate effect on the patient. The initial infection with the defective virus will not lead to a replication of the defective interfering HIV virus if the patient was not infected by HIV-1. In the presence of HIV, however, the defective virus will spread throughout the body and interfere with the replication of HIV itself. Over a period of many months and possibly years, the spread of HIV itself will be limited or even halted. If the spread is limited before it comes to a depletion of the T4 helper cell population, the onset of AIDS will be delayed. The therapy can basically be administered at any time after diagnosis; however, if the spread of the virus can be slowed early on, therapy will be more effective.

As pointed out above, the spread of the defective interfering HIV virus particles is dependent on the presence of HIV, since by itself, it is replication incompetent. The defective virus, therefore, must follow HIV and only then will it be able to downregulate the production of new infectious HIV in these cells. This will occur particularly in cells which are not latently infected, but constantly produce low amounts of HIV without being killed. To follow HIV throughout the body will probably take a long time. Depending on the time passed since the initial infection as well as on the extent of the virus spread, it may take the defective virus years to catch up, particularly in macrophages within the various tissues and the brain.

The anticipated initial, prime target of the proposed targeted defective interfering HIV particles is the low level of HIV producing monocytes/macrophages which are considered to be the reservoir of the virus. HIV infected T4 helper cells as well as their parental stem cells will also be infected by the particle. Viral replication in these cells, however, is usually rapid and they are quickly killed. Consequently, the defective interfering particle may possibly not be present or may not have enough time to prevent the killing of T4 helper cells. Therefore, the initial stage of the antiviral strategy may be more directed towards monocytes/macrophages, although their access is limited. The second stage of the antiviral strategy involves the important spread of the interfering genes to CD4+ cells, which are infected by the defective virus through env on its surface.

The half life of HIV in tissue culture is relatively short, possibly because of the instability of the HIV envelope protein, its proteolytic cleavage, and the loss of the gp 120 subunit of the HIV envelope protein. The chimeric CD4-envelope protein is possibly more stable, because it is a less complex molecule. This factor will prolong the functional half life of the defective particle and increase its chances of chasing and catching up with the HIV producing cells. Latently infected cells are, of course, not the target of the defective interfering particle, unless they express CD4 on their surface and the defective particle carries env. They will, however, become a target, as soon as HIV is activated. Since latently infected cells are also not constant producers of infectious virus, they neither contribute to the spread of the virus nor the generation of new variants.

If all elements of this invention perform as anticipated, the invention will be most effective after several weeks, months or possibly even years. Since AZT delays the onset of AIDS by one or two years, it is preferable that any therapy be combined with AZT or any other safe drug which may have a negative effect on the replication cycle of HIV. The defective interfering virus of this invention will be affected by the same treatments as HIV itself. While AZT affects the reverse transcription before integration has taken place, interference by the defective virus occurs after integration and at the level of gene expression and viral assembly giving rise to particles which may either lack the env protein or lack HIV genomic RNA. Both particles are noninfectious to most, if not all, cells.

It is important to emphasize that the invention can also be used in the form of a gene therapy of precursor cells after the simple removal of an essential packaging signal (Aldovini, A., et al., J. Virol. 64:1920–1926 (1990)) by gene fusion using a polymerase chain reaction (Saike, R. K., et al.). In particular, when the defective proviral DNA is inserted into a precursor cell of the T4 helper cell lineage, it can be expected that HIV infections of the progeny cells would result in interference with HIV replication and a decrease in the amount of infectious HIV released from these cells, thereby limiting the spread of the virus. In contrast to mobile defective interfering particles, with the gene therapy the interfering genes are only spread through cell division. Even the early nonpackaging provirus constructs, when inserted into the genome of selected Hela T4 cell clones, can protect the cell population from massive HIV replication and spread in tissue culture. The CD4/env is still able to interact with the HIV env protein inside the cell (Buonocore, L., et al., Nature 345:625–628 (1990)) and the ribozymes can still cleave the HIV genome and env mRNAs. In a "traditional" gene therapy approach, released particles, however, would not carry the defective genome, and the interfering genes would not be passed on by a mobile virus particle.

Finally, all of the DNA constructions described in this invention can be done easily with gene fusion methods previously developed (Schubert, M., et al., J. Virol. 1579–89 (1992); Yon, J., et al., Nucl. Acids. Res. 17:4895 (1989)).

This allows the fine tuning of the efficiency of the invention in the future with minimal efforts. This specific combination of nucleotide sequences and the resultant newly created biological properties of the mobile defective interfering HIV particles, makes this invention unique and decisively different from the intracellular immunization gene therapy of stem cells. With infection rates as high as 1/40 individuals in some parts of the world, the conventional gene therapy can technically not be applied to very large numbers of patients, because it is very laborious and there are simply not enough physicians. The invention described herein promotes itself in HIV infected individuals independent of the viral strain. A preparation of the defective virus could easily be applied in a large number of infected individuals.

Returning to the concept of multiribozymes, as noted above, the present inventors have established that multitarget-ribozymes are able to specifically and efficiently cleave a substrate RNA at multiple sites in vitro. More importantly, when coexpressed with HIV-1 intracellularly, they are able to inhibit HIV-1 replication. Multitarget-ribozymes have highly desirable properties as compared to monoribozymes. Multitarget-ribozymes, not only maintain the target specificities of the individual ribozymes but also significantly raise the overall cleavage efficiency per catalytic RNA molecule. These data are encouraging for the successful future use of multitarget-ribozymes against cellular RNAs. For any antiviral strategy which employs ribozymes, the use of multitarget-ribozymes may be essential. It is likely to increase the chance for a prolonged effectiveness, and multitarget-ribozymes could be further developed to be effective against many wild type HIV-1 variants in different cell types.

Error rates of RNA polymerases or reverse transcriptases reaching up to about $10^{-4}$ (Holland et al., Science 215:1577 (1982)) have been reported (Schubert et al., J. Virol. 51:505–14 (1984)) and represent a serious problem for the successful use of any nucleotide sequence dependent antiviral strategy. It is highly probable that the selective pressure exerted by a single ribozyme would be overcome very fast. A very high frequency of mutations between different cDNA clones of vesicular stomatitis virus, a lytic negative strand RNA virus, which had been plaque purified just prior to the cDNA cloning (Holland et al., Science 215:1577 (1982) has been reported (Schubert et al., J. Virol. 51:505–14 (1984)). These data suggest that a virus with an altered and possibly resistant cleavage site may already exist within the virus population after a single replication cycle. It is likely to be selected. The use of multitarget-ribozymes therefore appears crucial.

Multitarget-ribozymes could be used in a gene therapy to inactivate the expression of a gene. They could, for example, be used in an intracellular immunization of stem cells (Baltimore, Nature 335, 395–961 (1988)). Multitarget-ribozymes could also be designed to target several RNAs simultaneously. It is important to note, however, that although the ribozyme target sites described here are all directed against the HIV-1 env exon, this region also represents an intron of the unspliced mRNA precursors for the regulatory proteins Tat and Rev. Their expression could also be affected if the ribozymes are functional in the nucleus.

Future detailed experimentation will be required to distinguish the effects of the ribozymes on the levels of individual mRNAs, like for env, tat and rev, but also on the level of HIV-1 genomic RNA itself. They could all contribute to the inhibitory effect of the multitarget-ribozymes on HIV-1 replication as demonstrated herein. The gp120 region was chosen as the target to selectively inhibit Env protein expression and to decrease the synthesis and packaging of complete genomic RNA, which are both important parts of the present inventors' antiviral strategy. The less impaired continued expression of the other structural and regulatory proteins may potentially provide helper functions to allow propagation of novel, targeted defective interfering HIV-1 particles. The use of multitarget-ribozymes against HIV-1 has to be viewed in the context of this antiviral strategy. It is important to note that this strategy does not require that the ribozymes cleave every single target RNA to completion.

The largest ribozyme described herein contains nine different units. The number of individual ribozymes within multitarget-ribozyme could potentially be further increased. Alternatively, repeating the same ribozyme motif many times within the same RNA is less likely to result in a dramatic increase in cleavage efficiency. This increased cleavage efficiency of multitarget-ribozymes may, in part, be the result of a cumulative efficiency of all individual ribozymes. A potential increased accessibility of the multitarget-ribozymes for the substrate may explain the high cleavage efficiency when multitarget-ribozymes were part of a large transcript like the one expressed from HD4. Additional studies are required to evaluate any potential effect the sequential order of the monoribozymes within the multitarget-ribozyme might have on cleavage efficiency.

The proposed use of multitarget-ribozymes against, for example, a retrovirus should help maintain effectiveness for a longer period of time. It will be less likely that the population of viral RNAs will escape from all potential cleavages at once. The search for more efficient ribozymes which could be combined into such multitarget-ribozyme constructs, may in the future significantly contribute to the length of time they will be effective against HIV.

The ten conserved target sites described herein (see FIG. 15) were originally chosen based on the sequence information from only five HIV-1 isolates (Starcich et al., Cell 45:637–48 (1986)). However, within the gp120region, not many more conserved sites were available. A comparison of the target sequences of all, approximately thirty HIV-1 isolates is shown in FIG. 40. The number of nucleotide changes each isolate carries within each of the ten target regions are listed. Surprisingly, most of the ribozymes described here would be effective against every North American isolate presently sequenced. The effects of some of these changes on multitarget-ribozyme activity are indicated. Any ribozyme activity which can be expected to be completely abolished by the changes are marked by boxes. These changes would affect the essential GU cleavage site directly. Changes which are listed in parenthesis do not affect activity. All other nucleotide changes can be expected to affect ribozyme activity to some extent. However, the degree to which such ribozyme activity would either be decreased, or possibly even increased, is currently unknown. With the more distantly related African HIV-1 isolates, the majority of the viral RNAs would still be cleaved by at least two of the ten ribozymes described here and possibly by one or two more ribozymes. These comparisons are encouraging for the potential effective use of multitarget-ribozymes against different wild type HIV-1 strains. The data suggest that a further increase in the number of conserved target sites together with their combined multitarget-site activities may allow the development of an "inescapable" multitarget-ribozyme which may be able to withstand the challenge of every wild type strain.

The use of multitarget-ribozymes against cellular RNAs which contain highly conserved target sequences may prove to be the method of choice, since it will be the most effective per RNA copy as compared to antisense or monoribozymes. It can also be anticipated that the random choice of multiple target sites and the synthesis of multitarget-ribozymes from synthetic oligonucleotides may prove to be faster and more effective in destroying a specific cellular RNA than evaluating the efficiency of every single target site in vitro which would have to be followed by more elaborate in vivo studies. The present invention can be illustrated by the use of the following non-limiting examples:

EXAMPLE I

Procedures Utilized in the Preparation of the DNA Constructs

The following procedures were used in creating the constructs of the present invention:

1) Preparation of Plasmid DNA

This standard procedure for the isolation of plasmid DNA from host bacterial cells is outlined in Maniatis et al. (Maniatis, T., et al., Molecular Cloning: A laboratory manual. Cold Spring Harbor Laboratory, N.Y. (1982)). This is also described by Birnboim and Doly (Birnboim, H. C., et al., Nucl. Acids Res. 7:1513 (1979)). Briefly, it involves the growth of bacterial cells in liter-quantities, the lysis of the cell by alkali, and the purification of the plasmid DNA by equilibrium centrifugation in a cesium chloride-ethidiumbromide density gradient.

2) Restriction Enzyme Digestions

For the analyses of the DNAs and before the cloning of DNA fragments as described below, approximately 1 μg of DNA is added to the following reaction: 10 μl of 10× restriction buffer (depending on the restriction enzyme, manufacturer's conditions are used, and 1 to 9 μl of the appropriate restriction enzyme adjusted with water to a final volume of 100 μl. The mixture is then incubated for at least 1 hour at the recommended temperature.

3) Purification of Restriction Fragments

After restriction enzyme digestion of the DNAs, the fragments are extracted with an equal volume of phenol/chloroform and the aqueous phase is precipitated with ethanol. The fragments are dissolved in buffer and separated on a 1% agarose gel according to standard procedures. The specific bands are excised from the gel, phenol extracted and ethanol precipitated. The DNA is dissolved in buffer after which it is ready to be used for DNA ligations.

4) Ligation of DNAs a) Preparation of the vector DNA: 1 μg of the cloning vector is cleaved with appropriate restriction enzyme(s) to completion. If a blunt-end ligation is planned, the ends are flushed with Klenow fragment as described below. The vector is then treated with calf alkaline phosphatase. ¹⁄₁₀th of the preparation is examined on standard agarose gels to make sure no circular form of the DNA remains, and there is complete cleavage.

b) Preparation of the insert DNA: Insert DNA is either prepared by PCR reactions or by restriction enzyme digestion or by a combination of both to ensure compatibility of the insert DNA ends with those of the vector DNA ends with which they are to be covalently linked.

c) Ligation: 0.1 μg of the vector DNA is mixed with a 5-fold molar excess of insert DNA (for blunt-end ligation a 10-fold excess is used) in 20 μl of 50 mM Tris-HCl pH7.6, 10 mM MgCl2 and 1 mM ATP and 1 unit of T4 DNA ligase. The mixture is incubated for 4 hrs at 16° C.

5) Fill-in of Recessed DNA Ends 10 pmol of 5' protruding DNA is converted to blunt end by treating with 1 U of DNA polymerase (Klenow fragment) together with 125 uM dNTPs each in 0.05M NaCl, 6.6 mM Tris-HCl, 6.6 mM MgCl$_2$, 1 mM DTT in 30 min at 30° C. The enzyme is then heat inactivated during incubation at 65° C. for 15 min. 3' overhanging sequences which need to be removed are incubated the same way but without dNTPs.

6) Transformation of E. coli

Competent E. coli strains (JM109 or HB101) are available from Promega. 2 μl of the ligation production are added to 100 μl of competent cells and mixed gently. The cells are incubated for 10 min on ice, heated for 45 sec at 42° C. and again kept on ice for 2 min. LB media is added and the suspension is incubated for 60 min at 37° C. with occasional mixing. 100 μl of the suspension is then plated on LB agar plates containing the appropriate antibiotics (usually ampicillin), and the plates are incubated overnight at 37° C.

7) Identification of DNA Clones

The analysis of cloned DNA from bacterial cell colonies is a modification of the DNA isolation procedure as described above without the cesium chloride gradient. It involves an alkaline lysis of single bacterial colonies and the processing of the DNA on a miniature scale. The DNA is then digested with the appropriate restriction enzymes and the fragments are analyzed on agarose gels. The specific restriction enzyme cleavage pattern reveals the structure of the insert DNA of a particular clone.

8) Oligonucleotide Synthesis

All oligonucleotides which are described below were synthesized using solid-phase phosphoramidites chemistry on Applied Biosystem Instruments Automated DNA Synthesizer Model 380A with the procedure and the chemicals recommended by the manufacturer.

9) Polymerase Chain Reactions

Each reaction, whether it is a gene fusion reaction or a simple DNA amplification reaction (Saike, R. K., et al., Science 239:487–491 (1988)), contains: 1 μg DNA template (s) (each, for gene fusion), 1 uM of 20 nucleotide long terminal oligonucleotide primers (varying amounts of 40 nucleotide long fusion primer(s) between 100 nM to 0.1 nM, for gene fusion, ref. 47??), 10 mM Tris-HCl pH 8.4, 2.5 mM MgCl12, 50 mM KCl, 200 μg/ml gelatin, 2 units Taq DNA polymerase (Perkin-Elmer-Cetus, Norwalk, Conn.) in a final volume of 100 μl. The reactions are carried out using a Perkin-Elmer-Cetus DNA thermal cycler set at 30 repeated cycles of 1 min at 95° C., followed by 2 min at 45° C., followed by 3 min at 70° C. After 30 cycles there is an extension for 7 min at 70° C. The product DNA is directly analyzed on agarose gels according to standard procedures. The fused fragment is isolated from the gel, purified and, after cleavage with appropriate restriction enzymes, it is cloned into the appropriate plasmid DNAs as described for each individual DNA construct.

10) Gene Fusion

The precise fusion of two DNA molecules at predetermined sites, which is essential for most of the DNA constructions described below, is carried out by procedures previously developed (Schubert, M., et al., J. Virol. (66: 1579–89) (1992); Yon, J., Nucl. Acids. Res. 17:4895 (1989)). Three different methods were originally developed in the lab of the present inventors which all yield the same product DNA. The three methods are similar, and they all require the two starting DNAs which contain the sites at which fusion is carried out (e.g., for the construction of CD4/env see FIG. 3). Depending on the particular fusion method used, three or four synthetic oligonucleotides are added to the DNAs for the fusion and amplification of the fused DNA product.

All essential components of a standard polymerase chain reaction are added (see above) and the reaction is carried out in a DNA thermal cycler (Perkin-Elmer-Cetus, Norwalk, Conn.). The reactions are completed in about 5 hours, and enough fused product is usually synthesized for direct cloning into appropriate plasmid vectors. The success of the DNA fusion is dependent on the synthetic oligonucleotide primers used. Two primers, which are in excess (1000 nM), are the terminal primers. They are needed for the amplification of the complete, fused DNA and they usually contain unique restriction enzyme cleavage sites for efficient cloning. One or two fusion primers which are added to the reaction are about 40 nucleotides in length. They are identical to the fused region in the final construct. About 20 nucleotides of each of the two DNAs are represented in the fusion primer(s). Most importantly, the molar ratio of the fusion primers relative to the terminal primers is drastically decreased. It is most efficient to run several fusion reactions in parallel with the fusion primer concentrations varied from 100 nM to 0.1 nM, while the terminal primers are at 1000 nM. The reaction which yields an optimum of the fused DNA usually has sufficient DNA for direct cloning. In some cases, isolated fused DNAs need reamplification using a second polymerase chain reaction together with only the terminal primers.

11) Nucleotide Sequence Analysis

DNA sequencing is performed using a chain termination method. The materials obtained are in a kit from US Biochemicals. Basically the protocols suggested by the manufacturer are followed. 2 µg of DNA is denatured with 2N NaOH and annealed with 10 ng of primer. Sequencing reactions are carried out using USB Sequencing kit and 35S DATP (specific activity >3000 Ci/mmol, Amersham). The reactions are heated for 2 min at 90° C. before 2 µl each are applied to a 6% polyacrylamide gel containing standard 1× Tris-borate-EDTA, 7M urea buffer. After electrophoresis the gel is fixed in 10% acetic acid and methanol for 10 min, dried under vacuum and exposed to X-ray film.

12) Computer Analysis of the Nucleotide Sequences

All nucleotide sequences were analyzed on Macintosh SE/30 and Mac II computers using the DNA-strider 1.0 program application. The sequences of pNL4-3 and CD4 were entered by copying from a gene library. All sequences of the DNA constructs below were confirmed by direct sequencing. Minute differences from published sequences have been included in the attached sequences. Since the various prototype constructs are generated in a successive order, any new additions or deletions are confirmed by direct sequencing of the DNAs and these sequences are listed in the FIGURES.

EXAMPLE II

Construction of HD1

For the initial construction of HD1, a chimeric CD4/env gene was assembled and cloned. This was achieved by first amplifying the ectodomain region of CD4 found in the pT4B plasmid (Maddon, P. J., et al., Cell 42:93–104 (1985)) in a polymerase chain reaction and amplifying the transmembrane and cytoplasmic domain of the HIV env protein found in pPEenv5(Adachi, Akio, et al., J. Virol. 59:284–291 (1986)). The ectodomain region of CD4 was amplified using the following synthetic oligonucleotides which also at the same time introduces a unique XhoI site at the 5' end of the CD4 gene fragment and a CD4/env fusion oligonucleotide at the 3' end:

OMS1: (SEQ ID NO:15:) ATCTCGAGATGAA-CCGGGGAGTCCCTTTTAGGCACTTGCTT,

OMS25: (SEQ ID NO:16:) AGCCTCCTACTATCAT-TATGAATAACATTGGCTGCACCGGGG TGGAC-CAT.

The transmembrane and cytoplasmic domains of HIV env were amplified with the following oligonucleotides which also introduce a fusion oligonucleotide at the 5' end of the transmembrane region and a unique BssH2 site at the 3' end of the env gene:

OMS 27: (SEQ ID NO:17:) ATGGTCCACCCCGGTG-CAGCCAATGTTATTCATAATGATAG TAGGAG-GCT

D2: (SEQ ID NO:18:) ATCGCGCGCATCTTATAG-CAAAATCCTTTCCAAGCCCTGTCTTA.

After the amplification of the two fragments and purification on an agarose gel, they were combined in a standard gene fusion reaction and the gene fusion was carried out with the addition of the two terminal primer oligonucleotides OMS1 and D2. The fused DNA fragment consisting of a precisely fused CD4/env gene was cleaved using Xho1 and BssH2 and was cloned under control of a T7 RNA polymerase promoter into pET9 which is a modified ET3a plasmid. This CD4/env fusion gene is the starting material for the HD1 construction. To fuse the chimeric receptor so it is under control of the HIV LTRs, two gene fusions are needed at both termini of the CD4/env gene. Gene fusion A precisely replaces the AUG of the HIV gag gene with the AUG of the CD4/env gene. This is achieved in a gene fusion reaction which contains pNL4-3 and CD4/env DNA as well as two terminal oligonucleotides (HIV1 and HIV4) and one fusion oligonucleotide (HIV2). The 5' terminal oligonucleotide contains a terminal Xba1 site followed by all nucleotides of the 5' LTR of HIV, the 3' terminal oligonucleotide of this reaction primes within the CD4 region shortly downstream of the unique Bcl1 site. This allows the isolation of a fused DNA which is easily cloned at Xba1 and Bcl1. The nucleotide sequences of the three oligonucleotides are:

OHIV1: (SEQ ID NO:19:) ATAGTCTAGATG-GAAGGGCTAATTTGG

OHIV4: (SEQ ID NO:20:) TTCTTGATGATCAGGGG-GAAGTTTCCTTGG

OHIV2: (SEQ ID NO:21:) CTAAAAGGGACTCCCCG-GTTCATCTCTCTCCTTCTAGCCTCC.

After the PCR reaction, the fragment was cleaved with Xba1 and Bcl1 and isolated from a gel. The fragment is called p44 and is used below.

For the fusion of the 3' terminal region of CD4/env with the HIV 3' LTR, the following gene fusion was carried out which uses again pNL4-3 and CD4/env DNA as well as the following terminal oligonucleotide primers OHIV6 and OHIV7. OHIV7 introduces a polylinker and a unique Bcl1 site at the 3' terminal region of the HIV 3' LTR. OMS27 is a fusion primer which fuses the chimeric CD4/env fragment precisely to the nef region of HIV. The sequences of the three primers are:

OHIV6: (SEQ ID NO:22:) AAAACGGGTTACCCAG-GACCCTAAGCTCCA

OHIV7: (SEQ ID NO:23:) CGCTGATCAAACCGCG-GTTGGGCCCTGCTAGAGATTTTCCAC TGACTA

OMS27: (SEQ ID NO:17:) ATGGTCCACCCCGGTG-CAGCCAATGTTATTCATAATGATAG TAGGAG-GCT.

Following the PCR reaction, the fragment was cleaved with BamH1 and Bcl1 and is ligated into a plasmid which contains the CD4/env gene and which is also cleaved with BamH1 followed by phosphatase treatment. This allows the insertion of the BamH1/Bcl1 fragment since Bcl1 and BamH1 are compatible cloning sites (although recutting is not possible at this site). The clone with the fragment insertion is called p18.

For the assembly of the first prototype defective HIV DNA (although not HD1 yet), p18 DNA was cleaved with Xba1 and BamH1. The excised fragment was replaced by the Xba1/BamH1 fragment of p44 DNA which contains the precise 5' LTR/CD4 fusion as described above. The resulting DNA was cloned and is called pDl1. The CD4/env protein in this construct contained sequences from BH10 HIV genomic DNA. This region was completely replaced in the HD1 construct by the corresponding sequences of pNL4-3. pDl1 DNA was cleaved with BstE2 and BamH1 and this region was replaced by a new CD4/env gene fusion product which was generated by gene fusion using pNL4-3 and pT4B DNA and the following terminal primers OHIV6 and OHIV20 and the fusion primer OMS27. The sequences of OHIV6 and OMS27 are listed above, the sequence of OHIV20 (SEQ ID NO:24:) is: CAGGCCATCCAATCA CACTA.

The new DNA fragment was cloned into pDl1 and the new clone which only carries HIV sequences from pNL4-3. The entire insert, which is identical to HD1 DNA, was recloned into the pGem4XB vector (Emerson, S. U., et al., Proc. Natl. Acad. Sci. USA 84:5655–5659 (1987)) after the vector and the HD1 insert were cleaved with Xba1 and EcoR1. This allows for an efficient cloning. During the cloning into pGem 4XB, the Xba1 site of HD1 DNA was accidentally lost. The HD1 clone was sequenced in its entirety on both strands using approximately 20 different oligonucleotides. The precise sequence is shown in the FIGURES and includes multiple minor changes from published sequences of the corresponding regions.

EXAMPLE III

Construction of HD2

The insertion of ribozyme Rz6 into HD1 was accomplished by precise gene fusion using the 4 synthetic oligonucleotides listed below. The choice of the fusion oligonucleotides allows for the deletion of, for example, the translational start codon for the HIV nef protein, while at the same time it allows the addition of sequences like the ribozyme and unique cloning sites for a continuously easier generation of new prototypes of defective HIV proviruses. The oligonucleotides which were used for the gene fusion cloning have the following sequences. The terminal oligonucleotides are:

OHIV 22: (SEQ ID NO:25:) GGTCAGTGGATATCT-GACCC

OHIV 32: (SEQ ID NO:26:) AGATCCATTCGATTAGTGAA

The fusion oligonucleotides which contain the ribozyme active site are:

Rz1: (SEQ ID NO:27:) CTGATGAGTCCGTGAGGAC-GAAACTGTGCTGCGGCCGCTATA AGGTGGCAA GTGGTCAAAA,

Rz2: (SEQ ID NO:28:) CGTCCTCACGGACTCATCAG-CAATGTACCATATGCTTATAGCAAAATCCTTT.

Two separate polymerase chain reactions using OHIV22 and Rz1 (for the 5' terminal portion overlapping the unique restriction site BamH1 in CD4/env) or OHIV 32 and Rz2 (for the 3' terminal portion overlapping the unique restriction site Kpn1) were set up, respectively. The two fragments were isolated, and combined for the fusion PCR reaction together with the terminal oligonucleotides OHIV22 and OHIV32. The fused fragment was isolated, cleaved with BamH1 and Kpn1 and directly ligated and cloned into HD1 which was also cleaved with BamH1 and Kpn1. This resulted in HD2 DNA and the sequence at the fusion point and the ribozyme site was confirmed by DNA sequencing.

EXAMPLE IV

Construction of HD3

This DNA contained an additional rev responsive element (RRE), which was isolated and amplified by PCR using the following synthetic oligonucleotides:

OHIV 34: (SEQ ID NO:29:) GAGCTAGCGGCCGCAG-GAGCTTTGTTCCTTGGGTT.

OHIV 35: (SEQ ID NO:30:) TCTGAAGCGGCCGCAG-GAGCTGTTGATCCTTTAGG.

The approximately 260 nucleotide long fragment, which through the oligonucleotides contains terminal Not1 sites, was cleaved with Not1 and cloned directly into the unique Not1 cleavage site of HD2, which was treated with phosphate after Not1 cleavage to decrease the number of background *E. coli* colonies which were derived from simple religation. The correct orientation of the RRE insert was determined by restriction enzyme analysis and confirmed by direct sequencing.

EXAMPLE V

Construction of HD4

The NONARz63-6 cassette was amplified using the polymerase chain reaction and the following synthetic oligonucleotides:

Xho37: (SEQ ID NO:31:) GATCCTCGAGCCAT-AATACTGATGAGTCCG

KpnD: (SEQ ID NO:32:) GATCGGTACCGTAGCAAT-GTTTCGTCCTCA

The approximately 400 nucleotide long amplified cassette was partially cleaved with Xho1 and completely cleaved with Kpn1. This was achieved by carrying out parallel reactions containing different amounts of Xho1 endonuclease. HD3 was cleaved with Kpn1 and Xho1, and this fragment was directly ligated into HD3, cloned and sequenced.

Expression of this particular defective interfering HIV-1 DNA construct causes interference with HIV-1 replication by two different mechanisms: the action of the chimeric CD4/env receptor and the cleavage of HIV env RNA by the multitarget-ribozyme.

EXAMPLE VI

Construction of HD5

This prototype DNA contains the first 66 nucleotides of the HIV gag gene (with the translational start site of gag inactivated) specifically inserted in front of the AUG of the CD4/env gene to increase efficiency of packaging the RNA. For the insertion of this region, the following reactions and DNA clonings were carried out as follows:

a) pNL4-3 was used as a template in a PCR reaction using the following oligonucleotides:

OHIV43: (SEQ ID NO:33:) CTGAAGCGCGCACGGCAAGA,

OHIV57: (SEQ ID NO:34:) TATCTAATTCTCCCCCGCT-TAATACCGACGCTCTCGCACCCAA CTCTCTC.

The product from this reaction was isolated from the gel and used as a template in the next PCR reaction:

b) the following oligonucleotides were used:

OHIV43, see above,

OHIV61: (SEQ ID NO:35:) TCGCCGGTTCATCTCCTAT-TACCGAATTTTTTCCCATTTATCT AATTCTC.

The product from this reaction was isolated from the gel.

c) A PCR reaction using pHDl1 DNA as a template and the following oligonucleotides was carried out and the DNA fragment was, again, isolated from the gel.

OHIV60: (SEQ ID NO:36:) GAGAATTAGATAAATGG-GAAAAAATTCGGTAATAGGAGATGAA CCGGGGA,

OHIV47: (SEQ ID NO:37:) GGTGCCACTATCCTG-GAGCTCCA.

d) The fragments from the PCR reaction b) and c) were combined for gene fusion by PCR using oligonucleotides OHIV47, OHIV43 and OHIV61 as listed above. The fused DNA was isolated from the gel, cut with BssH2 and BstX1 and cloned into pHDl1 which is also cleaved with the same enzymes. The new DNA was called pGagDl1.

e) For the final cloning of HD5, HD4 DNA was cleaved using BstE2 and Kpn1 and the insert was isolated from gel. pGagDl1 as described in d) was also cleaved with BstE2 and Kpn1 and the fragment from HD4 was directly ligated into this vector and cloned. The resulting vector was HD5.

EXAMPLE VII

Construction of HD6

The construction of HD6 requires many different PCR steps to insert translational stop condons at about every 150 nucleotides within the first 639 nucleotides of the HIV gag region. This region is, with these modifications, introduced in front of the AUG of CD4/env gene of HD4. This allows for a more efficient packaging of the DNA. The following reactions were carried out:

a) pNL4-3 was used as a template in a PCR reaction together with the oligonucleotides OHIV43 (see above) and OHIV63: (SEQ ID NO:38:) ACAGCCTTCTCAT-GTCTCTA (stop codon at pos. 949 in pNL4-3) The fragment was isolated from gel.

b) pNL4-3 as template together with the following oligonucleotides (introducing a stop codon at 1096):
OHIV62: (SEQ ID NO:39:) TAGAGACATGAGAAG-GCTGT
OHIV65: (SEQ ID NO:40:) GCTCTC-CTATATCTAATCTAAGGC.

c) pNL4-3 as template together with the following oligonucleotides (introducing a stop codon at 1222):
OHIV67: (SEQ ID NO:41:) TGGCCTAATGTACCATTTGC,
OHIV64: (SEQ ID NO:42:) GCCTTAGATTAGATAGAG-GAGAGC.

d) pNL4-3 as template together with the following oligonucleotides (introducing a stop codon at 1372):
OHIV69: (SEQ ID NO:43:) GCATGGCTGCTTAATGTCCC,
OHIV66: (SEQ ID NO:44:) GCAAATGGTACATTAG-GCCA.

Gene fusion of the region which contains the four artificial stop codons was carried out in two steps:

e) The product DNAs from reactions a) and b) were combined and amplified by PCR using oligonucleotides OHIV43 and OHIV65.

f) The product DNAs from reactions c) and d) were combined and amplified by PCR using oligonucleotides OHIV64 and OHIV69.

g) The product DNAs from reactions e) and f) were combined and amplified by PCR using oligonucleotides OHIV43, OHIV65 and OHIV69.

For the insertion of the stopped gag region in front of the CD4/env gene, the following PCR reactions were carried out.

h) pNL4-3 as a template using the following oligonucleotides in a PCR reaction:
OHIV56R: (SEQ ID NO:45:) ACT-CCCCGGTTCATCTCCTATTATTCTGCAGCTTCCT-CATT,
OHIV68: (SEQ ID NO:46:) GGGACATTAAGCAGC-CATGC.

i) The products of reactions g) and h) were used in a gene fusion reaction together with the oligonucleotides OHIV43, OHIV56R and HIV68.

j) pHD1 DNA as a template using the following oligonucleotides in a PCR reaction:
OHIV55R: (SEQ ID NO:47:) AATGAGGAAGCTGCAGAATAATAGGAGATGAA-CCGGGGAGT, and OHIV47.

k) The product DNA fragments of the PCR reactions i) and j) were combined and fused by gene fusion using the oligonucleotides OHIV47, OHIV43 and OHIV56R. The amplified fused product was isolated from gel, cleaved with BssH2 and BstX1 and cloned into pHD1 which was also cleaved with the same enzymes to form pGagD12.

l) To add the multitarget ribozymes, pGagD12 as well as HD4 were digested with Kpn1 and BstE2, and the ribozyme region was cloned into pGagD12 to form pHD6.

EXAMPLE VIII

Construction of the Packaging Provirus

DNA Construct HDPACK1

The packaging provirus DNA construct requires a number of deletions and the addition of a polyA site.

a) pNL4-3 as a template was used in a PCR reaction using the following oligonucleotides as primers:
PACK Primer #1: (SEQ ID NO:48:) GAAGCGCGCACG-GCAAGAGGCGAGGGGCGGCGACTG GTGAGAGATGGGTGCGAGAGCGTCGG.
PACK Primer #2: (SEQ ID NO:49:) GGCCCTGCATG-CACTGGATG.

The fragment was isolated and cleaved with BssH2 and Sph1. Primer #1 is a deletion primer which removes part of the essential packaging signal of HIV.

b) pNL4-3 was cleaved with Sph1 and EcoR1 and the 4.3 kb fragment was isolated.

c) The products of reactions a) and b) were ligated in a three piece ligation into pHDl1 which has been cleaved with BssH2 and EcoR1.

d) For deleting a big piece in the env region without affecting any other gene products, pNL4-3 was used as a template and for a gene fusion reaction which introduced the deletion in env. The following terminal and fusion primers were used:
PACK Primer #3: (SEQ ID NO:50:) CATAATAAGAAT-TCTGCAAC.
PACK Primer #4: (SEQ ID NO:51:) CAAGTTAACAGCACTATTC,
PACK Primer #5: (SEQ ID NO:52:) GGGATATTGATGATCTGTAGAATAGGAGCTTTG-TTCCTTGGG,
PACK Primer #6: (SEQ ID NO:53:) CCCAAGGAA-CAAAGCTCCTATTCTACAGATCATCAATATCCC.

The approximately 1400 bp fragment was isolated and cleaved with EcoR1 and Hpa1.

e) For the generation of a new polyA site after elimination of the 3' LTR, the polyA site of SV40 was used. It was isolated after PCR amplification from the plasmid DNA pJC119 using the following primers:
PolyA1: (SEQ ID NO:54:) TAGTTAACATAAGATACATTGATGAGT,
PolyA2: (SEQ ID NO:55:) TAGCTAGCATCATAATCAGCCATACCAC.

The polyA site containing approximately 240 bp fragment was isolated and cleaved with EcoR1 and Nhe1.

f) For the final step, the DNA clone from step c) was cleaved with EcoR1 and Nhe1 and the fragments from reactions d) and e) were cloned into c) in a three piece ligation. The resulting clone was pHDPACK1.

EXAMPLE IX

Construction of HD1 (T7)

For the construction of a DNA (which not only can be transcribed in vitro and in vivo using T7 RNA polymerase, but the RNA transcript is identical to the RNA product which the cellular RNA polymerase II would synthesize in vivo from prototype HD1 DNA), the following oligonucleotides were used:

5' terminal oligonucleotide which contains an EcoR1 site, a T7 RNA polymerase promoter followed precisely by the initiation site for transcription of RNA polymerase II: (SEQ ID NO:56:) GCGAATTCTGTAATACGACTCACTATAGGTCTCTCTGGTTAGACCAGATCTGAG, 3' terminal oligonucleotide which contains a 3' terminal Pst1 cloning site and which overlaps with the HIV polyadenylation site in the 3' LTR. Instead of poly(A) addition by cellular enzymes, this construct encoded a short 16 A residues in + sense: (SEQ ID NO:57:) CGCTGCAGATGCATTTTTTTTTTTTTTTTGAAGCACTCAAGGCAAGCTTTATTG, The entire, approximately 2.9 kb construct was assembled in a three piece ligation using a unique BamH1 site within the cytoplasmic domain region of the chimeric CD4/env gene. Two partial fragments were amplified in a PCR reaction using HD1 DNA and the 5' terminal primer listed above together with the internal primer: No. 29: (SEQ ID NO:58:) TTGAGCAAGTTAACAGCACT.

The 3' terminal oligonucleotides was also used on HD1 DNA in a PCR reaction together with the internal primer No. 32: (SEQ ID NO:59:) AGATCCATTCGATTAGTGAA.

The amplified 5' terminal fragment of the construct was digested with EcoR1 and BamH1, the 3' terminal fragment is cleaved with BamH1 and Pst1. A pGEM 3Z DNA plasmid (commercially available from Promega) was cleaved with EcoR1 and Pst1 and the two amplified and cleaved fragments were ligated asymmetrically and cloned into this plasmid DNA in a single, three piece ligation.

EXAMPLE X

Construction of MONORz37

The two synthetic, partially complementary oligonucleotides RZ V with the sequence (SEQ ID NO:60:) TTCTCGAGGCGGCCGCGTCACAGTTTCGTCCTCACGGACTCATCAG and RZ VI with the sequence (SEQ ID NO:61:) TTAAGCTTCATATGCCATAATACTGATGAGTCCGTGAGGACG were annealed and the recessed 3' ends of the hybrid were filled in with DNA polymerase (Klenow fragment) and dNTPs. The resulting completely double stranded DNA fragment was cleaved with Hind3 and Xho1 and cloned directly into the plasmid pGem4XB (Emerson et al., Proc. Natl. Acad. Sci. USA 84:5655–59 (1987)), which was linearized by Hind3 and Xho1 cleavages.

EXAMPLE XI

Construction of MONORz6

Two synthetic, partially complementary oligonucleotides RZ III with the sequence (SEQ ID NO:62:). TTTCTCGAGGCGGCCGCAGCACAGTTTCGTCCTCACGGACTCATCAG and RZ IV with the sequence (SEQ ID NO:63:) TTAAGCTTCATATGGTACATTGCTGATGAGTCCGTGAGGACG were annealed and the recessed 3' ends of the hybrid were filled in with DNA polymerase (Klenow fragment) and dNTPs. The resulting completely double stranded DNA fragment was cleaved with Hind3 and Xho1 and cloned directly into the plasmid pGem4XB (Emerson et al. supra (1987)), which was linearized by Hind3 and Xho1 cleavages.

EXAMPLE XII

Construction of DIRz27

The MONORz27 was cleaved with Xba1, filled in with dNTP and DNA polymerase (Klenow fragment). The MONORz6 was excised by cleavage with Hind3 and Xba1. The terminal recessed ends of the DNA fragment was filled in with dNTPs and DNA polymerase (Klenow fragment). The fragment was ligated into the linearized MONORz37 by blunt end ligation and is directly cloned. Correctly-oriented cloned fragments were identified by restriction enzyme analyses and are confirmed by direct sequencing of the DIRz27 insert.

EXAMPLE XIII

Construction of PENTARz51 and PENTARz63

Preparation of a TETRARZ-ABCB cassette: For the construction of this cassette the four partially complementary, synthetic oligonucleotides were used:
A: (SEQ ID NO:64:) TTATGCATCCCGGGATCCCATACTGATGAGTCCGTGAGGACGAAA CTGATTA AATCGCAACTGATGAGTCCG,
B: (SEQ ID NO:65:) CGGGACTCATCAGCACATGGACGGCTGGTTTCGTCCTCACGGAC TCATCAG TTGCGATT,
C: (SEQ ID NO:66:) TCCATGTGCTGATGAGTCCGTGAGGACGAAACATTGTAGAGG GGCACTGATGAGTCCG,
D: (SEQ ID NO:67:) TTACGCGTACTAGTAGCAATGTTTCGTCCTCACGGACTCATCAGTGCCCTC.

These oligonucleotides were annealed and filled in with dNTPs and DNA polymerase (Klenow fragment). The filled in fragment DNA was amplified by polymerase chain reaction using the following shorter primers, which are subsets of the terminal oligonucleotides A and D listed above:
XhoAA: (SEQ ID NO:68:) GATCCTCGAGATCCCGG-GATCCCATACTGA
EcoDD: (SEQ ID NO:69:) GATCGAATTCGCGTACTAGTAGCAATGTTTCG The amplified PCR product was cleaved with BamH1 and EcoR1 and the cleaved fragment was cloned directly into either the MONORz6 DNA or MONORz37 DNA which were also linearized with BamH1 and EcoR1 to yield the pentaribozymes PENTARz51 and PENTARz63, respectively.

EXAMPLE XIV

Construction of NONARz63-6

The construction of the nonaribozyme starts with the assembly of a TETRAZEFGH cassette. For the construction of the cassette the following four, partially complementary oligonucleotides were used:
E: (SEQ ID NO:70:) GATCGTCCGACGTTAATTTCT- GATGAGTCCGTGAGGACGAAACACA TGGTGCCATTTCTGATGAG,
F: (SEQ ID NO:71:) CTCATCAGCAAGACCCACTGCT- GTTTCGTCCTCACGGACTCATCA GAAATGGCA,
G: (SEQ ID NO:72:) GGGTCTTGCTGATGAGTCCGT- GAGGACGAAACAATTAATTTTGCT CCTGATGAG,
H: (SEQ ID NO:73:) GATCGGATCCACATT- AGTTTCGTCCTCACGGACTCATCAGGA GCAAAA.

These oligonucleotides were annealed and the recessed 3' terminal regions were filled in using dNTPs and DNA polymerase (Klenow fragment). The resulting fragment was amplified by PCR using shorter primers which are subsets of the terminal primers E and H.
H-sh: (SEQ ID NO:74:) GATCGGATCCACATT- AGTTTCG
E-sh: (SEQ ID NO:75:) GATCGTCGACGTTAATTTCTGA The amplified fragment was cleaved with BamH1 and Sal1, and it was directly ligated and cloned into the PENTARz63 DNA, which has also been cleaved by BamH1 and Sal1 to generate the NONARz63-6 cassette within the plasmid DNA.

This nonaribozyme is targeted to cleave HIV-1 env HIV-1 env RNA at up to nine different conserved sites.

EXAMPLE XV

Cells. Tissue Culture & Vaccinia Virus Propagation

Hela cells were obtained from the American Type Culture Collection, Hela T4 cells are obtained from AIDS repository at NIH, as were pT4B and pNL4-3 DNAs. penv5 and Vaccinia virus TF7-3 were gifts. Hela and HelaT4 cells are grown in Eagle's minimal essential medium supplemented with 10% fetal bovine serum, nonessential amino acids, glutamine and penicillin and streptomycin according to standard procedures. The cells were kept at 37° C. and were split every 3 to 4 days using trypsin-EDTA. Vaccinia virus is grown in Hela cells after a 1 hr adsorption starting with different multiplicities of infection. Virus stocks are made by initially infecting the cells at a multiplicity of infection of less than 0.2 infectious particles per cell. After two days in culture, the cells are collected, homogenized and the virus is purified from the cell extract by ultracentrifugations using sucrose gradients. Light-scattering virus bands are collected and the virus is pelleted and resuspended by sonification.

EXAMPLE XVI

DNA Transfections

Varying concentrations DNA (from 20–3000 ng) were added to 0.5 ml of minimal essential medium (MEM) and an equal volume of diluted lipofectin reagent (BRL, Bethesda) was added which contains 30 μl of lipofectin for a 3.5 cm well. Monolayer cultures of Hela or Hela T4 cells were washed twice with 1×PBS and once with MEM, then the lipofectin-mix was added to the cells and incubated at 37° C. for 4 to 6 hrs. After this incubation the medium was removed and replaced with 1 ml of Dulbecco MEM containing 10% fetal bovine serum. The cells were incubated at 37° C. for various lengths of time and screened, depending on the experiment for p24 antigen release, syncytia formation or for drug resistance like against G418 or hygromycin B.

EXAMPLE XVII p24 Capture-ELISA Assay

Supernatants of cell cultures which contained HIV virus were collected periodically over a period of about two weeks for each experiment after removing the cells by low speed centrifugation. Depending on the experiment, the supernatants were diluted up to 10,000 fold to assure a reading for the HIV p24 antigen in the linear range of the assay up to about 250 pg/ml.

EXAMPLE XVIII

Syncytia Forming Assay and in Vivo Expression Of Genes Using Vaccinia Virus Expressing T7 RNA Polymerase Hela T4 cells were transfected with plasmid DNA such as penv5, which encodes the complete HIV env gene under control of the T7 RNA polymerase promoter as described above. After the transfection, the cells were infected at a multiplicity of infection of 20 with the vaccinia virus recombinant vvTF7-3 which expresses a functional T7 RNA polymerase in vivo. Viral adsorption was carried out in a small 200 μl volume for 30 to 60 min at 37° C. Syncytia formation was observed overnight specifically caused by HIV env protein expression. For inhibition of syncytia formation by CD4/env, a cotransfection of penv5 with a small excess amount of HD(T7) was carried out.

EXAMPLE XIX

Selection of Stable Cell Lines Expressing the Prototype Defective Interfering Proviruses The vector DNA pY3, which contains the hygromycin B resistance gene under control of the Moloney sarcoma virus LTR (Blochlinger, K., et al., Mol. Cell. Biol. 4:2929–2931 (1984)), was used as a source of the marker gene, and it was cloned together with HD1, HD2 and HD3 into pGem4XB (Emerson, S. U., et al., Proc. Natl. Acad. Sci. USA 84:5655–5659 (1987)). A different selectable marker was needed, since Hela T4 cells are already neomycin resistant. The covalent linkage of the provirus DNA with the selectable marker gene allows, after transfection of the DNA, to select cell lines which harbor the defective provirus in their genome. For the construction of the vector DNA, pY3 was initially cleaved with Hind3 and Kpn1 and the DNA fragment which contains part of the resistance gene is isolated. In a parallel reaction pY3 was cleaved with Kpn1 and Pst1 and again the fragment which contains part of the hygromycin resistance gene was isolated. After a 3 piece ligation, both fragments were cloned into pGem4XB which had been cleaved with Hind3 and Pst1 . The cloning restores the gene and allows the DNA (pHyg) to grow more efficiently using with the pGem background sequences. For the insertion of the prototype defective interfering DNAs into this pHyg vector, the hygromycin resistance gene was excised using Bgl1 and Pst1 and all three defective prototype proviruses were also excised with the same enzymes and purified. The marker gene is then ligated to each of the individual proviral DNAs giving rise to the DNA clones pHyDI1, pHydI2 and pHYDI3, which can directly be used for selection of the cell lines.

20 μg of plasmid DNA (pHyD11, pHyD12 and pHyD13) containing the selectable marker gene encoding the hygromycin-B-phosphotransferase and HD1, HD2 or HD3, respectively, were transfected into 1×10 7 Hela T4 cells. After 48 hrs these cells are split 1:4 into Dulbecco MEM containing 200 μg/ml hygromycin B (Calbiochem). Individual cell clones were selected for two weeks, expanded and analyzed by specific restriction enzyme cleavage of the genomic cellular DNA in a Southern hybridization.

EXAMPLE XX

In Vitro Transcription Using T7 RNA Polymerase and Ribozyme Digestions of env Transcripts in vitro DNA plasmids containing the ribozymes were linearized with an appropriate restriction enzyme and after phenol/chloroform extraction and ethanol precipitation, were used as a template for in vitro transcription reactions. Transcriptions were carried out with a Promega transcription kit, following the manufacturer's recommended conditions. RNA transcripts were made in 20 to 50 μl reactions containing 1 to 2 μg DNA, 40 mM Tris-HCl pH 7.5, 6 mM MgCl2, 2 mM spermidine, 20 to 50 units RNasin, 250 uM ATP, UTP, CTP and GTP and 5 to 10 units of T7 RNA polymerase. Transcriptions were carried out for 60 min. at 37° C. Parallel reactions are also carried out in the presence of 32P CTP (Amersham) to monitor and to estimate the yield of the nonradioactive reaction. After the incubation 1 unit of RNAse free DNAse is added to the reaction mixture and it is incubated for another 15 min. The transcripts were then subjected to phenol/chloroform extractions once and then precipitated with ethanol. The pellet is redissolved in RNasin and DEPC treated water and stored at −20° C. for up to one month. For the synthesis of the ribozyme substrate similar transcriptions were carried out except that 32P-CTP is added and nonradioactive CTP is limited. After the transcription reaction 1 unit of RNase free DNase is added and incubated for 15 min. The reaction mixture was placed on ice, some DEPC treated water was added and the solution is treated with phenol/chloroform, followed by ethanol precipitation. The pellet was redissolved in 1× ribozyme buffer (see below) and passed through a RNase-free minispin column (Boehriner). The yield was calculated by TCA precipitable counts per minute. 50,000 cpm of radioative substrate is normally used for each ribozyme reaction. Cleavage reactions were done in 18 μl containing the desired amounts of substrate and ribozyme in 50 mM Tris-HCl pH 7.5, 2 mM spermidine and 10 mM HCl. After mixing, the reaction was placed at 90° C. for 1 min., chilled on ice and 2 μl of 100 mM MgCl$_2$ is added. The reaction mixture was incubated at 37° C. for various times (or approximately 1 hr) or at 55° C. 10 μl of the cleavage reaction is combined with 5 μl of gel loading buffer (95% formamide with 0.01% phenolblue), heated at 90° C. for 1 min. and loaded onto a 5% polyacrylamide-7M urea gel in Tris-borate EDTA buffer, electrophoresed and autoradiographed.

EXAMPLE XXI

In Vitro Translations of CD4/env and nef

Approximately 1 μg of in vitro RNA transcripts of HD(T7) were translated in 50 μl of nuclease treated rabbit reticulocyte lysate (commercially available from Promega) in the presence of 50 uCi 35S-methionine at 37° C. for 30 min. The proteins were analyzed with or without immunoprecipitation on 10% SDS polyacrylamide gels. The isotopically labeled proteins were visualized with Enhance by autoradiography of the fixed and dried gel.

EXAMPLE XXII

Method of Packaging the Recombinant Molecule into a Viral Particle

5 μg of HDPACK1 DNA is transfected into 1 million human CD4 positive cells like H9, CEM or HelaT4 cells using the lipofection procedure. Stable cell lines which express the defective packaging provirus are selected by cotransfection with 0.5 μg of a selectable marker gene like the neomycin gene or the hygromycin B resistance gene. After selection for two weeks in the presence of 400 μg/ml of G418 or hygromycin B, individual cells are collected in miniwells, expanded and tested for their stable expression of HIV antigens such as p24.

The genomic make-up of the complete provirus is verified by Southern blot analysis. After such a cell line has been selected, it is transfected by lipofection with 5 μg of the defective interfering provirus DNAs like HD5 and HD6 which contain sequences which allow packaging of the RNA into virus particles. Again, about 1 million cells are cotransfected with 0.5 μg of a second resistant marker gene. Cells are kept under selection for two weeks in the presence of the drug. Individual cells are separated, expanded and tested by the reverse polymerase chain reaction for the release of the virus particles which have the defective interfering RNA packaged. The particles are analyzed for the presence of CDC/env and CD4 on their surface using immunoprecipitations and Western blot analysis of the proteins. After removal of the cells by a low speed centrifugation, released virus which is constitutively packaged and released into the supernatant, particularly after stimulation of the cells, is concentrated by ultracentrifugation for 90 min. in, for example, a Beckman SW28 rotor at 4° C. at 24,000 rpm onto a pad of 20% glycerol in TNE buffer, pH 7.4. The virus is resuspended by sonication after dialysis with sterile isotonic salt solution.

EXAMPLE XXIII

Generation of Defective Interfering Particles In the Absence of HIV-1

HDPACK1 was tested for its ability to produce virus particles which contain the genomes of the defective interfering HIV-1 constructs. When HDPACK1 DNA was transfected alone, into HeLa or HeLa-tat cells which constitutively express the HIV Tat protein, virus particles were released into the medium as measured by p24 antigen in the supernatant of the transfected cells. This demonstrated that the HDPACK1 DNA construct was functional, and it was, like HIV-1, able to activate itself and to express all genes necessary for the release of p24 antigen containing virus particles into the medium. The Env and Nef protein genes are deleted from the construct, as they are nonessential for virus particle formation. Cotransfection of HDPACK1 DNA with equal amounts of any of the defective, interfering HD constructs resulted in p24 antigen release at similar or slightly reduced amounts as compared with HDPACK1 alone. The released p24 antigen from a 26 ml cell supernatant could be pelleted by ultracentrifugation for 90 min., at 28,000 rpm, 4° C., using a Beckman SW28 rotor through a 10 ml 10% sucrose cushion. This procedure removed any soluble p24 antigen which may have been the result of some lysed cells. The conditions of pelleting indicated a high sedimentation coefficient typical for virus particles. Isolation of RNA from the pellet fraction, and the analysis of the RNA using reverse transcription followed by polymerase chain reactions with specific primers for polyadenylated HD RNA transcripts, showed the presence of HD genomic RNAS. The pellet fraction was suspended in buffer and applied to a 20–60% sucrose gradient spin at 30,000 rpm for 17 hr. at 4° C. in a Beckman SW41 rotor. The gradient was fractionated into 1 ml fractions, and a peak was found in the middle of the gradient which contained both the nucleocapsid p24 antigen together with the defective interfering genomic RNA. The location of the peak fraction was characteristic for the sedimentation of the defective, interfering particles. RNA isolation, reverse transcription and polymerase chain reactions confirmed the specific packaging of the DI RNA genome into the particles. This was also consistent with the amount of p24 antigen in the individual peak fractions which was proportional to the amounts of DI genomic RNA in these fractions.

What is claimed is:

1. A DNA construct which encodes a chimeric protein, said DNA construct comprising a chimeric gene operably linked to at least one human immunodeficiency virus LTR promoter sequence, where said chimeric gene comprises a first sequence encoding the ectodomain portion of the CD4 protein and a second sequence encoding the transmembrane and cytoplasmic portions of an envelope protein.

2. The DNA construct of claim 1, wherein the second sequence encodes the transmembrane and cytoplasmic portions of an envelope protein selected from the group consisting of a vesicular stomatitis virus G protein and a human immunodeficiency virus envelope protein.

3. The DNA construct of claim 2, wherein the second sequence encodes the transmembrane and cytoplasmic portions of a human immunodeficiency virus envelope protein.

4. The DNA construct of claim 3, wherein the DNA construct is the HD1 construct having the sequence shown in SEQ ID NO:2.

5. The DNA construct of claim 2, said construct further comprising the nucleotide sequence of at least one ribozyme, where said ribozyme selectively cleaves the nucleic acid sequence of human immunodeficiency viruses.

6. The DNA construct of claim 5, wherein said ribozyme sequence is selected from the group consisting of ribozyme sequences shown in SEQ ID Nos: 1, 10, 11, 12, 13 and 14.

7. The DNA construct of claim 5, wherein said construct is the HD2 construct having the sequence shown in SEQ ID NO:4.

8. The DNA construct of claim 5, wherein said construct is the HD3 construct having the sequence shown in SEQ ID NO:5.

9. The DNA construct of claim 5, wherein said construct is the HD4 construct having the sequence shown in SEQ ID NO:6.

10. The DNA construct of claim 5, wherein said construct is the HD5 construct having the sequence shown in SEQ ID NO:7.

11. The DNA construct of claim 5, wherein said construct is the HD6 construct having the sequence shown in SEQ ID NO:8.

12. A DNA construct which encodes a complete CD4 protein; said construct comprising at least one HIV LTR promoter sequence operably linked to a nucleic acid sequence encoding said CD4 protein.

13. The DNA construct of claim 12, said construct further comprising a nucleotide sequence of at least one ribozyme, where said ribozyme selectively cleaves the nucleic acid sequence of human immunodeficiency viruses.

14. A DNA construct selected from the group consisting of DIRz27, MONORz37, MONORz6, MONARz63-6, PENTARz51 and PENTARz63.

15. The DNA construct of claim 14, wherein said construct is the DIRz27 construct having the sequence shown in SEQ ID NO:1.

16. The DNA construct of claim 14, wherein said construct is the MONORz37 construct having the sequence shown in SEQ ID NO:10.

17. The DNA construct of claim 14, wherein said construct is the MONORz6 construct having the sequence shown in SEQ ID NO:11.

18. The DNA construct of claim 14, wherein said construct is the NONARz63-6 construct having the sequence shown in SEQ ID NO:12.

19. The DNA construct of claim 14, wherein said construct is PENTARz37 construct having the sequence shown in SEQ ID NO:13.

20. The DNA construct of claim 14, wherein said construct is the PENTARz63 construct having the sequence shown in SEQ ID NO:14.

21. The DNA construct HDPACK1 having the sequence shown in SEQ ID NO:9.

22. The DNA construct HD1 (T7) having the sequence shown in SEQ ID NO:3.

* * * * *